(12) United States Patent
Fyfe et al.

(10) Patent No.: US 8,193,359 B2
(45) Date of Patent: Jun. 5, 2012

(54) G-PROTEIN COUPLED RECEPTOR AGONISTS

(75) Inventors: Matthew Colin Thor Fyfe, Oxford (GB); Gerard Hugh Thomas, Oxford (GB); Lisa Sarah Bertram, Oxford (GB); Stuart Edward Bradley, Oxford (GB); William Gattrell, Oxford (GB); Chrystelle Marie Rasamison, Oxford (GB); Vilasben Kanji Shah, Oxford (GB)

(73) Assignee: Prosidion Limited, Oxford (GB)

( * ) Notice: Subject to any disclaimer, the term of this patent is extended or adjusted under 35 U.S.C. 154(b) by 832 days.

(21) Appl. No.: 11/794,220

(22) PCT Filed: Dec. 23, 2005

(86) PCT No.: PCT/GB2005/050265
§ 371 (c)(1),
(2), (4) Date: Nov. 12, 2008

(87) PCT Pub. No.: WO2006/067532
PCT Pub. Date: Jun. 29, 2006

(65) Prior Publication Data
US 2009/0099227 A1   Apr. 16, 2009

(30) Foreign Application Priority Data

Dec. 24, 2004   (GB) .................. 0428221.6
Jun. 30, 2005   (GB) .................. 0513256.8

(51) Int. Cl.
*C07D 491/048*   (2006.01)
*A61K 31/4355*   (2006.01)

(52) U.S. Cl. ........................ 546/115; 514/302

(58) Field of Classification Search ............. None
See application file for complete search history.

(56) References Cited

FOREIGN PATENT DOCUMENTS

| | | |
|---|---|---|
| EP | 0184257 A1 | 6/1986 |
| EP | 0232937 A2 | 8/1987 |
| WO | WO-9705139 A1 | 2/1997 |
| WO | WO-9746556 A1 | 12/1997 |
| WO | WO-9847876 A1 | 10/1998 |
| WO | WO-02100352 A2 | 12/2002 |
| WO | WO-2004047769 A2 | 6/2004 |
| WO | WO-2005061489 A1 | 7/2005 |

OTHER PUBLICATIONS

Johnson et al., The Discovery of a Series of N-Substituted 3-(4-piperidinyl)-1,3-benzoxazoli-nones and Oxindoles as Highly Penetrant, Selective Muscarinic M1 Agonists, 20 Bioorg. & Med. Chem. Letts. 5434-5438 (2010).*

Shkavrov, S. et al., A Convenient Synthesis of 1-Amino-7-(Piperidin-4-yl) Isoquinoline, Date: Nov. 2004.

* cited by examiner

*Primary Examiner* — Janet Andres
*Assistant Examiner* — Timothy R Rozof
(74) *Attorney, Agent, or Firm* — Mintz, Levin, Cohn, Ferris, Glovsky and Popeo, P.C.; Ivor R. Elrifi; Heidi A. Erlacher

(57) ABSTRACT

Compounds of Formula (I) or pharmaceutically acceptable salts or N-oxides thereof, are agonists of GPR116 and are useful for the treatment of obesity, and for the treatment of diabetes.

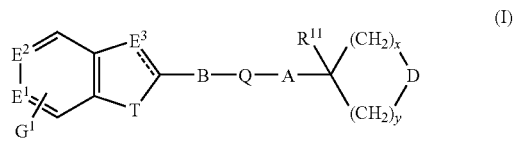

14 Claims, No Drawings

G-PROTEIN COUPLED RECEPTOR AGONISTS

BACKGROUND OF THE INVENTION

The present invention is directed to G-protein coupled receptor (GPCR) agonists. In particular, the present invention is directed to agonists of GPR116 that are useful for the treatment of obesity, e.g. as regulators of satiety, and for the treatment of diabetes.

Obesity is characterized by an excessive adipose tissue mass relative to body size. Clinically, body fat mass is estimated by the body mass index (BMI; weight (kg)/height $(m)^2$), or waist circumference. Individuals are considered obese when the BMI is greater than 30 and there are established medical consequences of being overweight. It has been an accepted medical view for some time that an increased body weight, especially as a result of abdominal body fat, is associated with an increased risk for diabetes, hypertension, heart disease, and numerous other health complications, such as arthritis, stroke, gallbladder disease, muscular and respiratory problems, back pain and even certain cancers.

Pharmacological approaches to the treatment of obesity have been mainly concerned with reducing fat mass by altering the balance between energy intake and expenditure. Many studies have clearly established the link between adiposity and the brain circuitry involved in the regulation of energy homeostasis. Direct and indirect evidence suggest that serotonergic, dopaminergic, adrenergic, cholinergic, endocannabinoid, opioid, and histaminergic pathways in addition to many neuropeptide pathways (e.g. neuropeptide Y and melanocortins) are implicated in the central control of energy intake and expenditure. Hypothalamic centres are also able to sense peripheral hormones involved in the maintenance of body weight and degree of adiposity, such as insulin and leptin, and fat tissue derived peptides.

Drugs aimed at the pathophysiology associated with insulin dependent Type I diabetes and non-insulin dependent Type II diabetes have many potential side effects and do not adequately address the dyslipidaemia and hyperglycaemia in a high proportion of patients. Treatment is often focused at individual patient needs using diet, exercise, hypoglycaemic agents and insulin, but there is a continuing need for novel antidiabetic agents, particularly ones that may be better tolerated with fewer adverse effects.

Similarly, metabolic syndrome (syndrome X) which is characterized by hypertension and its associated pathologies including atherosclerosis, lipidemia, hyperlipidemia and hypercholesterolemia have been associated with decreased insulin sensitivity which can lead to abnormal blood sugar levels when challenged. Myocardial ischemia and microvascular disease is an established morbidity associated with untreated or poorly controlled metabolic syndrome.

There is a continuing need for novel antiobesity and antidiabetic agents, particularly ones that are well tolerated with few adverse effects.

GPR116 is a GPCR identified as SNORF25 in WO00/50562 which discloses both the human and rat receptors, U.S. Pat. No. 6,468,756 also discloses the mouse receptor (accession numbers: AAN95194 (human), AAN95195 (rat) and ANN95196 (mouse)).

In humans, GPR116 is expressed in the pancreas, small intestine, colon and adipose tissue. The expression profile of the human GPR116 receptor indicates its potential utility as a target for the treatment of obesity and diabetes.

International patent application WO2005/061489 (published after the priority date of the present application) discloses heterocyclic derivatives as GPR116 receptor agonists.

The present invention relates to agonists of GPR116 which are useful for the treatment of obesity, e.g. as regulators of satiety, and for the treatment of diabetes.

SUMMARY OF THE INVENTION

Compounds of formula (I):

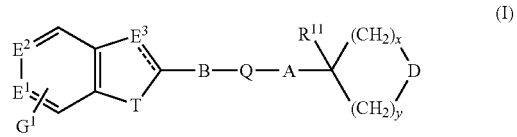

or pharmaceutically acceptable salts or N-oxides thereof, are agonists of GPR116 and are useful for the prophylactic or therapeutic treatment of obesity, and for the treatment of diabetes.

DETAILED DESCRIPTION OF THE INVENTION

The present invention is directed to a compound of formula (I):

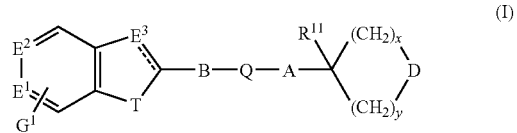

or a pharmaceutically acceptable salt or N-oxide thereof, wherein:

one of $E^1$ and $E^2$ is N and the other is N or C-$G^2$;

the dashed line together with the solid line forms an optional double bond;

when the dashed line together with the solid line forms a double bond $E^3$ is $CR^8$ or N, and when it is a single bond $E^3$ is $CHR^8$, O or $NR^2$;

T is O, S, $NR^2$, $(CH_2)_2$, or $E^4=E^5$, where $E^4$ and $E^5$ are independently CH or N;

B is a bond, —$CH_2$=$CH_2$— or $(CH_2)_j$;

j is 1, 2 or 3;

Q is a bond, C(O)S, or a 5- or 6-membered heteroaromatic ring;

A is $(CH_2)_n$, where one $CH_2$ group may be replaced by O, S, C(O), CH(OH)CH(Hal) CH($NR^2R^3$), S(O), $S(O)_2$ or $NR^3$; two $CH_2$ groups may be replaced by CH=CH, C(O)O, C(O)S, SC(O), C(O)$NR^2$ or OC(O); or three $CH_2$ groups may be replaced by C(O)$CH_2$S, C(O)$CH_2$C(OH) or C(O)$CH_2$C(O);

n is 0, 1, 2, 3, 4, 5, or 6;

$G^1$ and $G^2$ are independently hydrogen, halogen, $CF_3$, $C_{1-4}$alkoxy, $NR^4R^{44}$, $SO_2C_{1-4}$alkyl, $SOC_{1-4}$alkyl, $SC_{1-4}$alkyl or cyano; or $C_{1-4}$alkyl, $C_{2-4}$alkenyl, or $C_{2-4}$alkynyl, optionally substituted by hydroxy, $NR^4R^{44}$, oxo or $C_{1-4}$alkoxy;

D represents $CHR^9$ or $NR^1$;

$R^1$ is $C(O)OR^5$, $C(O)R^5$, $S(O)_2R^5$, $C(O)NR^5R^{10}$, $C(O)NR^{55}$, $C_{1-4}$alkylene-$C(O)OR^5$, $C(O)C(O)OR^5$, $S(O)_2R^5$, $C(O)R^5$ or $P(O)(O-Ph)_2$; or heterocyclyl or heteroaryl, either of which may optionally be substituted by one or two groups selected from $C_{1-4}$alkyl, $C_{1-4}$alkoxy, $C_{1-4}$alkyl-OH, halogen, $C_{1-4}$-fluoroalkyl, heterocyclyl, $C(O)OC_{1-4}$alkyl;

$R^2$ and $R^3$ are independently hydrogen or $C_{1-4}$alkyl;

$R^4$ and $R^{44}$ are independently hydrogen, $C_{1-4}$alkyl, $C_{3-7}$cycloalkyl, or aryl, which may optionally be substituted with 1 or 2 substituents selected from halo, $C_{1-4}$alkyl, $CF_3$, $C_{1-4}$alkoxy, cyano, and $S(O)_2Me$; or, taken together, $R^4$ and $R^{44}$ may form a 5- or 6-membered heterocyclic ring;

$R^5$ and $R^{55}$ are independently $C_{1-8}$ alkyl, $C_{2-8}$ alkenyl or $C_{2-8}$ alkynyl, any of which may be optionally substituted by one or more halo atoms, $NR^6R^{66}$, $OR^6$, $C(O)OR^6$, $OC(O)R^6$ or cyano, and may contain a $CH_2$ group that is replaced by O or S; or a $C_{3-7}$cycloalkyl, aryl, heterocyclyl, heteroaryl, $C_{1-4}$alkylene$C_{3-7}$cycloalkyl, $C_{1-4}$alkylenearyl, $C_{1-4}$alkyeneheterocyclyl or $C_{1-4}$ alkyleneheteroaryl, any of which may be substituted with one or more substituents selected from halo, $C_{1-4}$ alkyl, $C_{1-4}$ fluoroalkyl, $OR^7$, CN, $NR^7R^{77}$, $SO_2Me$, $NO_2$ or $C(O)OR^7$;

$R^6$, $R^{66}$, $R^7$, and $R^{77}$ each independently are hydrogen or $C_{1-4}$alkyl; or, taken together, $R^6$ and $R^{66}$ or $R^7$ and $R^{77}$ may form a 5- or 6-membered heterocyclic ring;

$R^8$ is hydrogen, hydroxy, $C_{1-4}$alkoxy or benzyloxy;

$R^9$ is $C_3$alkyl;

$R^{10}$ hydrogen or $C_{1-4}$alkyl;

$R^{11}$ hydrogen or hydroxy;

x is 0, 1, 2 or 3; and y is 1, 2, 3, 4 or 5;

with the proviso that x+y is 2, 3, 4 or 5.

In one embodiment of the invention the compound of formula (I) is of formula (Ia):

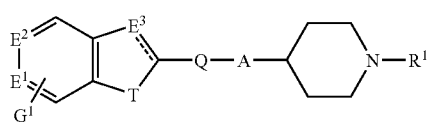

(Ia)

or a pharmaceutically acceptable salt or N-oxide thereof, wherein:

one of $E^1$ and $E^2$ is N and the other is N or C-$G^2$;

the dashed line together with the solid line forms an optional double bond;

when the dashed line together with the solid line forms a double bond $E^3$ is CH or N, and when it is a single bond $E^3$ is $CH_2$ or $NR^2$;

T is O, S, $NR^2$, $(CH_2)_2$, or $E^4=E^5$, where $E^4$ and $E^5$ are independently CH or N;

Q is a bond, C(O)S, or a 5- or 6-membered heteroaromatic ring;

A is $(CH_2)_n$, where one $CH_2$ group may be replaced by O, C(O), or $NR^3$, or two $CH_2$ groups may be replaced by CH=CH;

n is 0, 1, 2, 3, 4, 5, or 6;

$G^1$ and $G^2$ are independently hydrogen, halogen, $C_{1-4}$alkyl, $C_{2-4}$alkenyl, $C_{2-4}$alkynyl, $CF_3$, $C_{1-4}$alkoxy, $NR^4R^{44}$, or cyano;

$R^1$ is $C(O)OR^5$, $C(O)R^5$, $S(O)_2R^5$, $C(O)NR^5R^{55}$, or a 5- or 6-membered nitrogen-containing heteroaryl group;

$R^2$ and $R^3$ are independently hydrogen or $C_{1-4}$alkyl;

$R^4$ and $R^{44}$ are independently hydrogen, $C_{1-4}$alkyl, $C_{3-7}$cycloalkyl, or aryl, which may optionally be substituted with 1 or 2 substituents selected from halo, $C_{1-4}$alkyl, $CF_3$, $C_{1-4}$alkoxy, cyano, and $S(O)_2Me$; or, taken together, $R^4$ and $R^{44}$ may form a 5- or 6-membered heterocyclic ring;

$R^5$ and $R^{55}$ are independently $C_{1-6}$alkyl, $C_{2-6}$alkenyl, $C_{2-6}$alkynyl, any of which may optionally be substituted by cyano, $CHal_pH_{3-p}$, $OR^6$ or $NR^6R^{66}$, or $C_{3-7}$ cycloalkyl or 4- to 7-membered heterocyclyl either of which may optionally be substituted with $C_{1-4}$alkyl, or aryl or heteroaryl either of which may optionally be substituted with 1 or 2 substituents selected from halo, $C_{1-4}$alkyl, $CF_3$, $OR^7$, $COOR^7$, cyano, $S(O)_2Me$, $NR^7R^{77}$, and nitro;

$R^6$, $R^{66}$, $R^7$, and $R^{77}$ each independently are hydrogen or $C_{1-4}$alkyl; or, taken together, $R^6$ and $R^{66}$ or $R^7$ and $R^{77}$ may independently form a 5- or 6-membered heterocyclic ring;

Hal is fluoro or chloro; and p is 1, 2, or 3.

The molecular weight of the compounds of formula (I) is preferably less than 800, more preferably less than 600, even more preferably less than 500.

B preferably represents a bond.

In one embodiment of the invention A is $(CH_2)_n$, where one $CH_2$ group may be replaced by O, C(O), or $NR^3$, or two $CH_2$ groups may be replaced by CH=CH. n is preferably 0, 1, 2, 3 or 4.

Exemplary A groups include a bond, —$CH_2$—, —$(CH_2)_2$—, —$(CH_2)_3$—, —$CH_2$—O—, —$(CH)_2$—O—, —$CH_2$—O—$CH_2$—, —$CH_2$—O—$(CH_2)_2$—, —$CH_2$—O—$(CH_2)_3$—, —$CH_2$—O—$(CH_2)_4$—, —C(O)—$CH_2$—, —C(Cl)—$CH_2$—, —$CH_2$—NH—$CH_2$—, —$CH_2$—NH—, —$CH_2$—N($CH_3$)—, —$CH_2$—N($CH_2CH_3$)— and —$CH_2$—N($CH_2CH_2CH_3$)—.

When Q represents a 5- or 6-membered heteroaromatic ring, n is preferably 0, 1 or 2 (especially 1 or 2) and A is preferably $CH_2$, $CH_2O$ or $CH_2NR^3$. When Q represents a bond, n is preferably 2, 3 or 4, especially 2.

In one embodiment of the invention $E^3$ is CH or N. $E^3$ is preferably CH.

T is preferably O, S, $NR^2$ (for example —NH), or $E^4=E^5$ (for example —N=CH—), more preferably O. When T represents O, $E^1$ preferably represents C-$G^2$ and $E^2$ represents N.

Q is preferably a bond or a heteroaromatic ring containing up to 3 heteroatoms selected from N, O and S. In one embodiment of the invention Q is a bond.

Q is preferably a 5-membered heteroaromatic ring containing up to three heteroatoms selected from O, N and S of the formula:

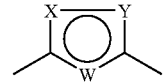

wherein W, X and Y represent the positions of the heteroatom(s) or otherwise represent CH.

Particular heteroaromatic rings which Q may represent include oxadiazole, oxazole, isoxazole, thiadiazole, thiazole and pyrazole.

Preferably two of W, X and Y are N, and the other is O.

W is preferably N.

The heteroaromatic ring described by Q is preferably oxadiazolyl, more preferably [1,2,4]oxadiazolyl.

D preferably represents $NR^1$.

In one embodiment of the invention $G^1$ is hydrogen, halogen, $C_{1-4}$alkyl, $C_{2-4}$alkenyl, $C_{2-4}$alkynyl, $CF_3$, $C_{1-4}$alkoxy, $NR^4R^{44}$, or cyano (for example hydrogen, halogen, $C_{1-4}$alkyl, $C_{2-4}$alkenyl, $C_{2-4}$alkynyl, $CF_3$, $C_{1-4}$alkoxy or cyano). Exemplary $G^1$ groups include hydrogen, halogen (for example chlorine), cyano, methyl, hydroxymethyl, methoxymethyl, dimethylaminomethyl, —CH(O), pyrrolidin-1-ylmethyl. $G^1$ is preferably hydrogen, halogen, $C_{1-4}$alkyl, or cyano, more preferably hydrogen or cyano. Another preferred $G^1$ group is methyl.

In one embodiment of the invention $G^2$ is hydrogen, halogen, $C_{1-4}$alkyl, $C_{2-4}$alkenyl, $C_{2-4}$alkynyl, $CF_3$, $C_{1-4}$alkoxy, $NR^4R^{44}$, or cyano. Exemplary $G^2$ groups include hydrogen and halogen (for example Cl). $G^2$ is preferably hydrogen, halogen, or cyano, more preferably hydrogen. Another preferred $G^2$ group is $C_{1-4}$alkyl, especially methyl. Other preferred $G^2$ groups are hydrogen, methyl and cyano.

In one embodiment of the invention $R^1$ is preferably $C(O)OR^5$, $C(O)R^5$, $C(O)NR^5R^{55}$, or a 5- or 6-membered nitrogen-containing heteroaryl group, more preferably $C(O)OR^5$. In a second embodiment of the invention $R^1$ is preferably $C(O)OR^5$, $C(O)NR^5R^{10}$, $C_{1-4}$alkylene-$C(O)OR^5$, $C(O)C(O)OR^5$, heterocyclyl, heteroaryl, $S(O)_2R^5$, $C(O)R^5$ or $P(O)(O-Ph)_2$; especially $C(O)OR^5$, $C(O)NR^5R^{10}$, $C_{1-4}$alkyl-$C(O)OR^5$, heteroaryl, $S(O)_2R^5$ or $C(O)R^5$; in particular $C(O)OR^5$, $C(O)NR^5R^{10}$, heteroaryl, $S(O)_2R^5$ or $C(O)R^5$. More preferably, $R^1$ is $C(O)OR^5$, $C(O)NR^5R^{10}$ or heteroaryl. $R^1$ is most preferably $COOR^5$. When $R^1$ is heteroaryl the heteroaryl ring is preferably pyrimidinyl, especially pyrimidin-2-yl.

When $R^1$ is optionally substituted heterocyclyl or heteroaryl, it is preferably substituted by $C_{1-4}$alkyl, $C_{1-4}$alkoxy or halogen.

Exemplary $R^2$ groups include hydrogen and methyl.

Exemplary $R^3$ groups include hydrogen, methyl, ethyl and propyl. $R^3$ is preferably $C_{1-4}$alkyl, especially methyl or ethyl.

Exemplary $R^4$ groups include methyl.

In one embodiment of the invention $R^5$ and $R^{55}$ are independently $C_{1-6}$alkyl, $C_{2-6}$alkenyl, $C_{2-6}$alkynyl, any of which may optionally be substituted by cyano, $CHal_pH_{3-p}$, $OR^6$ or $NR^6R^{66}$, or $C_{3-7}$ cycloalkyl or 4- to 7-membered heterocyclyl either of which may optionally be substituted with $C_{1-4}$alkyl, or aryl or heteroaryl either of which may optionally be substituted with 1 or 2 substituents selected from halo, $C_{1-4}$alkyl, $CF_3$, $OR^7$, $COOR^7$, cyano, $S(O)_2Me$, $NR^7R^{77}$, and nitro, where Hal represents fluoro or chloro and p is 1, 2, or 3. Preferably $R^5$ represents $C_{1-8}$ alkyl, $C_{2-8}$ alkenyl or $C_{2-8}$ alkynyl optionally substituted by one or more halo atoms or cyano, and may contain a $CH_2$ group that may be replaced by O or S; or a $C_{3-7}$cycloalkyl, aryl or $C_{1-4}$alkyl$C_{3-7}$ cycloalkyl, any of which may be substituted with one or more substituents selected from halo, $C_{1-4}$alkyl, $C_{1-4}$fluoroalkyl, $OR^7$, CN, $NR^7R^{77}$, $NO_2$ or $C(O)OC_{1-4}$alkyl. More preferably $R^5$ represents $C_{1-8}$alkyl, $C_{2-8}$ alkenyl or $C_{2-8}$ alkynyl optionally substituted by one or more halo atoms or cyano, and may contain a $CH_2$ group that may be replaced by O or S; or a $C_{3-7}$cycloalkyl or aryl, either of which may be substituted with one or more substituents selected from halo, $C_{1-4}$alkyl, $C_{1-4}$-fluoroalkyl, $OR^7$, CN, $NR^7R^{77}$, $NO_2$ or $C(O)OC_{1-4}$alkyl. Most preferred $R^5$ groups are $C_{3-5}$alkyl (optionally substituted by one or more halo atoms or cyano, and may contain a $CH_2$ group that is replaced by O or S) or $C_{3-5}$cycloalkyl (optionally substituted by $C_{1-4}$alkyl). In one embodiment of the invention the group represented by $R^5$ is unsubstituted.

In one embodiment of the invention x+y is 2, 3, or 4. In a preferred embodiment of the invention x and y each represent 1. In a more preferred embodiment of the invention x and y each represent 2.

Suitably n+j equals 1, 2, 3, 4, 5 or 6.

Preferably $R^{11}$ represents H.

When B and Q both represent a bond, suitably the group A does not represent $NR^3$.

When B-Q-A represents —$NHC_{1-4}$alkyl- and D represents $NR^1$, suitably the group $R^5$ represents $C_{1-8}$ alkyl, $C_{2-8}$ alkenyl or $C_{2-8}$ alkynyl, any of which may be optionally substituted by one or more halo atoms, $NR^6R^{66}$, $OR^6$, $C(O)OR^6$, $OC(O)R^6$ or cyano, and may contain a $CH_2$ group that is replaced by O or S; or a $C_{3-7}$cycloalkyl, heterocyclyl, $C_{1-4}$alkylene$C_{3-7}$cycloalkyl or $C_{1-4}$alkyeneheterocyclyl, any of which may be substituted with one or more substituents selected from halo, $C_{1-4}$ alkyl, $C_{1-4}$-fluoroalkyl, $OR^7$, CN, $NR^7R^{77}$, $SO_2Me$, $NO_2$ or $C(O)OR^7$.

While the preferred groups for each variable have generally been listed above separately for each variable, preferred compounds of this invention include those in which several or each variable in formula (I) is selected from the preferred, more preferred or particularly listed groups for each variable. Therefore, this invention is intended to include all combinations of preferred, more preferred and particularly listed groups.

Specific compounds of the invention which may be mentioned are those included in the Examples and pharmaceutically acceptable salts thereof.

As used herein, unless stated otherwise, "alkyl" as well as other groups having the prefix "alk" such as, for example, alkenyl, alkynyl, and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains having at least one unsaturated carbon-carbon bond.

The term "fluoroalkyl" includes alkyl groups substituted by one or more fluorine atoms, e.g. $CH_2F$, $CHF_2$ and $CF_3$.

The term "cycloalkyl" means carbocycles containing no heteroatoms, and includes monocyclic and bicyclic saturated and partially saturated carbocycles. Examples of cycloalkyl include cyclopropyl, cyclobutyl, cyclopentyl, cyclohexyl and cycloheptyl. Examples of partially saturated cycloalkyl groups include cyclohexene and indane. Cycloalkyl groups will typically contain 3 to 10 ring carbon atoms in total (e.g. 3 to 6, or 8 to 10).

The term "halo" includes fluorine, chlorine, bromine, and iodine atoms.

The term "aryl" includes phenyl and naphthyl, in particular phenyl.

Unless otherwise indicated the term "heterocyclyl" and "heterocyclic ring" includes 4- to 10-membered monocyclic and bicyclic saturated rings, e.g. 4- to 7-membered monocyclic saturated rings, containing up to three heteroatoms selected from N, O and S. Examples of heterocyclic rings include oxetane, tetrahydrofuran, tetrahydropyran, oxepane, oxocane, thietane, tetrahydrothiophene, tetrahydrothiopyran, thiepane, thiocane, azetidine, pyrrolidine, piperidine, azepane, azocane, [1,3]dioxane, oxazolidine, piperazine, and the like. Other examples of heterocyclic rings include the oxidised forms of the sulfur-containing rings. Thus, tetrahydrothiophene 1-oxide, tetrahydrothiophene 1,1-dioxide, tetrahydrothiopyran 1-oxide, and tetrahydrothiopyran 1,1-dioxide are also considered to be heterocyclic rings.

Unless otherwise stated, the term "heteroaryl" includes mono- and bicyclic 5- to 10-membered, e.g. monocyclic 5- or 6-membered, heteroaryl rings containing up to 4 heteroatoms selected from N, O and S. Examples of such heteroaryl rings are furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridinyl, pyridazinyl, pyrimidinyl, pyrazinyl and triazinyl. Bicyclic heteroaryl groups include bicyclic heteroaromatic groups where a 5- or 6-membered heteroaryl ring is fused to a phenyl or another heteroaromatic group. Examples of such bicyclic heteroaromatic rings are benzofuran, benzothiophene, indole, benzoxazole, benzothiazole, indazole, benzimidazole, benzotriazole, quinoline, isoquinoline, quinazoline, quinoxaline and purine.

Compounds described herein may contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above formula (I) is shown without a definitive stereochemistry at certain positions. The present invention includes all stereoisomers of formula (I) and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of formula (I) exists, the present invention includes any possible tautomers and pharmaceutically acceptable salts thereof, and mixtures thereof, except where specifically drawn or stated otherwise.

When the compound of formula (I) and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like.

Since the compounds of formula (I) are intended for pharmaceutical use they are preferably provided in substantially pure form, for example at least 60% pure, more suitably at least 75% pure, especially at least 98% pure (% are on a weight for weight basis).

The compounds of formula (I) can be prepared as described below, in which $E^1$, $E^2$, $E^3$, T, $G^1$, B, Q, A, x, y and D are as defined above and which are illustrated in the schemes below for compounds where $R^{11}$ is hydrogen.

Compounds of formula (I) in which Q is C(O)S can be prepared by condensing the appropriate acid (II) with a suitable thiol (III), as shown in Scheme 1, using a typical reagent for such a condensation reaction, e.g. EDCI (Pottorf, R. S.; Szeto, P. In *Handbook of Reagents for Organic Synthesis Activating Agents and Protecting Groups*; Pearson, A. J., Roush, W. R., Eds.; Wiley: Chichester, 1999; pp 186-188). The acids (II) and thiols (E) are either commercially available or are prepared easily using known techniques.

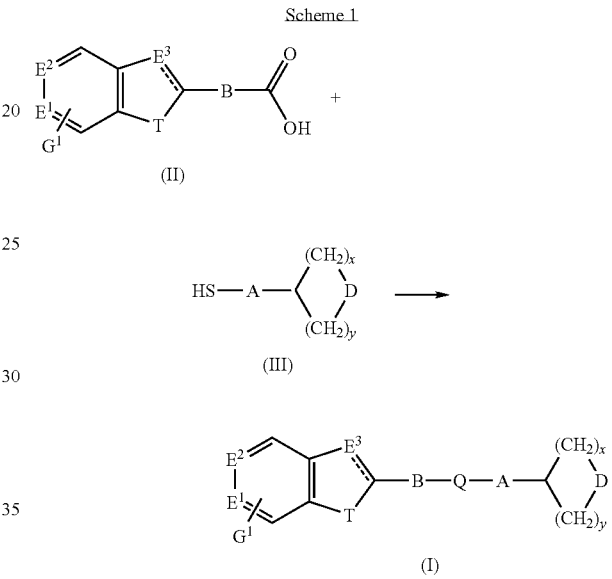

Compounds of formula (I) in which Q is a heteroaromatic ring can be made via a suitable heteroaromatic ring-forming reaction. For instance, where Q is a [1,2,4]oxadiazole ring, the compounds of formula (I) may be prepared according to the method illustrated in Scheme 2 (Hemming, K. *J. Chem. Res., Synop.* 2001, 209-216 & 601-620) wherein amidoximes of formula (I) are condensed with acids of formula (II). The acids (II) and aridoximes (IV) are either commercially available or are prepared using known techniques. The condensation initially entails activation of compounds of formula (II) by, for example, formation of the mixed anhydride, in which the acid is treated with a chloroformate, such as isobutylchloroformate, in the presence of a suitable base, such as triethylamine, in a suitable solvent, such as THF or toluene, followed by addition of compounds of formula (M). Alternatively, compounds of formula (II) may be activated by conversion to the acid halide, generated by treatment of the acid with, for example, oxalyl chloride, in a suitable solvent, such as $CH_2C_1$-DMF. The intermediates arising from the condensation of amidoximes of formula (IV) and acids of formula (II) are dissolved in an appropriate solvent, such as toluene or xylene, and heated under reflux, with concomitant removal of water by a Dean-Stark apparatus or by molecular sieves, to form oxadiazoles of formula (I). The corresponding "reversed" [1,2,4]oxadiazole may be prepared by condensing amidoxime (IVa) with an acid of formula (Ha), as illustrated in Scheme 3.

Scheme 2

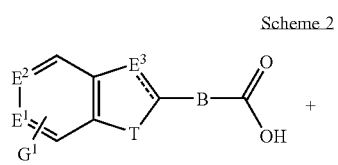

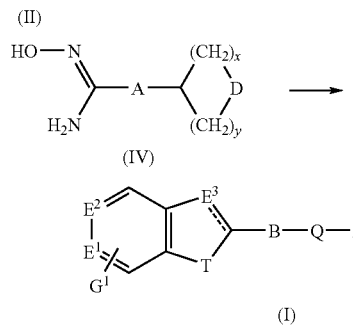

Scheme 3

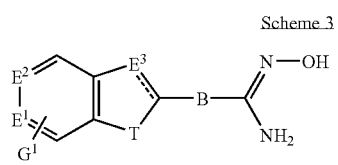

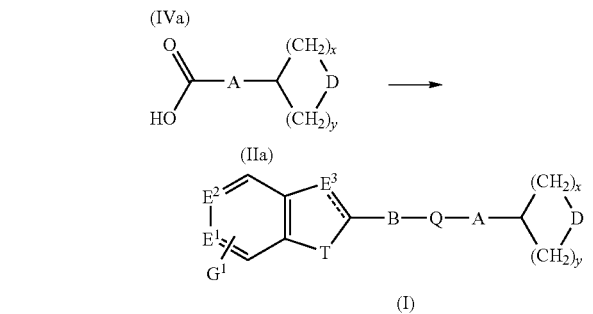

Compounds of formula (I) in which one of the CH$_2$ groups in A is replaced with O can be prepared by alkylating the appropriate alcohol (V) with the appropriate alkyl halide or sulfonate ester (VI), as shown in Scheme 4 where LG is chloro, bromo, iodo, alkanesulfonate, or arenesulfonate, and v and w are independently 0, 1, 2, 3, 4, or 5 with the proviso that v+w≦5. The reaction is typically carried out using a base, e.g., potassium tert-butoxide (Hall, S. E., et al. *J. Med. Chem.* 1989, 32, 974-984). The alcohols (V), as well as the alkyl halides or sulfonates (VI), are either commercially available or are made easily using known techniques. Alternatively, the alcohol and LG functionalities can be exchanged between the bicyclic and D-containing reactants, as shown in Scheme 5 where LG, v, and w are as described above.

Scheme 4

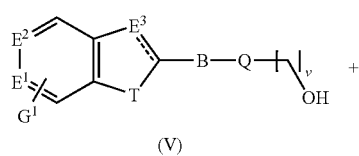

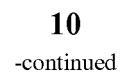

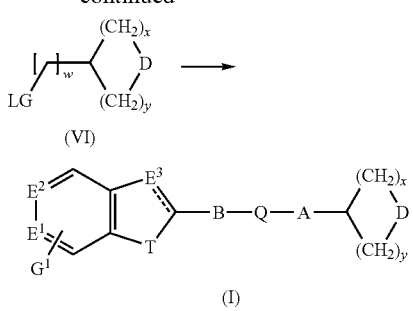

Scheme 5

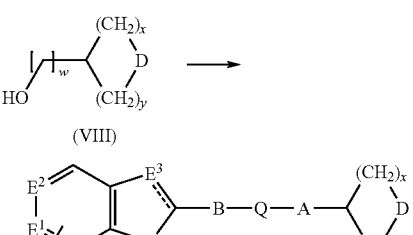

Compounds of formula (I) in which one of the CH$_2$ groups in A is replaced with NR$^3$ can be prepared by reductive alkylation of the appropriate amine (X) with the appropriate aldehyde (IX), as shown in Scheme 6 where y and z are independently 0, 1, 2, 3, or 4 with the proviso that y+z≦4. The reaction is typically carried out using a suitable reductant, e.g. sodium triacetoxyborohydride (Abdel-Magid, A. F., et al., *J. Org. Chem.* 1996, 61, 3849-3862). The aldehydes (IX), as well as the amines (X), are either commercially available or are made easily using known techniques. Alternatively, the amine and aldehyde functionalities can be exchanged between the bicyclic and D-containing reactants, as shown in Scheme 7 where y and z are as described above.

Scheme 6

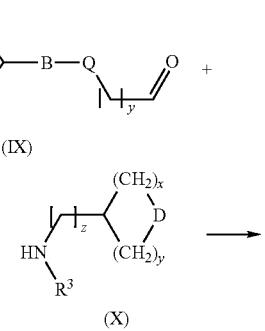

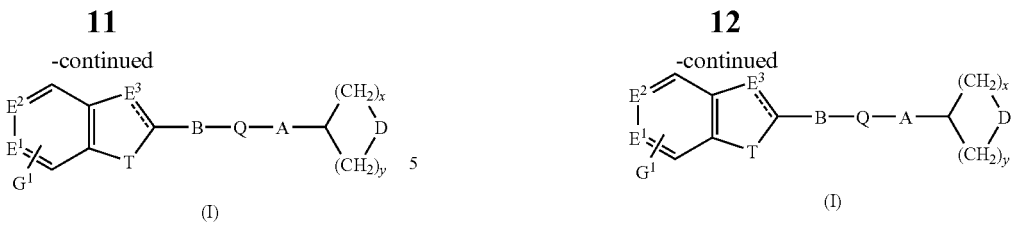

(I)

Compounds of formula (I) in which $R^1$ is $C(O)OR^5$, $C(O)R^5$, $S(O)_2R^5$, $C(O)NR^5R^{55}$, or heteroaryl may be prepared by the route shown in Scheme 9. Compounds of formula (XV), in which PG represents a suitable protecting group, for example tert-butoxycarbonyl (Boc), may be synthesised as outlined in Schemes 1-8 above. The protecting group is firstly removed under suitable conditions to afford compounds of formula (XVI). In the case of the Boc group this can be achieved by treatment of compounds of formula (XV) with a suitable acid, such as trifluoroacetic acid (Fyfe, M. C. T. et al. International Patent Publication WO 04/2031), in an appropriate solvent, such as $CH_2Cl_2$. Treatment of compounds of formula (XVI) with chloroformates Cl—$R^1$, which are generally commercially available or can be readily synthesised, in a suitable solvent, such as $CH_2Cl_2$, in the presence of a suitable base, such as triethylamine (Picard, F., et al. *J. Med. Chem.* 2002, 45, 3406-3417), affords compounds of formula (I) where $R^1$ is $C(O)OR^5$. Similarly, compounds of formula (XVI) may be reacted with sulfonyl chlorides, carboxylic acid chlorides, and carbamyl chlorides Cl—$R^1$, which are generally commercially available or can readily be synthesised, in a suitable solvent, such as $CH_2Cl_2$, in the presence of a suitable base, such as triethylamine, to afford compounds of formula (I) where $R^1$ is $S(O)_2R^5$, $C(O)R^5$, and $C(O)NR^5R^{55}$, respectively. Furthermore, compounds of formula (I) in which $R^1$ is heteroaryl may be prepared by reacting the amine (XVI) with the appropriate heteroaryl chloride or bromide under Pd(0) catalysis in the presence of a suitable ligand and base (Urgaonkar, S.; Hu, J.-H.; Verkade, J. G. *J. Org. Chem.* 2003, 68, 8416-8423). Alternatively, compounds of the formula (I) where $R^1$ is heteroaryl may be prepared by condensation of amine (XVI) with a heteroaryl chloride in the presence of base (Barillari, C. et al. *Eur. J. Org. Chem.* 2001, 4737-4741; Birch, A. M. et al. *J. Med. Chem.* 1999, 42, 3342-3355). Compounds of formula (I) in which $R^{55}$ is hydrogen may be prepared by reacting a compound of formula (XVI) with an isocyanate of formula O=C=N—$R^5$.

Scheme 7

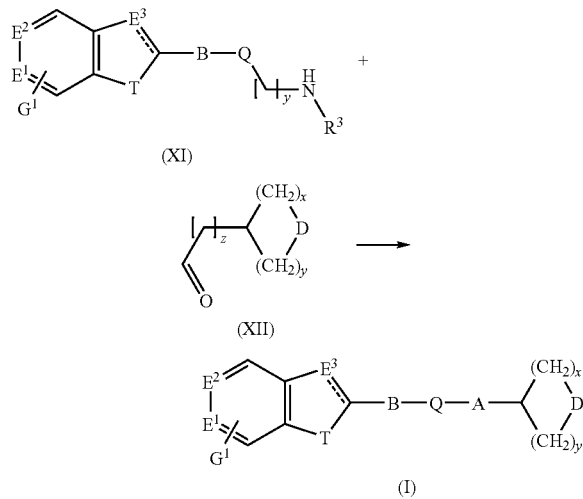

Compounds of formula (I) in which two of the $CH_2$ groups in A are replaced with CH=CH can be prepared by a Wittig reaction between the appropriate phosphonium salt (XIII) and the appropriate aldehyde (XIV), as indicated in Scheme 8 where a and b are independently 0, 1, 2, 3, or 4 with the proviso that a+b≦4. The reactions are carried out in the presence of a suitable base, e.g. NaOMe or LiHMDS (March, J. Advanced Organic Chemistry, 4th edn.; Wiley: New York 1992; pp 956-963). The phosphonium salt (XIII), as well as the aldehyde (XIV), are either commercially available or are made easily using known techniques. The compounds of formula (I) where A is $(CH_2)_n$ where n is 2, 3, 4, 5, or 6 can easily be synthesized from the abovementioned compounds of formula (I) containing a CH=CH unit by a hydrogenation reaction using, for example, palladium on charcoal as a catalyst.

Scheme 8

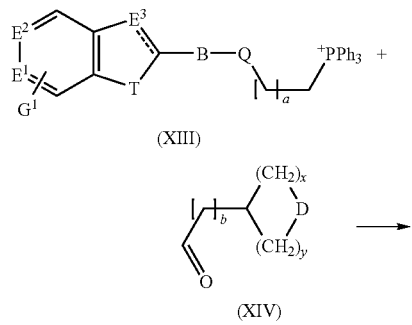

Scheme 9

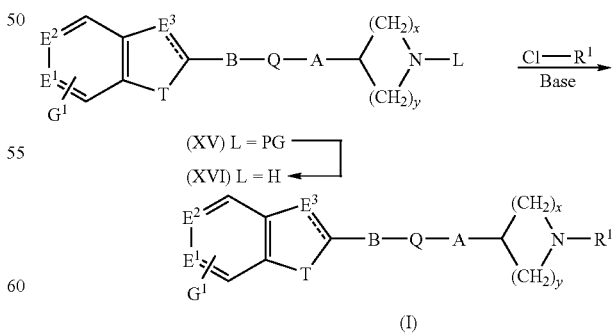

Compounds of the formula (I) where $G^1$ is CN can be prepared from the corresponding unsubstituted azine by the Reissert reaction (Fife, W. K. *J. Org. Chem.* 1983, 48, 1375-1377). Similar reactions can be used to prepare the compounds where G¹ is a halogen (Walters, M. A.; Shay, J. J. *Tetrahedron Lett.* 1995, 36, 7575-7578). The compounds where G¹ is halogen can be transformed into the corresponding compounds where G¹ is $C_{1-4}$ alkyl by transition metal-catalysed cross-coupling reactions (Fürstner, A., et al. *J. Am. Chem. Soc.* 2002, 124, 13856-13863). Alternatively, compounds where G¹ is methyl can be prepared by reacting the appropriate N-alkoxypyridinium species, prepared by alkylating the N-oxide of the corresponding unsubstituted azine, with methylmagnesium halide (Bosch, J. et al. *An. Quim.* 1975, 71, 835-837).

Other compounds of formula (I) may be prepared by methods analogous to those described above or by methods known per se.

Further details for the preparation of the compounds of formula (I) are found in the examples.

The compounds of formula (I) may be prepared singly or as compound libraries comprising at least 2, for example 5 to 1,000, compounds and more preferably 10 to 100 compounds of formula (I). Compound libraries may be prepared by a combinatorial "split and mix" approach or by multiple parallel synthesis using either solution or solid phase chemistry, using procedures known to those skilled in the art.

During the synthesis of the compounds of formula (I), labile functional groups in the intermediate compounds, e.g. hydroxy, carboxy and amino groups, may be protected. The protecting groups may be removed at any stage in the synthesis of the compounds of formula (I) or may be present on the final compound of formula (I). A comprehensive discussion of the ways in which various labile functional groups may be protected and methods for cleaving the resulting protected derivatives is given in, for example, Protective Groups in Organic Chemistry, T. W. Greene and P. G. M. Wuts, (1991) Wiley-Interscience, New York $2^{nd}$ edition.

Any novel intermediates, such as those defined above, may be of use in the synthesis of compounds of formula (I) and are therefore also included within the scope of the invention, for example compounds of formula (XVI):

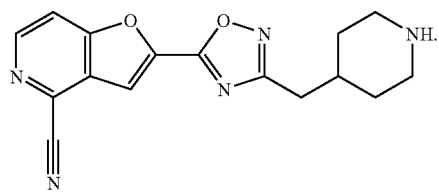

(XVI)

wherein the groups $E^1$, $E^2$, $E^3$, T, $G^1$, $R^{11}$, B, Q, A, x and y are as defined above for compounds of formula (I). Specific examples of compounds falling within the formula (XVI) include:

2-(3-Piperidin-4-ylmethyl-[1,2,4]oxadiazol-5-yl)furo[3,2-c]pyridine

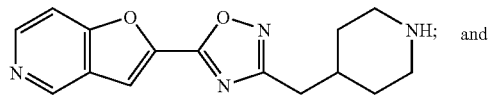 and 2-(3-Piperidin-4-ylmethyl-[1,2,4]oxadiazol-5-yl)furo[3,2-c]pyridine-4-carbonitrile

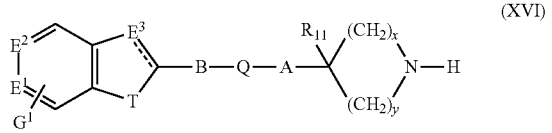

A further embodiment of the invention encompasses compounds of formula (XVI) wherein the groups $E^1$, $E^2$, $E^3$, T, $G^1$, Q and A are as defined above for compounds of formula (Ia), $R^{11}$ represents hydrogen, B represents a bond, x and y each represent 2.

As indicated above the compounds of formula (I) are useful as GPR116 agonists, e.g. for the treatment and/or prophylaxis of obesity and diabetes. For such use the compounds of formula (I) will generally be administered in the form of a pharmaceutical composition.

The invention also provides a compound of formula (I), or a pharmaceutically acceptable salt thereof, for use as a pharmaceutical.

The invention also provides a pharmaceutical composition comprising a compound of formula (I), in combination with a pharmaceutically acceptable carrier.

Preferably the composition is comprised of a pharmaceutically acceptable carrier and a non-toxic therapeutically effective amount of a compound of formula (I), or a pharmaceutically acceptable salt thereof.

Moreover, the invention also provides a pharmaceutical composition for the treatment of disease by modulating GPR116, resulting in the prophylactic or therapeutic treatment of obesity, e.g. by regulating satiety, or for the treatment of diabetes, comprising a pharmaceutically acceptable carrier and a non-toxic therapeutically effective amount of compound of formula (I), or a pharmaceutically acceptable salt thereof.

The pharmaceutical compositions may optionally comprise other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds of formula (I), or pharmaceutically acceptable salts thereof, can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous).

Thus, the pharmaceutical compositions can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound of formula (I), or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The compounds of formula (I), or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, using a compound of formula (I), or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of formula (I), or pharmaceutically acceptable salts thereof, may also be prepared in powder or liquid concentrate form.

Generally, dosage levels on the order of 0.01 mg/kg to about 150 mg/kg of body weight per day are useful in the treatment of the above-indicated conditions, or alternatively about 0.5 mg to about 7 g per patient per day. For example, obesity may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of formula (I) may be used in the treatment of diseases or conditions in which GPR116 plays a role.

Thus the invention also provides a method for the treatment of a disease or condition in which GPR116 plays a role comprising a step of administering to a subject in need thereof an effective amount of a compound of formula (I), or a pharmaceutically acceptable salt thereof. Diseases or conditions in which GPR116 plays a role include obesity and diabetes. In the context of the present application the treatment of obesity is intended to encompass the treatment of diseases or conditions such as obesity and other eating disorders associated with excessive food intake e.g. by reduction of appetite and body weight, maintenance of weight reduction and prevention of rebound and diabetes (including Type 1 and Type 2 diabetes, impaired glucose tolerance, insulin resistance and diabetic complications such as neuropathy, nephropathy, retinopathy, cataracts, cardiovascular complications and dyslipidaemia). And the treatment of patients who have an abnormal sensitivity to ingested fats leading to functional dyspepsia. The compounds of the invention may also be used for treating metabolic diseases such as metabolic syndrome (syndrome X), impaired glucose tolerance, hyperlipidemia, hypertriglyceridemia, hypercholesterolemia, low HDL levels and hypertension.

The invention also provides a method for the regulation of satiety comprising a step of administering to a subject in need thereof an effective amount of a compound of formula (I), or a pharmaceutically acceptable salt thereof.

The invention also provides a method for the treatment of obesity comprising a step of administering to a subject in need thereof an effective amount of a compound of formula (I), or a pharmaceutically acceptable salt thereof.

The invention also provides a method for the treatment of diabetes, including Type 1 and Type 2 diabetes, particularly type 2 diabetes, comprising a step of administering to a patient in need thereof an effective amount of a compound of formula (I), or a pharmaceutically acceptable salt thereof.

The invention also provides a method for the treatment of metabolic syndrome (syndrome X), impaired glucose tolerance, hyperlipidemia, hypertriglyceridemia, hypercholesterolemia, low HDL levels or hypertension comprising a step of administering to a patient in need thereof an effective amount of a compound of formula (I), or a pharmaceutically acceptable salt thereof.

The invention also provides a compound of formula (I), or a pharmaceutically acceptable salt thereof, for use in the treatment of a condition as defined above.

The invention also provides the use of a compound of formula (I), or a pharmaceutically acceptable salt thereof, in the manufacture of a medicament for the treatment of a condition as defined above.

In the methods of the invention the term "treatment" includes both therapeutic and prophylactic treatment.

The compounds of formula (I), or pharmaceutically acceptable salts thereof, may be administered alone or in combination with one or more other therapeutically active compounds. The other therapeutically active compounds may be for the treatment of the same disease or condition as the compounds of formula (I) or a different disease or condition. The therapeutically active compounds may be administered simultaneously, sequentially or separately.

The compounds of formula (I) may be administered with other active compounds for the treatment of obesity and/or diabetes, for example insulin and insulin analogs, gastric lipase inhibitors, pancreatic lipase inhibitors, sulfonyl ureas and analogs, biguanides, $\alpha_2$ agonists, glitazones, PPAR-$\gamma$ agonists, mixed PPAR-$\alpha/\gamma$ agonists, RXR agonists, fatty acid oxidation inhibitors, $\alpha$-glucosidase inhibitors, 5-agonists, phosphodiesterase inhibitors, lipid lowering agents, glycogen phosphorylase inhibitors, antiobesity agents e.g. pancreatic lipase inhibitors, MCH-1 antagonists and CB-1 antagonists (or inverse agonists), amylin antagonists, lipoxygenase inhibitors, somostatin analogs, glucokinase activators, glucagon antagonists, insulin signalling agonists, PTP1B inhibitors, gluconeogenesis inhibitors, antilypolitic agents, GSK inhibitors, galanin receptor agonists, anorectic agents, CCK receptor agonists, leptin, serotonergic/dopaminergic antiobesity drugs, reuptake inhibitors e.g. sibutramine, CRF antagonists, CRF binding proteins, thyromimetic compounds, aldose reductase inhibitors, glucocorticoid receptor antagonists, NHE-1 inhibitors or sorbitol dehydrogenase inhibitors.

Combination therapy comprising the administration of a compound of formula (I), or a pharmaceutically acceptable salt thereof, and at least one other antiobesity agent represents a further aspect of the invention.

The present invention also provides a method for the treatment of obesity in a mammal, such as a human, which method comprises administering an effective amount of a compound of formula (I), or a pharmaceutically acceptable salt thereof, and another antiobesity agent, to a mammal in need thereof.

The invention also provides the use of a compound of formula (I), or a pharmaceutically acceptable salt thereof, and another antiobesity agent for the treatment of obesity.

The invention also provides the use of a compound of formula (I), or a pharmaceutically acceptable salt thereof, in the manufacture of a medicament for use in combination with another antiobesity agent, for the treatment of obesity.

The compound of formula (I), or a pharmaceutically acceptable salt thereof, and the other antiobesity agent(s) may be co-administered or administered sequentially or separately.

Co-administration includes administration of a formulation which includes both the compound of formula (I), or a pharmaceutically acceptable salt thereof, and the other antiobesity agent(s), or the simultaneous or separate administration of different formulations of each agent. Where the pharmacological profiles of the compound of formula (I), or a pharmaceutically acceptable salt thereof, and the other antiobesity agent(s) allow it, coadministration of the two agents may be preferred.

The invention also provides the use of a compound of formula (I), or a pharmaceutically acceptable salt thereof, and another antiobesity agent in the manufacture of a medicament for the treatment of obesity.

The invention also provides a pharmaceutical composition comprising a compound of formula (I), or a pharmaceutically acceptable salt thereof, and another antiobesity agent, and a pharmaceutically acceptable carrier. The invention also encompasses the use of such compositions in the methods described above.

GPR116 agonists are of particular use in combination with centrally acting antiobesity agents.

The other antiobesity agent for use in the combination therapies according to this aspect of the invention is preferably a CB-1 modulator, e.g. a CB-1 antagonist or inverse agonist. Examples of CB-1 modulators include SR141716 (rimonabant) and SLV-319 ((4S)-(−)-3-(4-chlorophenyl)-N-methyl-N-[(4-chlorophenyl)sulfonyl]-4-phenyl-4,5-dihydro-1H-pyrazole 1-carboxamide); as well as those compounds disclosed in EP576357, EP656354, WO 03/018060, WO 03/020217, WO 03/020314, WO 03/026647, WO 03/026648, WO 03/027076, WO 03/040105, WO 03/051850, WO 03/051851, WO 03/053431, WO 03/063781, WO 03/075660, WO 03/077847, WO 03/078413, WO 03/082190, WO 03/082191, WO 03/082833, WO 03/084930, WO 03/084943, WO 03/086288, WO 03/087037, WO 03/088968, WO 04/012671, WO 04/013120, WO 04/026301, WO 04/029204, WO 04/034968, WO 04/035566, WO 04/037823 WO 04/052864, WO 04/058145, WO 04/058255, WO 04/060870, WO 04/060888, WO 04/069837, WO 04/069837, WO 04/072076, WO 04/072077, WO 04/078261 and WO 04/108728, and the references disclosed therein.

Other diseases or conditions in which GPR116 has been suggested to play a role include those described in WO 00/50562 and U.S. Pat. No. 6,468,756, for example cardiovascular disorders, hypertension, respiratory disorders, gestational abnormalities, gastrointestinal disorders, immune disorders, musculoskeletal disorders, depression, phobias, anxiety, mood disorders and Alzheimer's disease.

All publications, including, but not limited to, patents and patent application cited in this specification, are herein incorporated by reference as if each individual publication were specifically and individually indicated to be incorporated by reference herein as fully set forth.

The invention will now be described by reference to the following examples which are for illustrative purposes and are not to be construed as a limitation of the scope of the present invention.

EXAMPLES

Materials and Methods

Column chromatography was carried out on $SiO_2$ (40-63 mesh) unless specified otherwise. LCMS data for all Preparations and Examples 1-124 were obtained as follows: Atlantis 3μ $C_{18}$ column (3.0×20.0 mm, flow rate=0.85 mL/min) eluting with a $H_2O$—$CH_3CN$ solution, containing 0.1% $HCO_2H$, over 6 min with UV detection at 220 nm. Gradient information: 0.0-0.3 min 100% $H_2O$; 0.3-4.25 min: Ramp up to 10% $H_2O$-90% $CH_3CN$; 4.25-4.4 min: Ramp up to 100% $CH_3CN$; 4.4-4.9 min: Hold at 100% $CH_3CN$; 4.9-6.0 min: Return to 100% $H_2O$. The mass spectra were obtained using an electrospray ionisation source in either the positive ($ES^+$) or negative ($ES^-$) ion modes. LCMS data for Examples 125-149 were obtained as follows: Waters Xterra MS C18, 5 μm (19×50 mm, flow rate 25 mL/min) eluting with a $H_2O$-MeCN gradient containing 0.1% v/v $NH_3$ over 10 min with UV detection at 215 and 254 nm. Gradient information: 0.0-0.5 min Hold at 95% $H_2O$-5% MeCN; 0.5-7.5 min: Ramp from 95% $H_2O$-5% MeCN to 5% $H_2O$-95% MeCN; 7.5-8.4 min: Hold at 5% $H_2O$-95% MeCN; 8.4-8.5 min: Return to 95% $H_2O$-5% MeCN; 8.5-10.0 min: Hold at 95% $H_2O$-5% MeCN. Mass spectra were obtained using an electrospray ionisation source in either the positive ($ES^+$) or negative ($ES^-$) ion modes. An LC-packings Acurate flow splitter was used to split the column eluent 1000:1, make-up flow comprised MeCN containing 0.1% formic acid at 1 ml/min.

Abbreviations and acronyms: Ac: Acetyl; tBDMS: tert-butyldimethylsilyl; Bn: Benzyl; t-Bu: tert-Butyl; Bz: Benzoyl; 18C6: [18]Crown-6; DABCO: Bicyclo(2,2,2)-1,4-diazaoctane; DBU: 1,8-Diazabicyclo[5.4.0]undec-7-ene; DIPEA: N,N-Diisopropylethylamine; DMAP: 4-Dimethylaminopyridine; DMF: N,N-Dimethylformamide; DMSO: Dimethylsulfoxide; EDCI: 1-(3-Dimethylaminopropyl)-3-ethylcarbodiimide hydrochloride; Et: Ethyl; i-Bu: Isobutyl; IH: Isohexane; i-Pr: Isopropyl; LiHMDS: Lithium bis(trimethylsilyl)amide; mCPBA: 3-Chloroperoxybenzoic acid; Me: Methyl; Ms: Methanesulfonyl; Ph: Phenyl; n-Pr: n-Propyl; RP-HPLC: Reverse phase-high performance liquid chromatography; RT: Retention time; TFA: Trifluoroacetic acid-; THF: Tetrahydrofuran; TMS: Trimethylsilyl. The syntheses of the following compounds have been described elsewhere: (1-tert-Butoxycarbonylpiperidin-4-ylmethyl)triphenylphosphonium iodide: Hale, J. J., et al. U.S. Patent Application 20020094989; 4-Carboxymethoxypiperidine-1-carboxylic acid tert-butyl ester: Brewster, A. G., et al. U.S. Pat. No. 5,981,531; (3R)-3-Carboxymethoxy-pyrrolidine-1-carboxylic acid tert-butyl ester: Alig, L., et al. EP656348; 7,8-Dihydro-6-isoquinolinecarboxylic acid. Chan, L., et al. *Bioorg. Med. Chem. Lett.* 2000, 10, 1477-1480; Furo[2,3-c]pyridine-2-carbaldehyde, Furo[3,2-c]pyridine-2-carbaldehyde, Furo[3,2-c]pyridine-2-carbonitrile, Furo[2,3-c]pyridine-2-carboxylic acid, and Furo[3,2-c]pyridine-2-carboxylic acid: Morita, H.; Shiotani, S. *J. Heterocycl. Chem.* 1987, 24, 373-376; (N-Hydroxycarbamimidoylmethyl)carbamic acid tert-butyl ester: WO03/082861; 4-(N-Hydroxycarbamimidoylmethyl)piperidine-1-carboxylic acid tert-butyl ester and 4-(N-Hydroxycarbamimidoyl)piperidine-1-carboxylic acid tert-butyl ester: Sørensen, J. L.; Andersen, K. E.; Petterson, I. WO 04/054973; 3-Hydroxy-furo[3,2-c]pyridine-2-carboxylic acid ethyl ester: Shiotani, S., et al. *J Heterocycl. Chem.* 1988, 25, 1205-1213; 7-Iodo-furo[3,2-c]pyridine-2-carbaldehyde: Tata, J. R., et al. WO 01/038332; 4-Mercaptopiperidine-1-carboxylic acid tert-butyl ester: Bru-Magniez, N., et al. U.S. Pat. No. 5,317,025; 4-(2-Methanesulfonyloxyethyl)piperidine-1-carboxylic acid tert-butyl ester: Cain, G. A., et al. U.S. Pat. No. 5,252,586; 1-Methyl-1-cyclopropanol: Kulinkovich, O. G., et al. *Synthesis* 1991, 234; [1,7]Naphthyridine-3-carboxylic acid: Chan, L., et al. *Bioorg. Med. Chem. Leu.* 1999, 9, 2583-2586; Oxazolo[4,5-c]pyridine: Katner, A. S.; Brown, R. F. *J. Heterocycl. Chem.* 1990, 27, 563-566; 1H-Pyrrolo[2,3-c]pyridine-2-carboxylic acid and 1H-Pyrrolo[2,3-c]pyridine-2-carboxylic acid ethyl ester: Fisher, M. H.; Matzuk, A. R. *J. Heterocycl. Chem.* 1969, 6, 775-776; Thieno[2,3-c]pyridine-2-carboxylic acid and Thieno[3,2-c]pyridine-2-carboxylic acid: Walker, D. P., et al. WO 03/029252. All other starting materials were available from commercial sources.

Preparation 1

6-Chloro-1H-pyrrolo[3,2-c]pyridine-2-carboxylic acid

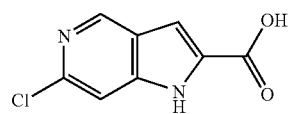

$AgSO_4$ (7.1 g, 22.8 mmol) and 4-amino-2-chloropyridine (4.1 g, 31.6 mmol) were added to a solution of 12 (5.7 g, 22.3 mmol) in EtOH (100 mL), then the mixture was stirred at 20° C. for 72 h. The bright yellow suspension was filtered, washed with MeOH, and the combined filtrates concentrated in vacuo. The residue was partitioned between saturated aqueous $Na_2CO_3$ (200 mL) and EtOAc (200 mL). The organic layer was washed with 25% aqueous $Na_2S_2O_3$ (50 mL) and brine (50 mL), before being dried ($MgSO_4$). Filtration, solvent evaporation, and purification by column chromatography (IH-EtOAc, 3:1 to 2.5:1) provided 2-chloro-5-iodopyridin-4-ylamine: $\delta_H$($CDCl_3$): 4.81 (brs, 2H), 6.63 (s, 1H), 8.38 (s, 1H). Pyruvic acid (0.86 mL, 12.4 mmol) was added to a solution of this compound (1.05 g, 4.1 mmol), $Pd(OAc)_2$ (56 mg, 0.25 mmol) and DABCO (1.39 g, 12.4 mmol) in anhydrous DMF (30 mL). The reaction mixture was degassed with Ar for 20 min, before being heated to 145° C. for 2 h. The solvent was removed in vacuo, then the residue was taken up in water (200 mL). The pH was adjusted to 9-10 with 1 M NaOH, then the mixture was filtered through Celite. The filtrate was washed with EtOAc (50 mL) and $Et_2O$ (50 mL), then the pH was adjusted to 3 with 1 M HCl. Extraction with EtOAc (5×50 mL), drying of the combined extracts ($MgSO_4$), filtration, and concentration gave the title compound: $\delta_H$(($CD_3$)$_2$SO): 7.24 (s, 1H), 7.42 (s, 1H), 8.80 (s, 1H).

Preparation 2

5-Chloro-1H-pyrrolo[2,3-c]pyridine-2-carboxylic acid

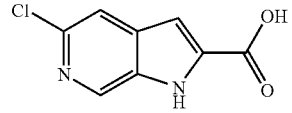

A solution of KOEt (1.5 g, 17.4 mmol) in Et$_2$O (80 mL) and ETOH (10 mL) under Ar was treated with (CO$_2$Et)$_2$ (2.4 mL, 17.4 mmol), then the mixture was stirred at 20° C. for 0.5 h. A solution of 2-chloro-4-methyl-5-nitropyridine (3.0 g, 17.4 mmol) in Et$_2$O (20 mL) was added, then the mixture was stirred at 20° C. for 15 h. On cooling to 0° C., the dark green solid produced was collected and washed with cold Et$_2$O. This solid was dissolved in H$_2$O (200 mL), then the solution was acidified to pH 4 with AcOH to afford an orange precipitate, which was collected by filtration and dried to give 3-(2-chloro-5-nitropyridin-4-yl)-2-oxopropionic acid ethyl ester: m/z (ES$^+$)=273 [M+H]$^+$. This compound (3.0 g, 11.0 mmol) was dissolved in ETOH (100 mL) and THF (50 mL). Fe powder (3.7 g, 66.0 mmol) and saturated aqueous NH$_4$Cl (50 mL) were added, then the mixture was heated under reflux for 2 h. The mixture was cooled, filtered through celite, and extracted several times with EtOAc. The organic layers were combined, washed with brine (100 mL), dried (MgSO$_4$), and concentrated in vacuo to give 5-chloro-1H-pyrrolo[2,3-c]pyridine-2-carboxylic acid ethyl ester: $\delta_H$ (CD$_3$OD): 1.42 (t, 3H), 4.44 (q, 2H), 7.15 (s, 1H), 7.70 (s, 1H), 8.59 (s, 1H). A solution of this ester (1.8 g, 7.9 mmol) in EtOH (70 mL) was treated with 2 M NaOH (5.2 mL, 10.4 mmol), then the mixture was heated under reflux for 2 h. The solvents were removed in vacuo and the residual solid dissolved in H$_2$O (150 mL). The solution was acidified to pH 4 with AcOH to give the title compound as a brown solid that was isolated by filtration: $\delta_H$ (CD$_3$OD): 7.13 (s, 1H), 7.68 (s, 1H), 8.58 (s, 1H).

Preparation 3

4-Mercaptomethylpiperidine-1-carboxylic acid tert-butyl ester

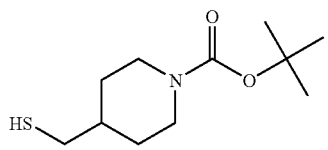

A stirred solution of N-tert-butoxycarbonyl-4-(4-toluenesulfonyloxymethyl)piperidine (240 mg, 0.65 mmol) and thiourea (99 mg, 1.30 mmol) in EtOH (1 mL) was heated under gentle reflux for 16 h. The solvent was evaporated off under reduced pressure to furnish the tosylate salt of 4-carbamimidoylsulfanylmethylpiperidine-1-carboxylic acid tert-butyl ester: m/z (ES$^+$)=274.0 [M+H]$^+$. A solution of this salt (250 mg, 0.56 mmol) in H$_2$O (1 mL) and concentrated aqueous NH$_3$ (2 mL) was heated to 100° C. with stirring for 20 min. On cooling, the mixture was partitioned between Et$_2$O (30 mL) and H$_2$O (10 mL), the pH of the aqueous phase being adjusted to 7 using 2 M HCl and saturated aqueous NaHCO$_3$. The organic phase was extracted with 1 M NaOH (15 mL), then the aqueous extracts were neutralised to pH 7 with 2 M HCl. The cloudy mixture was extracted with Et$_2$O (50 mL), then the organic extracts were washed with brine (10 mL) and dried (MgSO$_4$). Filtration and solvent evaporation finished the title compound: $\delta_H$ (CDCl$_3$): 1.05-1.20 (m, 2H), 1.35 (t, 1H), 1.48 (s, 9H), 1.50-1.60 (m, 1H), 1.80-1.90 (m, 2H), 2.40-2.50 (m, 2H), 2.60-2.80 (m, 2H), 4.05-4.25 (m, 2H).

Preparation 4

Furo[3,2-c]pyridin-2-ylmethanol

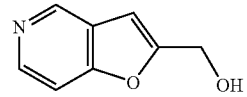

NaBH$_4$ (0.26 g, 6.8 mmol) was added to a stirred solution of furo[3,2-c]pyridine-2-carbaldehyde (2.00 g, 13.6 mmol) in anhydrous MeOH (25 mL) at 0° C. After 1.5 h, the reaction was quenched with H$_2$O (20 mL), before being extracted with CH$_2$Cl$_2$ (3×30 mL). The combined organic extracts were dried (MgSO$_4$), filtered, and concentrated to provide the title compound: m/z (ES$^+$)=150.0 [M+H]$^+$.

Preparation 5

2-Bromomethylfuro[3,2-c]pyridine hydrochloride

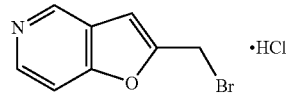

A stirred suspension of furo[3,2-c]pyridin-2-ylmethanol (Preparation 4, 1.47 g, 9.9 mmol) in anhydrous CH$_2$Cl$_2$ (60 mL) was treated with CBr$_4$ (4.90 g, 14.8 mmol). The mixture was cooled down to 0° C., before being treated with PPh$_3$ (3.88 g, 14.8 mmol). After 2 h at 20° C., the reaction was filtered, then the filtrate was diluted with CH$_2$Cl$_2$ (50 mL), before being washed with saturated aqueous NaHCO$_3$ (2×50 mL) and H$_2$O (50 mL). The CH$_2$Cl$_2$ solution was extracted with 2 M HCl (3×50 mL), then the combined HCl extracts were evaporated to furnish the title compound: m/z (ES$^+$)=211.9, 213.9 [M+H]$^+$.

Preparation 6

Furo[3,2-c]pyridin-2-ylmethyltriphenylphosphonium bromide hydrochloride

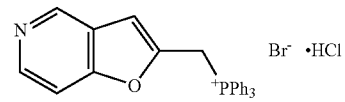

A solution of 2-bromomethylfuro[3,2-c]pyridine hydrochloride (Preparation 5, 2.12 g, 8.5 mmol) and PPh$_3$ (2.24 g, 8.5 mmol) in anhydrous THF-EtOH (1:1, 80 mL) was heated under reflux for 3 d. The solvents were removed under reduced pressure, then the residual solid was triturated with hot THF to furnish the title compound: RT=2.32 min.

Preparation 7

4-(2-Hydroxy-2-oxazolo[4,5-c]pyridin-2-ylethyl)piperidine-1-carboxylic acid tert-butyl ester

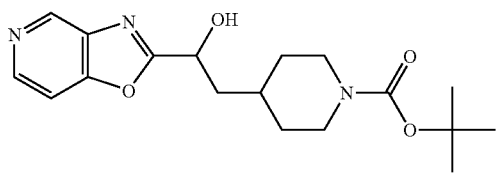

i-PrMgCl (0.44 mL of a 2 mmol/mL solution in THF, 0.88 mmol) was added dropwise to a stirred solution of oxazolo[4,5-c]pyridine (105 mg, 0.87 mmol) in anhydrous THF (3 mL) at 0° C. After 1 h, a solution of 4-(2-oxo-ethyl)piperidine-1-carboxylic acid tert-butyl ester (198 mg, 0.87 mmol) in anhydrous THF (2 mL) was added, then the mixture was allowed to warm to 20° C. over 16 h, before being quenched with saturated aqueous NH$_4$Cl (10 mL). The layers were separated, then the aqueous phase was extracted with EtOAc (3×15 mL). The combined organic extracts were dried (MgSO$_4$), filtered, and concentrated in vacuo. Flash chromatography (EtOAc) of the residue furnished the title compound: m/z (ES$^+$)=348.1 [M+H]$^+$.

Preparation 8

4-{5-[4-(tert-Butyl-methylsilanyloxymethyl)furo[3,2-c]pyridine-2-yl]-[1,2,4]oxadiazole-3-ylmethoxy}piperidine-1-carboxylic acid tert-butyl ester

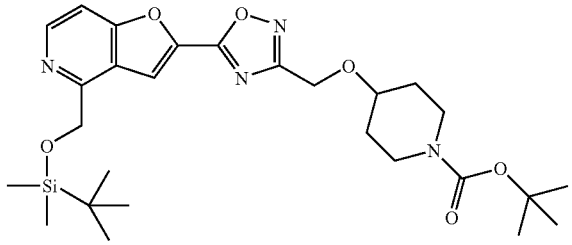

(COCl)$_2$ (2.5 mL) was added dropwise to a stirred suspension of furo[3,2-c]pyridine-2-carboxylic acid (1.64 g, 10.1 mmol) in anhydrous CH$_2$Cl$_2$ (40 mL). After effervescence had ceased, the mixture was concentrated. Further CH$_2$Cl$_2$ (20 mL) was added, followed by NEt$_3$ (4 mL) and MeOH (20 mL). After 1 h stirring, the mixture was diluted with EtOAc (50 mL) and washed with H$_2$O, saturated aqueous NaHCO$_3$ and brine. The CH$_2$Cl$_2$ solution was dried (MgSO$_4$), filtered, and concentrated to afford furo[3,2-c]pyridine-2-carboxylic acid methyl ester: δ$_H$(CDCl$_3$): 3.96 (s, 3H), 7.48 (d, 1H), 7.54 (s, 1H), 8.59 (d, 1H), 9.00 (s, 1H). A solution of this compound (1.10 g, 6.2 mmol) in MeOH was treated with TFA (0.5 mL). The flask was purged with argon, Bz$_2$O$_2$ (1.50 g, 6.2 mmol) added, and the mixture heated to reflux for 8 h. The mixture was cooled, adsorbed onto silica and purified via column chromatography to furnish 4-hydroxymethylfuro[3,2-c]pyridine-2-carboxylic acid methyl ester: m/z (ES$^+$)=208.0 [M+H]$^+$. A solution of this alcohol (0.50 g, 2.4 mmol), tBDMS-Cl (0.47 g, 3.1 mmol), NEt$_3$ (0.5 mL, 3.6 mmol) and DMAP (catalytic) was stirred in THF overnight. The solution was diluted with EtOAc and washed with H$_2$O and brine, before being dried and concentrated. Purification via chromatography afforded 4-(tert-butylmethylsilanyloxymethyl)furo[3,2-c]pyridine-2-carboxylic acid methyl ester: δ$_H$(CDCl$_3$) 0.01 (s, 6H), 0.82 (s, 9H), 3.86 (s, 3H), 4.99 (s, 2H), 7.28 (d, 1H), 7.87 (s, 1H), 8.38 (d, 1H). To a solution of 4-(N-hydroxycarbamimidoylmethoxy)-piperidine-1-carboxylic acid tert-butyl ester (Preparation 9, 93 mg, 340 μmol) in THF was added NaH (60% dispersion in mineral oil, 14 mg, 350 μmol). After effervescence had ceased, 4-(tert-butyl-methylsilanyloxymethyl)furo[3,2-c]pyridine-2-carboxylic acid methyl ester (100 mg, 311 μmol) was added. After 3 h at 20° C., the reaction was heated to reflux for 50 min. The mixture was cooled, diluted with EtOAc, washed with saturated aqueous NH$_4$Cl, and brine, before being dried and concentrated. Purification via column chromatography afforded the title compound: m/z (ES$^+$)=545.1 [M+H]$^+$.

Preparation 9

4-(N-Hydroxycarbamimidoylmethoxy)piperidine-1-carboxylic acid tert-butyl ester

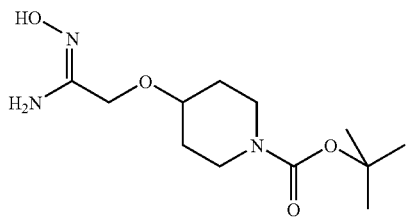

A solution of 4-carboxymethoxy)piperidine-1-carboxylic acid tert-butyl ester (14.13 g, 54.7 mmol) and NEt$_3$ (7.7 mL, 65.6 mmol) in anhydrous THF (250 mL) was cooled to 0° C., before being treated dropwise with isobutyl chloroformate (8.5 mL, 65.6 mmol). After stirring at 0° C. for 30 min, the reaction mixture was cooled to −20° C., before being added rapidly, via cannula, to a solution of NH$_3$ in anhydrous CH$_2$Cl$_2$ (0.7 M, 250 mL, 175 mmol) at −70° C. The reaction was allowed to warm to 20° C., before being stirred for 1 h. The mixture was diluted with CH$_2$Cl$_2$ (250 mL), before being washed with saturated aqueous NaHCO$_3$ (200 mL), 0.5 M HCl (200 mL), and brine (200 mL). After drying (MgSO$_4$), the solution was filtered and the solvent evaporated to give a residue that was purified by flash chromatography (IH-THF, 3:7) to afford 4-carbamoylmethoxypiperidine-1-carboxylic acid tert-butyl ester: δ$_H$(CDCl$_3$): 1.49 (s, 9H), 1.53-1.60 (m, 2H), 1.85-1.92 (m, 2H), 3.11 (m, 2H), 3.58 (m, 1H), 3.76-3.83 (m, 2H), 3.98 (s, 2H), 6.19 (brs, 1H), 6.56 (brs, 1H). A solution of this compound (235 mg, 0.91 mmol) and NEt$_3$ (140 μL, 1.00 mmol) in anhydrous CH$_2$Cl$_2$ (5 mL) was cooled to 0° C., then a solution of trichloroacetyl chloride (174 mg, 0.96 mmol) in anhydrous CH$_2$Cl$_2$ (5 mL) was added dropwise. The reaction mixture was stirred at 20° C. for 1 h, then the solvent was removed and the residue purified by flash chromatography (IH-EtOAc, 1:1) to furnish 4-cyanomethoxypiperidine-1-carboxylic acid tert-butyl ester: δ$_H$ (CDCl$_3$): 1.50 (s, 9H), 1.58-1.65 (m, 2H), 1.89-1.95 (m, 2H), 3.20 (m, 2H), 3.74-3.79 (m, 3H), 4.33 (s, 2H). A solution of K$_2$CO$_3$ (119 mg, 0.86 mmol) and NH$_2$OH.HCl (119 mg, 1.71 mmol) in H$_2$O (0.5 mL) was added to the above nitrile (206 mg, 0.86 mmol) in EtOH (2 mL). The mixture was heated at 75° C. for 45 min, before being cooled to ambient temperature. The solvents were evaporated, then the residue was diluted with EtOAc (50 mL), before being washed with H$_2$O (2×10 mL) and brine (10 mL). The EtOAc solution was dried MgSO$_4$), filtered, and concentrated to afford the title compound: m/z (ES$^+$)=274.0 [M+H]$^+$.

Preparation 10

1-Methyl-1H-pyrrolo[2,3-c]pyridine-2-carboxylic acid

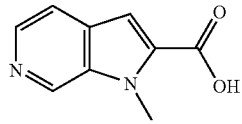

NaH (60% dispersion in mineral oil, 51 mg, 1.26 mmol) was added to a solution of 1H-pyrrolo[2,3-c]pyridine-2-carboxylic acid ethyl ester (200 mg, 1.05 mmol) in anhydrous DMF (10 mL) at 0° C. The mixture was stirred for 1 h, before being treated with MeI (79 µL, 1.26 mmol) and allowed to warm to 20° C. After 16 h, saturated aqueous NH$_4$Cl (10 mL) was added, then the suspension was stirred vigorously for 1 h. The mixture was partitioned between H$_2$O (10 mL) and EtOAc (30 mL), then the aqueous layer was extracted with EtOAc (3×20 mL). The combined organic extracts were washed with brine (20 mL), dried (MgSO$_4$), filtered, and concentrated, then the residue was purified by flash chromatography (IH-EtOAc, 1:1) to provide 1-methyl-1H-pyrrolo[2,3-c]pyridine-2-carboxylic acid ethyl ester: δ$_H$ (CDCl$_3$): 1.45 (t, 3H), 4.20 (s, 3H), 4.42 (q, 2H), 7.25 (s, 1H), 7.58 (d, 1H), 8.36 (d, 1H), 8.95 (s, 1H). A solution of this ester (36 mg, 180 µmol) in EtOH (3 mL) was treated with 2 M NaOH (270 µL, 540 µmol), then the mixture was stirred at 60° C. for 4 h. On cooling to ambient temperature, the mixture was treated dropwise with dilute AcOH to adjust the pH to 4. The resulting suspension was allowed to stand at ambient temperature for 7 d, then the precipitated solid was collected, washed with H$_2$O, and dried to furnish the title compound: δ$_H$(CD$_3$OD): 4.23 (s, 3H), 7.20 (s, 1H), 8.01 (d, 1H), 8.17 (d, 1H), 9.12 (s, 1H).

Preparation 11

N-Hydroxyfuro[3,2-c]pyridine-2-carboxamidine

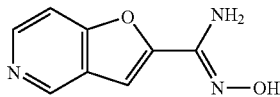

A solution of NH$_2$OH.HCl (1.22 g, 17.5 mmol) and K$_2$CO$_3$ (1.21 g, 8.75 mmol) in H$_2$O (3 mL) was added to a stirred solution of furo[3,2-c]pyridine-2-carbonitrile (1.26 g, 8.75 mmol) in EtOH (6 mL). The reaction was heated to 70° C. for 2 h, before being concentrated in vacuo. The remainder was partitioned between EtOAc and H$_2$O. The aqueous phase was extracted with EtOAc (8×), then the combined organic extracts were washed with brine, back-extracting with EtOAc (4×). The combined organic extracts were dried (MgSO$_4$), filtered, and concentrated to give the title compound: m/z (ES$^+$)=178.0 [M+H]$^+$.

Preparation 12

2-(3-Piperidin-4-ylmethyl-[1,2,4]oxadiazol-5-yl)furo[3,2-c]pyridine

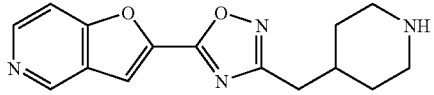

TFA (10 mL) was added to a stirred solution of 4-(5-furo[3,2-c]pyridin-2-yl-[1,2,4]oxadiazol-3-ylmethyl)piperidine-1-carboxylic acid tert-butyl ester (Example 44, 1.76 g, 4.56 mmol) in anhydrous CH$_2$Cl$_2$ (20 mL). After 1 h, the solvents were removed under reduced pressure. The residue was taken up in CH$_2$Cl-MeOH (9:1, 100 mL), before being washed with 2M NaOH (100 mL). The aqueous phase was extracted with CH$_2$Cl$_2$-MeOH (9:1, 2×100 mL), then the organic extracts were combined, dried (MgSO$_4$), and concentrated to furnish the title compound: m/z (ES$^+$)=285.0 [M+H]$^+$.

Preparation 13

C-(3-Furo[3,2-c]pyridin-2-yl-[1,2,4]oxadiazol-5-yl)methylamine

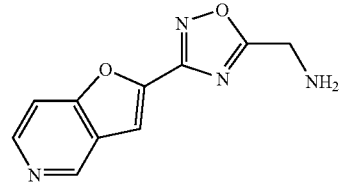

NEt$_3$ (0.38 mL, 2.71 mmol) was added to a stirred solution of N-tert-butoxycarbonylglycine (475 mg, 2.71 mmol) in anhydrous THF (30 mL). The mixture was cooled to 0° C., before being treated with i-BuOCOCl (0.35 mL, 2.71 mmol). After 5 min, the reaction was allowed to warm to ambient temperature, before being stirred for 45 min and then treated with N-hydroxyfuro[3,2-c]pyridine-2-carboxamidine (Preparation 11, 400 mg, 2.26 mmol). After 3 h, the mixture was treated with saturated aqueous NaHCO$_3$, H$_2$O, and Et$_2$O. The organic phase was washed with brine, before being dried (MgSO$_4$). Filtration, solvent evaporation, and column chromatography (MeOH—CH$_2$Cl$_2$, 1:49 to 3:47) furnished the acylated amidoxime: m/z (S$^+$)=335.1 [M+H]$^+$. A solution of this compound (420 mg, 0.82 mmol) in PhMe (70 mL) was heated under reflux with stirring for 16 h. The solvents were then removed in vacuo, and the residue was purified by column chromatography (MeOH—CH$_2$Cl$_2$, 1:49) to yield (3-furo[3,2-c]pyridin-2-yl-[1,2,4]oxadiazol-5-ylmethyl)carbamic acid tert-butyl ester: m/z (ES$^+$)=317.1 [M+H]$^+$. TFA (2.6 mL) and H$_2$O (11 µL) was added to a stirred mixture of this carbamate ester (195 mg, 0.62 mmol) in CH$_2$Cl$_2$ (10 mL). After 1 h, the solvents were removed in vacuo, then excess TFA was removed by azeotroping with PhMe (2×). The remainder was partitioned between CH₂Cl₂-MeOH (9:1) and 2 M NaOH. The aqueous phase was further extracted with CH₂Cl₂-MeOH (9:1, 10×), then the combined organic extracts were washed with brine, before being dried (MgSO₄). Filtration and solvent evaporation furnished the title compound: m/z (ES⁺)=217.0 [M+H]⁺.

Preparation 14

C-(5-Furo[3,2-c]pyridin-2-yl-[1,2,4]oxadiazol-3-yl) methylamine

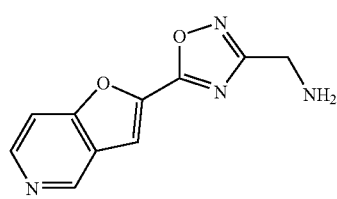

(COCl)₂ (2.5 mL, 24.5 mmol) was added to a stirred suspension of furo[3,2-c]pyridine-2-carboxylic acid (2.00 g, 12.2 mmol) in anhydrous CH₂Cl₂ (10 mL). The mixture was treated with one drop of anhydrous DMF, before being heated under reflux for 4 h. On cooling, the solvent was evaporated to furnish the crude acid chloride, which was dissolved in anhydrous CH₂Cl₂ (30 mL). The stirred solution was cooled down to 0° C., before being treated with NEt₃ (3 mL). After 5 min, (N-hydroxycarbamimidoylmethyl)carbamic acid tert-butyl ester (2.29 g, 12.2 mmol) was added, then the mixture was stirred at 20° C. overnight. The solvent was removed in vacuo, then the residue was dissolved in PhMe, before being heated under reflux for 16 h. Column chromatography yielded (5-furo[3,2-c]pyridin-2-yl-[1,2,4]oxadiazol-3-ylmethyl)-carbamic acid tert-butyl ester: m/z (ES⁺)=317.1 [M+H]⁺. TFA (15 mL) was added to a stirred solution of this compound (1.13 g, 3.5 mmol) in CH₂Cl₂ (25 mL) at 0° C. After 3 h, PhMe was added, and the solvent was evaporated off under reduced pressure. The remainder was partitioned between CH₂Cl₂ and saturated aqueous NaHCO₃, then the CH₂Cl₂ extracts were dried (MgSO₄) and evaporated to furnish the title compound.

Preparation 15

2-(3-Piperidin-4-ylmethyl-[1,2,4]oxadiazol-5-yl)furo [3,2-c]pyridine-4-carbonitrile

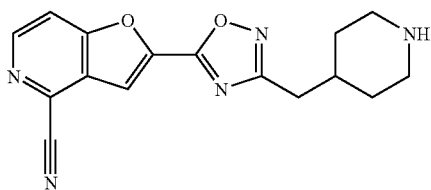

A stirred solution 4-[5-(4-cyanofuro[3,2-c]pyridin-2-yl)-[1,2,4]oxadiazol-3-ylmethyl]-piperidine-1-carboxylic acid tert-butyl ester (Example 82, 134 mg, 328 μmol) in anhydrous CHCl₃ (7 mL) was treated with TMS-I (140 μL, 983 μmol). After 1 h, the reaction was treated with MeOH (3.4 mL), then solid Na₂S₂O₃ was added slowly to remove the yellow colour. The reaction mixture was filtered and the excess Na₂S₂O₃ collected was washed with MeOH (3×1 mL). The combined filtrates were allowed to stand for 1 h, before being purified by column chromatography (MeOH—CH₂Cl₂, 1:9) to yield the title compound: RT=2.44 min; m/z (ES⁺)=310.1 [M+H]⁺.

Preparation 16

3-Benzyloxyfuro[3,2-c]pyridine-2-carboxylic acid ethyl ester

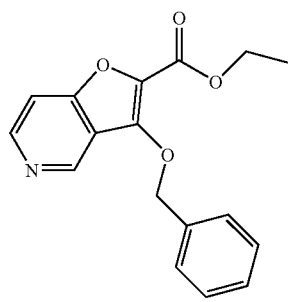

K₂CO₃ (2.34 g, 17.0 mmol) was added to a stirred solution of 3-hydroxyfuro[3,2-c]pyridine-2-carboxylic acid ethyl ester (1.76 g, 8.5 mmol) in DMF (40 mL). After 5 min, BnBr (1.25 mL, 10.6 mmol) was added, then the mixture was stirred for 16 h, before being poured into H₂O and extracted with EtOAc (3×). The combined organic extracts were washed with brine, before being dried (MgSO₄). Filtration, solvent evaporation, and column chromatography (EtOAc) yielded the title compound: m/z (ES⁺)=298.0 [M+H]⁺.

Preparation 17

3-Carboxymethoxyazetidine-1-carboxylic acid tert-butyl ester

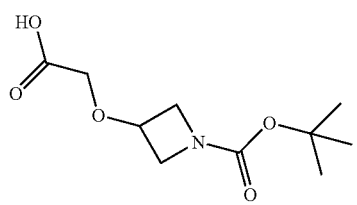

Anhydrous DMF (5 mL) was added slowly to a stirred mixture of 3-hydroxyazetidine-1-carboxylic acid tert-butyl ester (350 mg, 2.0 mmol) and NaH (121 mg of a 60% dispersion in mineral oil, 3.0 mmol) at 0° C. After 15 min, ICH₂CO₂Na (630 mg, 3.0 mmol) was added, then stirring was continued at 20° C. for 65 h. The solvent was removed in vacuo, then the residue was partitioned between H₂O (15 mL) and EtOAc (10 mL). The organic phase was extracted with saturated aqueous Na₂CO₃ (2×10 mL), then the combined aqueous extracts were acidified to pH 2 with 2 M HCl, before being extracted with EtOAc (2×50 mL). The EtOAc extracts were washed with brine, before being dried (MgSO₄). Filtration, solvent evaporation, and column chromatography (IH- EtOAc, 1:1) furnished the title compound. $\delta_H$ (CDCl$_3$): 1.45 (s, 9H), 3.90-4.00 (m, 2H), 4.10-4.19 (m, 4H), 4.36-4.42 (m, 1H), 10.10-10.30 (br s, 1H).

Preparation 18

(3S)-3-Carboxymethoxy-pyrrolidine-1-carboxylic acid tert-butyl ester

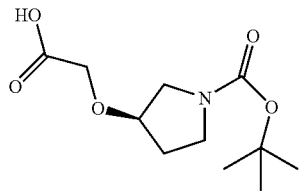

Employing procedures analogous to those described in Preparation 17, the title compound was prepared from (3S)-3-hydroxypyrrolidine-1-carboxylic acid tert-butyl ester: $\delta$H (CDCl$_3$): 1.40 (s, 9H), 1.85-2.05 (m, 2H), 3.30-3.55 (m, 4H), 4.05 (s, 2H), 4.12-4.17 (m, 1H).

Preparation 19

3-(2-Carboxyethoxy)azetidine-1-carboxylic acid tert-butyl ester

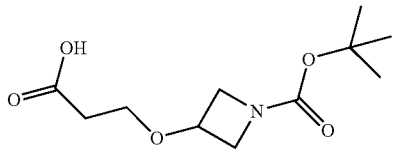

A mixture of 3-hydroxyazetidine-1-carboxylic acid tert-butyl ester (350 mg, 2.0 mmol) and NaH (6 mg of a 60% dispersion in mineral oil, 0.15 mmol) was warmed until effervescence had ceased. The mixture was stirred at ambient temperature for 15 min, then methyl acrylate (940 μL, 10.5 mmol) was added. After 3 h, the reaction was diluted with Et$_2$O (50 mL), before being washed with H$_2$O (10 mL) and brine (10 mL) then dried (MgSO$_4$). The Et$_2$O solution was filtered and evaporated, then EtOAc (15 mL) was added. The solvents were removed, then more EtOAc (15 mL) was added, before being evaporated off again to ensure that no methyl acrylate remained. The residue was dissolved in MeOH (3 mL), before being treated with 2 M NaOH (2.0 mL). After 1 h, the MeOH was removed, then H$_2$O (12 mL) and Et$_2$O (10 mL) were added. The Et$_2$O layer was extracted further with H$_2$O (8 mL), then the combined aqueous extracts were acidified to pH 2 with 2 M HCl and the resulting mixture extracted with EtOAc (50+40 mL). The combined organic extracts were washed with brine and dried (MgSO$_4$). Filtration, solvent evaporation and column chromatography (IH-EtOAc, 1:1) gave the title compound: $\delta_C$ (CDCl$_3$): 28.1, 34.8, 56.3, 63.9, 68.0, 79.9, 156.4, 176.2.

Preparation 20

7-Iodofuro[3,2-c]pyridine-2-carboxylic acid

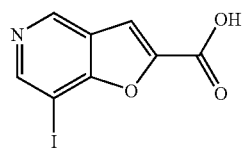

A solution of KH$_2$PO$_4$ (81 mg, 0.59 mmol) in H$_2$O (3 mL) was added to a solution of 7-iodofuro[3,2-c]pyridine-2-carbaldehyde (578 mg, 2.12 mmol) in DMSO (16 mL). The stirred mixture was treated carefully with a solution of NaClO$_2$ (335 mg, 2.96 mmol) in H$_2$O (5 mL). After 16 h, more KH$_2$PO$_4$ (81 mg, 0.59 mmol) in H$_2$O (3 mL) and NaClO$_2$ (335 mg, 2.96 mmol) in H$_2$O (5 mL) were added, then stirring was continued for a further 48 h. The precipitated solid was collected, washed with DMSO, H$_2$O, i-PrOH, and EtOAc, and vacuum-dried to furnish the title compound: m/z (ES$^+$)=289.9 [M+H]$^+$.

Example 1

4-(Furo[3,2-c]pyridine-2-carbonylsulfanyl)piperidine-1-carboxylic acid tert-butyl ester

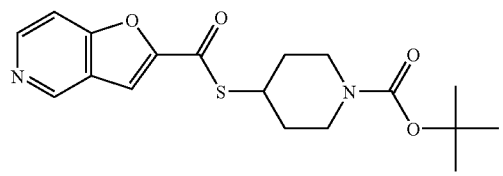

A solution of EDCI (66 mg, 0.35 mmol) in anhydrous DMF (2 mL) was added to a stirred solution of furo[3,2-c]pyridine-2-carboxylic acid (45 mg, 0.28 mmol) in anhydrous DMF (1 mL). After 1 h, the mixture was treated with a solution of DMAP (6 mg, 0.05 mmol) and 4-mercaptopiperidine-1-carboxylic acid tert-butyl ester (50 mg, 0.23 mmol), before being stirred for an additional 16 h. The DMF was removed under reduced pressure, then the residue was purified by flash chromatography (IH-EtOAc, 1:1 to 3:7) to furnish the title compound: RT=3.34 min; m/z (ES$^+$)=363.1 [M+H]$^+$.

The thioesters shown in Table 1 were prepared by condensation of the appropriate thiol with the appropriate acid employing protocols similar to those described in Example 1.

TABLE 1

| Eg | Structure | Name | RT (min) | m/z (ES+) |
|---|---|---|---|---|
| 2 | 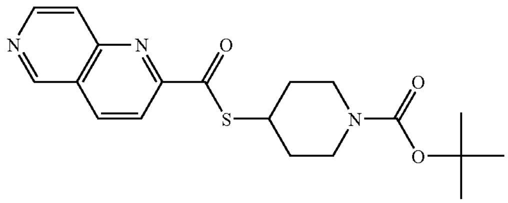 | 4-([1,6]Naphthyridine-2-carbonylsulfanyl)-piperidine-1-carboxylic acid tert-butyl ester | 3.69 | 374.1 [M + H]+ |
| 3 | 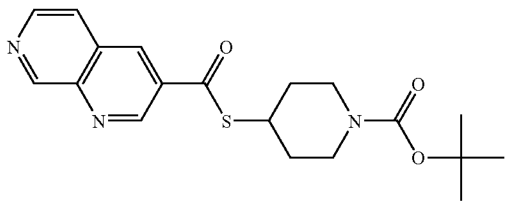 | 4-([1,7]Naphthyridine-3-carbonylsulfanyl)-piperidine-1-carboxylic acid tert-butyl ester | 3.90 | 374.1 [M + H]+ |
| 4 | 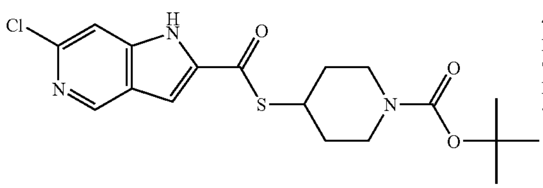 | 4-(6-Chloro-1H-pyrrolo[3,2-c]pyridine-2-carbonylsulfanyl)-piperidine-1-carboxylic acid tert-butyl ester | 3.79 | 396.0 [M + H]+ |
| 5 | 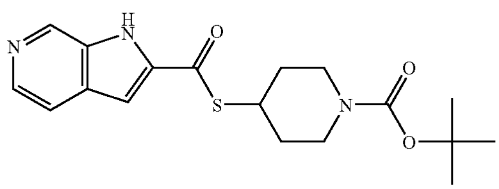 | 4-(1H-Pyrrolo[2,3-c]pyridine-2-carbonylsulfanyl)-piperidine-1-carboxylic acid tert-butyl ester | 3.04 | 362.1 [M + H]+ |
| 6 | 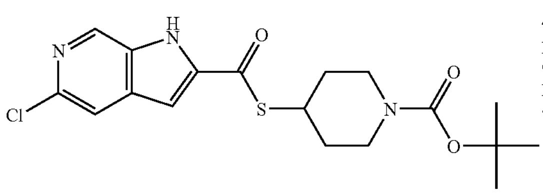 | 4-(5-Chloro-1H-pyrrolo[2,3-c]pyridine-2-carbonylsulfanyl)-piperidine-1-carboxylic acid tert-butyl ester | 3.89 | 396.1 [M + H]+ |
| 7 | 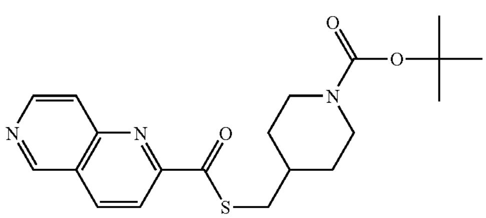 | 4-([1,6]Naphthyridine-2-carbonylsulfanylmethyl)-piperidine-1-carboxylic acid tert-butyl ester | 4.14 | 388.1 [M + H]+ |
| 8 | 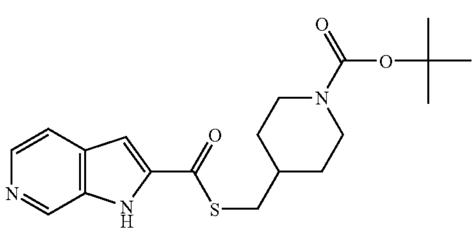 | 4-(1H-Pyrrolo[2,3-c]pyridine-2-carbonylsulfanylmethyl)-piperidine-1-carboxylic acid tert-butyl ester | 2.95 | 376.1 [M + H]+ |

TABLE 1-continued

| Eg | Structure | Name | RT (min) | m/z (ES+) |
|---|---|---|---|---|
| 9 | 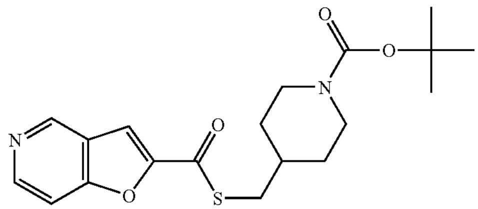 | 4-(Furo[3,2-c]pyridine-2-carbonylsulfanylmethyl)-piperidine-1-carboxylic acid tert-butyl ester | 3.44 | 377.1 [M + H]+ |
| 10 | 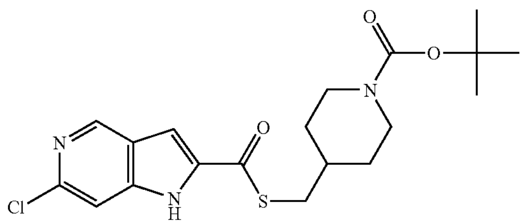 | 4-(6-Chloro-1H-pyrrolo[3,2-c]pyridine-2-carbonylsulfanylmethyl)-piperidine-1-carboxylic acid tert-butyl ester | 3.92 | 410.1 [M + H]+ |
| 11 | 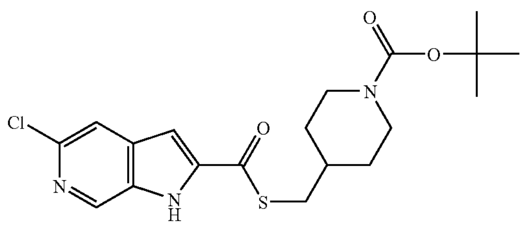 | 4-(5-Chloro-1H-pyrrolo[2,3-c]pyridine-2-carbonylsulfanylmethyl)-piperidine-1-carboxylic acid tert-butyl ester | 4.05 | 410.1 [M + H]+ |
| 12 | 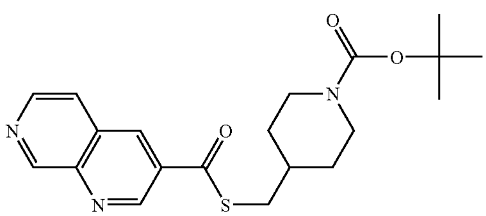 | 4-([1,7]Naphthyridine-3-carbonylsulfanylmethyl)-piperidine-1-carboxylic acid tert-butyl ester | 3.84 | 388.1 [M + H]+ |

Example 13

4-[2-(Furo[3,2-c]pyridin-2-ylmethoxy)ethyl]piperidine-1-carboxylic acid tert-butyl ester

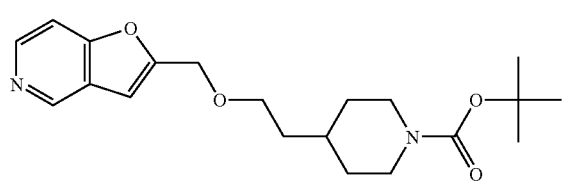

t-BuOK (45 mg, 401 µmol) and 4-(2-methanesulfonyloxyethyl)piperidine-1-carboxylic acid tert-butyl ester (134 mg, 436 µmol) were added to a stirred solution of furo[3,2-c]pyridin-2-ylmethanol (Preparation 4, 50 mg, 336 µmol) in anhydrous THF (5 mL). The reaction was heated under reflux for 6 h, before being cooled to 20° C. and quenched with saturated aqueous NH$_4$Cl. The mixture was extracted twice with EtOAc, then the combined organic extracts were washed with brine, dried (MgSO$_4$), filtered, and concentrated. The residue was purified by column chromatography (EtOAc-MeOH, 1:0 to 50:1) to furnish the title compound: RT=2.86 min; m/z (ES+)=361.3 [M+H]+.

Example 14

4-(Furo[3,2-c]pyridin-2-ylmethoxy)piperidine-1-carboxylic acid tert-butyl ester

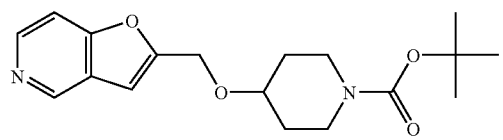

NaH (4.4 mg of a 60% dispersion in mineral oil, 110 µmol) was added to a stirred solution of 4-hydroxypiperidine-1- carboxylic acid tert-butyl ester (20.2 mg, 100 µmol) in anhydrous THF (1 mL). After 1 h, the mixture was added to a stirred solution of 2-bromomethylfuro[3,2-c]pyridine hydrochloride (Preparation 5, 25.0 mg, 100 µmol) in anhydrous THF (2 mL) which had been pretreated with NaH (4.4 mg of a 60% dispersion in mineral oil, 110 µmol). The mixture was stirred for 16 h at 20° C., before being treated with Bu$_4$NI (3.7 mg, 10 µmol) and heated at 60° C. for 4 h. On cooling, the reaction mixture was quenched with H$_2$O (5 mL), before being extracted with EtOAc (2×5 mL). The combined organic extracts were dried (MgSO$_4$), filtered, concentrated, and purified by flash chromatography (IH-EtOAc, 2:3) to yield the title compound: RT=2.64 min; m/z (ES$^+$)=333.3 [M+H]$^+$.

The ethers shown in Table 2 were synthesised via the reaction of the appropriate alcohol with 2-bromomethylfuro[3,2-c]pyridine hydrochloride (Preparation 5) employing protocols similar to those described in Example 14.

pyridin-2-ylmethyltriphenylphosphonium bromide hydrochloride (Preparation 6, 1.50 g, 2.94 mmol) in anhydrous THF (25 mL) at 0° C. After 45 min, the mixture was treated with 4-formylpiperidine-1-carboxylic acid tert-butyl ester (0.63 g, 2.94 mmol), before being stirred at 20° C. for 16 h. The reaction mixture was diluted with EtOAc (300 mL), before being washed with H$_2$O (2×100 mL) and dried (MgSO$_4$). Filtration, solvent evaporation, and flash chromatography (IH-EtOAc, 1:1) furnished 4-(2-furo[3,2-c]pyridin-2-ylvinyl)piperidine-1-carboxylic acid tert-butyl ester: m/z (ES$^+$)=329.1 [M+H]$^+$. This alkene (830 mg, 2.53 mmol) was dissolved in EtOH (15 mL), then Pd (10% on C, 83 mg, 0.08 mmol) was added. The reaction was stirred under a H$_2$ atmosphere for 16 h, before being filtered through celite. The celite was washed with MeOH, then the combined solutions were concentrated to provide the title compound: RT=2.86 min; m/z (ES$^+$)=331.2 [M+H]$^+$.

TABLE 2

| Eg | Structure | Name | RT (min) | m/z (ES$^+$) |
|---|---|---|---|---|
| 15 | 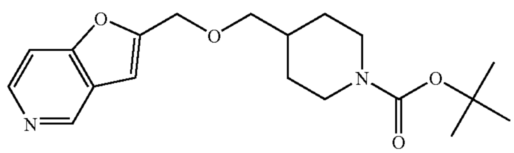 | 4-(Furo[3,2-c]pyridin-2-ylmethoxymethyl)-piperidine-1-carboxylic acid tert-butyl ester | 2.74 | 347.3 [M + H]$^+$ |
| 16 | 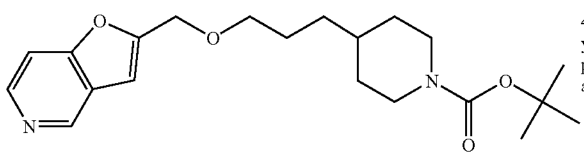 | 4-[3-(Furo[3,2-c]pyridin-2-ylmethoxy)propyl]-piperidine-1-carboxylic acid tert-butyl ester | 3.01 | 375.4 [M + H]$^+$ |
| 17 | 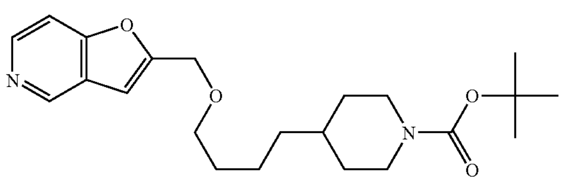 | 4-[4-(Furo[3,2-c]pyridin-2-ylmethoxy)butyl]-piperidine-1-carboxylic acid tert-butyl ester | 3.22 | 389.4 [M + H]$^+$ |

Example 18

4-(2-Furo[3,2-c]pyridin-2-ylethyl)piperidine-1-carboxylic acid tert-butyl ester

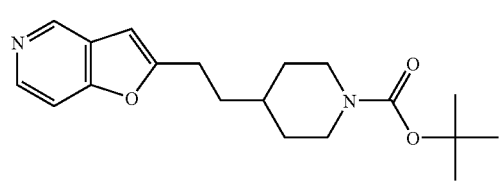

LiHMDS (5.9 mL of a 1.0 M solution in THF, 5.90 mmol) was added dropwise to a stirred suspension of furo[3,2-c]

Example 19

4-(3-Furo[3,2-c]pyridin-2-ylpropyl)piperidino-1-carboxylic acid tert-butyl ester

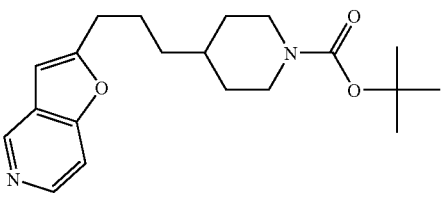

Employing protocols similar to those described in Example 18, Wittig reaction of furo[3,2-c]pyridin-2-ylmethyltriphenylphosphonium bromide hydrochloride (Preparation 6) with 4-(2-oxoethyl)piperidine-1-carboxylic acid tert-butyl ester, followed by reduction of the alkene produced, furnished the title compound: RT=2.99 min; m/z (ES⁺)=345.2 [M+H]⁺.

Example 20

4-(2-Furo[2,3-c]pyridin-2-ylethyl)piperidino-1-carboxylic acid tert-butyl ester

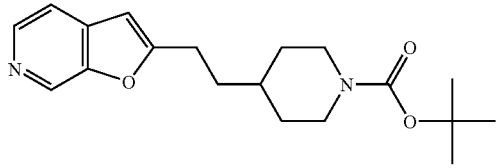

K$_2$CO$_3$ (122 mg, 0.88 mmol) and 18C6 (catalytic amount) were added to a stirred solution of (1-tert-butoxycarbonylpiperidin-4-ylmethyl)triphenylphosphonium iodide (491 mg, 0.88 mmol) and furo[2,3-c]pyridine-2-carbaldehyde (65 mg, 0.44 mmol) in anhydrous CH$_2$Cl$_2$ (10 mL). After 64 h, the reaction mixture was partitioned between CH$_2$Cl$_2$ (50 mL) and H$_2$O (20 mL). The aqueous phase was further extracted with CH$_2$Cl$_2$ (2×20 mL), then the combined organic extracts were washed with H$_2$O (20 mL) and brine (20 mL), before being dried (MgSO$_4$). Filtration, solvent evaporation, and flash chromatography (IH-EtOAc, 7:3) afforded 4-(2-furo[2,3-c]pyridin-2-ylvinyl)piperidine-1-carboxylic acid tert-butyl ester: m/z (ES⁺)=329.2 [M+H]⁺. This alkene (30 mg, 91 μmol) was hydrogenated, as described above in Example 18, to yield the title compound: RT=2.86 min; m/z (ES⁺)=331.2 [M+H]⁺.

Example 21

4-(2-Oxazolo[4,5-c]pyridin-2-yl-2-oxo-ethyl)piperidine-1-carboxylic acid tert-butyl ester

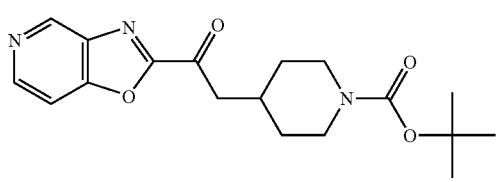

The Dess-Martin periodinane (23.7 mg, 60 μmol) was added to a stirred solution of 4-(2-hydroxy-2-oxazolo[4,5-c]pyridin-2-yl-ethyl)piperidine-1-carboxylic acid tert-butyl ester (Preparation 7, 19.4 mg, 60 μmol) in anhydrous CH$_2$Cl$_2$ (2 mL). After 16 h, the reaction mixture was diluted with CH$_2$Cl$_2$ (15 mL), before being washed with a saturated aqueous Na$_2$S$_2$O$_3$-saturated aqueous NaHCO$_3$ solution (7:1, 3×5 mL). The CH$_2$Cl$_2$ layer was dried (MgSO$_4$), filtered, and concentrated. Flash chromatography (IH-EtOAc, 1:9) provided the title compound: RT=3.39 min; m/z (ES⁺)=346.1 [M+H]⁺.

Example 22

4-(2-Chloro-2-oxazolo[4,5-c]pyridin-2-ylethyl)piperidine-1-carboxylic acid tert-butyl ester

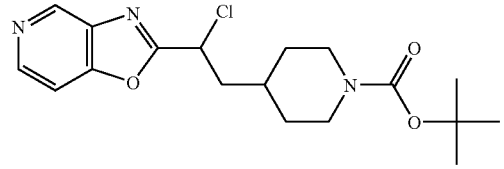

MsCl (29 μL, 0.38 mmol) was added to a stirred solution of 4-(2-hydroxy-2-oxazolo[4,5-c]pyridin-2-yl-ethyl)piperidine-1-carboxylic acid tert-butyl ester (Preparation 7, 110 mg, 0.32 mmol) in anhydrous pyridine (5 mL) at 0° C. After 1 h, more MsCl (29 μL, 0.38 mmol) was added, then the mixture was stirred at 0° C. for an additional 1 h, before being heated under reflux for 1 h. The reaction was concentrated under reduced pressure, then the residue was purified by flash chromatography (EtOAc-IH, 7:3) to furnish the title compound: RT=3.57 min; m/z (ES⁺)=310.0 [M+2H-t-Bu]⁺.

Example 23

4-(2-Oxazolo[4,5-c]pyridin-2-yl-ethyl)piperidine-1-carboxylic acid tert-butyl ester

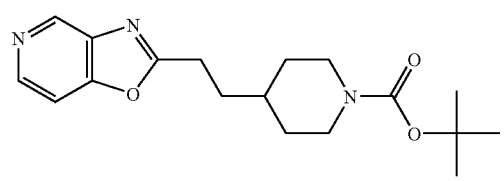

NaI (2 mg) was added to a solution of 4-(2-chloro-2-oxazolo[4,5-c]pyridin-2-ylethyl)-piperidine-1-carboxylic acid tert-butyl ester (Example 22, 18 mg, 49 μmol) in anhydrous pyridine (1 mL). The mixture was heated under microwave irradiation for 10 min at 150° C., before being concentrated in vacuo. The residue was taken up in EtOAc (20 mL), then the EtOAc solution was washed with a mixture of saturated aqueous NaHCO$_3$ and saturated aqueous Na$_2$S$_2$O$_3$ (1:1, 2×8 mL), before being dried (MgSO$_4$). Filtration, solvent evaporation, and flash chromatography (EtOAc-IH, 17:3) yielded 4-(2-oxazolo[4,5-c]pyridin-2-ylvinyl)-piperidine-1-carboxylic acid tert-butyl ester as a 1:1 mixture of (E)- and (Z)-isomers: m/z (ES⁺)=330.1 [M+H]⁺. A solution of this compound (10 mg, 30 μmol) in EtOH (1 mL) was stirred with Pd (10% on C, 1 mg) under a H$_2$ atmosphere for 4 h. The mixture was filtered through celite, washing with MeOH. The combined filtrates were concentrated under reduced pressure to afford the title compound: RT=2.89 min; m/z (ES+)=332.2 [M+H]+.

Example 24

4-[5-(4-Hydroxymethylfuro[3,2-c]pyridin-2-yl)-[1,2,4]oxadiazol-3-ylmethoxy]-piperidine-1-carboxylic acid tert-butyl ester

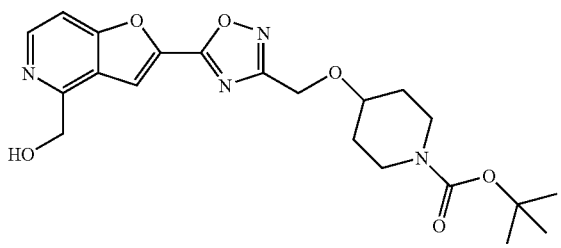

To solution of 4-{5-[4-(tert-butylmethylsilanyloxymethyl)furo[3,2-c]pyridine-2-yl]-[1,2,4]oxadiazole-3-ylmethoxy}piperidine-1-carboxylic acid tert-butyl ester (Preparation 8, 54 mg, 99 μmol) in THF was added TBAF (0.25 mL of a 1.0M solution in THF, 250 μmol). After 10 min, the mixture was diluted with EtOAc, washed with H₂O and brine, before being dried and concentrated. Purification via column chromatography afforded the title compound: RT=2.92 min; m/z (ES+)=431.1 [M+H]+.

Example 25

4-[5-(4-Methoxymethylfuro[3,2-c]pyridine-2-yl)-[1,2,4]oxadiazole-3-ylmethoxy]piperidine-1-carboxylic acid tert-butyl ester

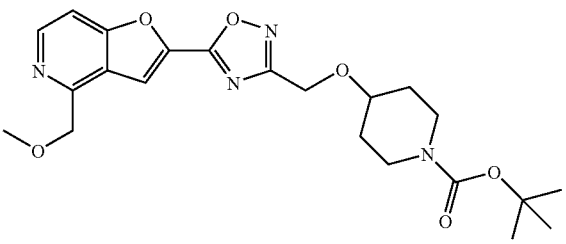

To a stirred solution of 4-[5-(4-hydroxymethylfuro[3,2-c]pyridine-2-yl)-[1,2,4]oxadiazole-3-ylmethoxy]piperidine-1-carboxylic acid tert-butyl ester (Example 24, 50 mg, 116 μmol) in THF was added sodium hydride (60% dispersion in mineral oil, 6 mg, 150 μmol). After effervescence had ceased, MeI (10 μL, 161 μmol) was added. After 90 min, the mixture was poured into H₂O and extracted with EtOAc. The organic layer was separated, washed with brine, dried and concentrated. Purification via column chromatography afforded the title compound: RT=3.54 min; m/z (ES+)=445.1 [M+H]+.

Example 26

4-[5-(4-Dimethylaminomethylfuro[3,2-c]pyridine-2-yl)-[1,2,4]oxadiazole-3-ylmethoxy]piperidine-1-carboxylic acid tert-butyl ester

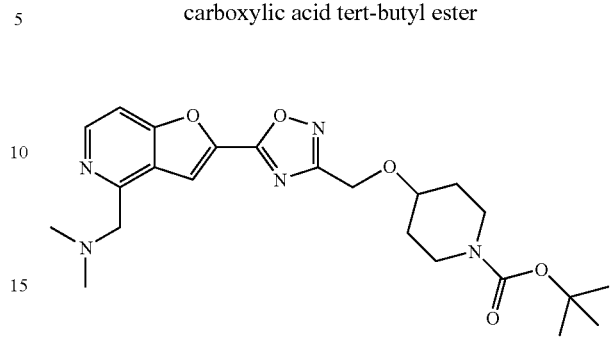

To a solution of 4-[5-(4-hydroxymethylfuro[3,2-c]pyridine-2-yl)-[1,2,4]oxadiazole-3-ylmethoxy]piperidine-1-carboxylic acid tert-butyl ester (Example 24, 50 mg, 116 μmol) in THF was added NEt₃ (50 mL, 361 μmol), followed by MsCl (15 μL, 194 μmol). After 5 min, of Me₂NH (0.3 mL of a 2M solution in THF, 600 μmol) was added and stirring continued for a further 2 h. The mixture was adsorbed onto SiO₂ and purified via column chromatography to give the title compound: RT=1.82 min; m/z (ES+)=458.1 [M+H]+.

Example 27

4-[5-(4-Pyrrolidin-1-ylmethylfuro[3,2-c]pyridine-2-yl)-[1,2,4]oxadiazole-3-ylmethoxy]-piperidine-1-carboxylic acid tert-butyl ester

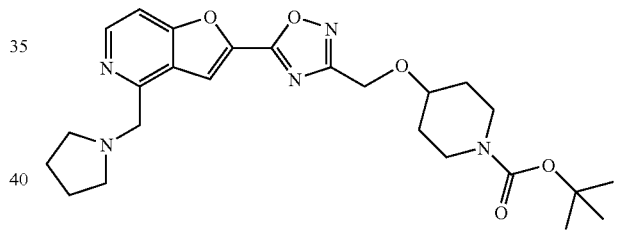

This compound was obtained from 4-[5-(4-hydroxymethylfuro[3,2-c]pyridine-2-yl)-[1,2,4]oxadiazole-3-ylmethoxy]piperidine-1-carboxylic acid tert-butyl ester (Example 24) employing a procedure similar to that outlined in Example 26: RT=2.64 min; m/z (ES+)=484.1 [M+H]+.

Example 28

4-[5-(4-Formylfuro[3,2-c]pyridine-2-yl)-[1,2,4]oxadiazole-3-ylmethoxy]piperidine-1-carboxylic acid tert-butyl ester

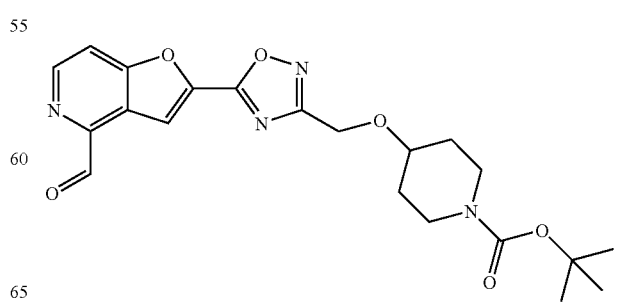

To a solution of 4-[5-(4-hydroxymethylfuro[3,2-c]pyridine-2-yl)-[1,2,4]oxadiazole-3-ylmethoxy]piperidine-1-carboxylic acid tert-butyl ester (Example 24, 25 mg, 58 μmol) in CH$_2$Cl$_2$ was added Dess-Martin periodinane (32 mg, 75 μmol). After 3 h at 20° C., the mixture was diluted with MeOH, adsorbed onto SiO$_2$ and purified by column chromatography to furnish the title compound: RT=3.27 min; m/z (ES$^+$)=429.1 [M+H]$^+$.

Example 29

4-{[(5-Furo[3,2-c]pyridin-2-yl-[1,2,4]oxadiazol-3-ylmethyl)amino]methyl}-piperidine-1-carboxylic acid tert-butyl ester

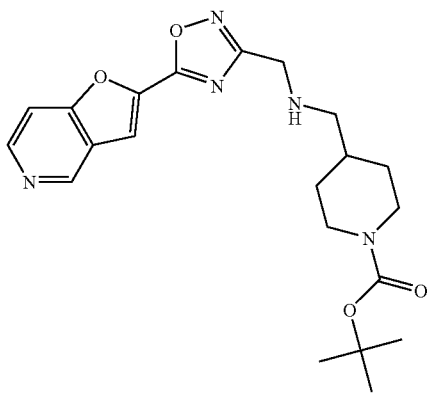

A solution of C-(5-furo[3,2-c]pyridin-2-yl-[1,2,4]oxadiazol-3-yl)methylamine (Preparation 14, 50 mg, 0.23 mmol) and 4-formylpiperidine-1-carboxylic acid tert-butyl ester (59 mg, 0.27 mmol) in anhydrous CH$_2$Cl$_2$ (5 mL) was stirred for 45 min. Na(AcO)$_3$BH (78 mg, 0.37 mmol) was added, then the mixture was stirred for 3 d. Standard aqueous work-up, followed by column chromatography (EtOAc), gave the title compound: RT=2.18 min; m/z (ES$^+$)=414.1 [M+H]$^+$.

Example 30

4-[(5-Furo[3,2-c]pyridin-2-yl-[1,2,4]oxadiazol-3-ylmethyl)amino]piperidine-1-carboxylic acid tert-butyl ester

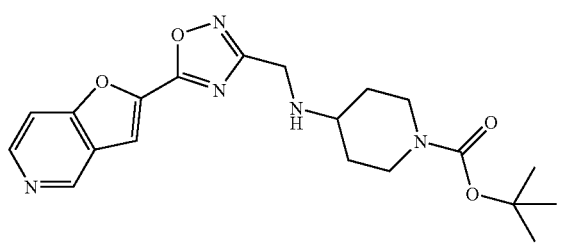

A solution of C-(5-furo[3,2-c]pyridin-2-yl-[1,2,4]oxadiazol-3-yl)methylamine (Preparation 14, 350 mg, 1.62 mmol) and 4-oxo-piperidine-1-carboxylic acid tert-butyl ester (322 mg, 1.62 mmol) in anhydrous CH$_2$Cl$_2$ (5 mL) was stirred for 10 min. Na(AcO)$_3$BH (412 mg, 1.94 mmol) was added, then the mixture was stirred for 3 d. Standard aqueous work-up, followed by column chromatography (EtOAc-IH, 1:1) gave the title compound: m/z (ES$^+$)=400.0 [M+H]$^+$.

Example 31

4-[(3-Furo[3,2-c]pyridin-2-yl-[1,2,4]oxadiazol-5-ylmethyl)amino]piperidine-1-carboxylic acid tert-butyl ester

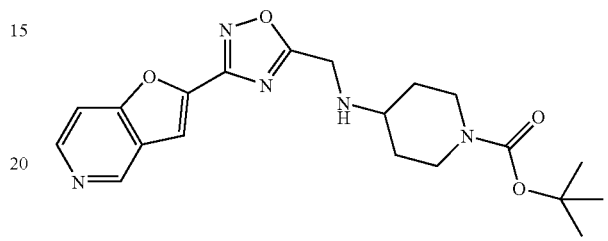

Reductive alkylation of C-(3-furo[3,2-c]pyridin-2-yl-[1,2,4]oxadiazol-5-yl)-methylamine (Preparation 13) with 4-oxo-piperidine-1-carboxylic acid tert-butyl ester, utilising a procedure similar to that described in Example 30, afforded the title compound: RT=2.15 min; m/z (ES$^+$)=400.1 [M+H]$^+$.

Example 32

4-[Ethyl(5-furo[3,2-c]pyridin-2-yl-[1,2,4]oxadiazol-3-ylmethyl)amino]-piperidine-1-carboxylic acid tert-butyl ester

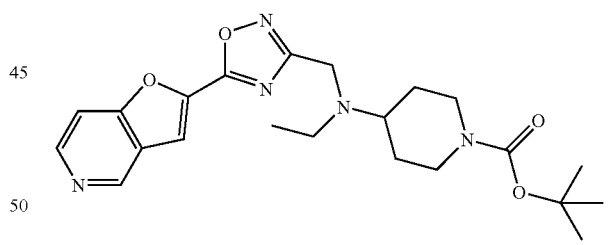

A solution of 4-[(5-furo[3,2-c]pyridin-2-yl-[1,2,4]oxadiazol-3-ylmethyl)amino]-piperidine-1-carboxylic acid tert-butyl ester (Example 30, 50 mg, 120 μmol), MeCHO (6 μL, 120 μmol), and NaBH(OAc)$_3$ (36 mg, 168 μmol) in CH$_2$Cl$_2$ (5 mL) was stirred for 3 d at ambient temperature. The reaction mixture was washed with water, before being dried (MgSO$_4$) and purified by column chromatography to furnish the title compound: RT=2.40 min; m/z (ES$^+$)=428.2 [M+H]$^+$.

The Examples catalogued in Table 3 were synthesised employing procedures similar to those outlined in Example 32.

TABLE 3

| Eg | Structure | Name | RT (min) | m/z (ES+) |
|---|---|---|---|---|
| 33 | 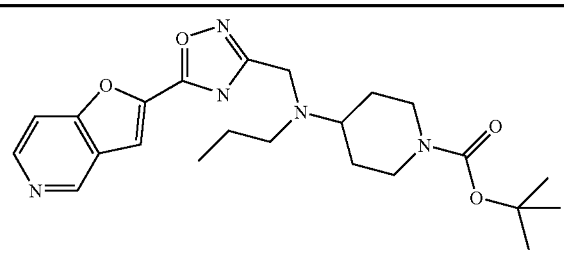 | 4-[(5-Furo[3,2-c]pyridin-2-yl-[1,2,4]oxadiazol-3-ylmethyl)propylamino]-piperidine-1-carboxylic acid tert-butyl ester | 2.43 | 442.1 [M + H]+ |
| 34 | 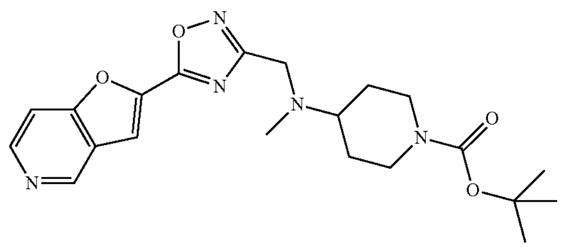 | 4-[(5-Furo[3,2-c]pyridin-2-yl-[1,2,4]oxadiazol-3-ylmethyl)methylamino]-piperidine-1-carboxylic acid tert-butyl ester | 2.07 | 414.1 [M + H]+ |
| 35 | 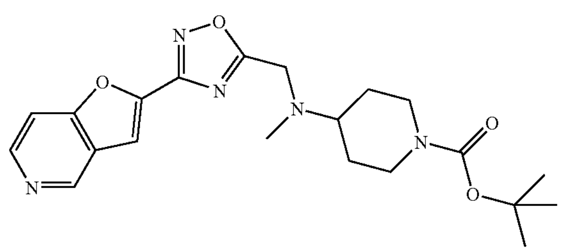 | 4-[(3-Furo[3,2-c]pyridin-2-yl-[1,2,4]oxadiazol-5-ylmethyl)methylamino]-piperidine-1-carboxylic acid tert-butyl ester | 2.32 | 414.1 [M + H]+ |
| 36 | 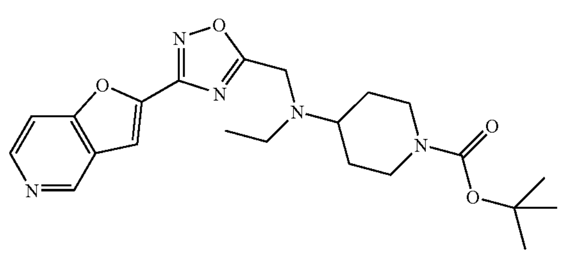 | 4-[Ethyl(3-furo[3,2-c]pyridin-2-yl-[1,2,4]oxadiazol-5-ylmethyl)amino]-piperidine-1-carboxylic acid tert-butyl ester | 2.36 | 428.2 [M + H]+ |

Example 37

4-(5-Thieno[2,3-c]pyridin-2-yl-[1,2,4]oxadiazol-3-yl)piperidine-1-carboxylic acid tert-butyl ester

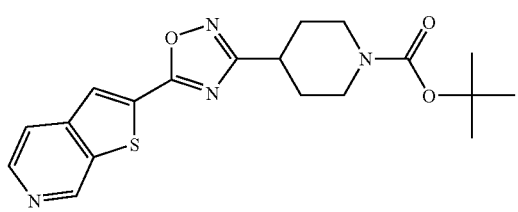

EDCI (96 mg, 0.50 mmol) and DMAP (8 mg, 0.07 mmol) were added to a stirred suspension of thieno[2,3-c]pyridine-2-carboxylic acid (60 mg, 0.33 mmol) in anhydrous DMF (4 mL). The clear solution that resulted was stirred for 10 min, then 4-(N-hydroxycarbamimidoyl)piperidine-1-carboxylic acid tert-butyl ester (81 mg, 0.33 mmol) was added. After 16 h, the DMF was removed in vacuo, then the residue was purified by flash chromatography to provide the desired O-acylamidoxime: m/z (ES+)=405.2 [M+H]+. This compound (55 mg, 0.13 mmol) was dissolved in anhydrous dioxane (4 mL), then dried, powdered 4 Å molecular sieves (210 mg) were added. The mixture was heated under reflux for 16 h, before being cooled, filtered, and concentrated under reduced pressure. Purification by flash chromatography (IH-EtOAc, 3:7) followed by RP-HPLC afforded the title compound: RT=3.79 min; m/z (ES+)=387.1 [M+H]+.

The [1,2,4]oxadiazoles listed in Table 4 were prepared by condensation of the appropriate amidoxime with the appropriate acid to furnish an O-acylamidoxime that was cyclised by heating with 4 Å molecular sieves, employing procedures similar to those delineated in Example 37.

TABLE 4

| Eg | Structure | Name | RT (min) | m/z (ES+) |
|---|---|---|---|---|
| 38 | 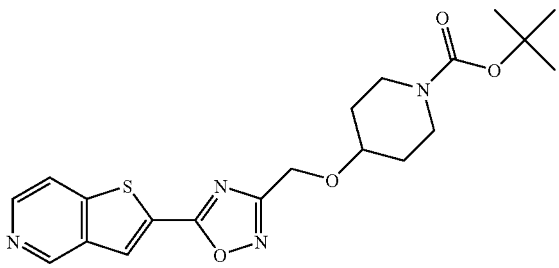 | 4-(5-Thieno[3,2-c]pyridin-2-yl-[1,2,4]oxadiazol-3-ylmethoxy)piperidine-1-carboxylic acid tert-butyl ester | 3.52 | 417.2 [M + H]+ |
| 39 | 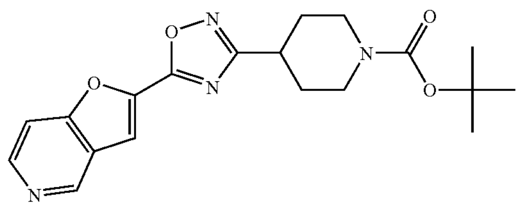 | 4-(5-Furo[3,2-c]pyridin-2-yl-[1,2,4]oxadiazol-3-yl)piperidine-1-carboxylic acid tert-butyl ester | 3.36 | 371.2 [M + H]+ |
| 40 | 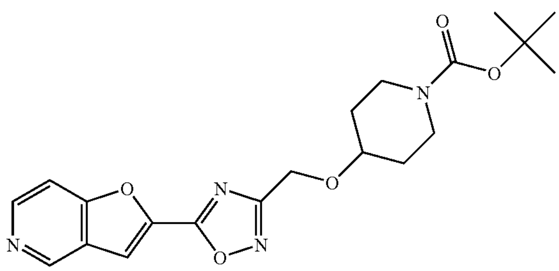 | 4-(5-Furo[3,2-c]pyridin-2-yl-[1,2,4]oxadiazol-3-yl)methoxy)piperidine-1-carboxylic acid tert-butyl ester | 3.31 | 401.2 [M + H]+ |
| 41 | 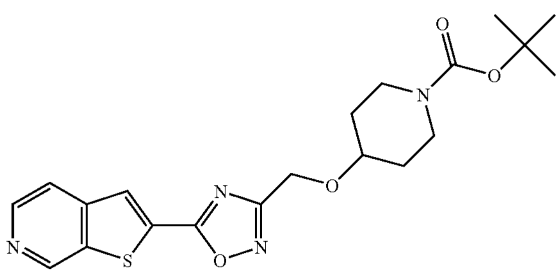 | 4-(5-Thieno[2,3-c]pyridin-2-yl-[1,2,4]oxadiazol-3-ylmethoxy)piperidine-1-carboxylic acid tert-butyl ester | 3.61 | 417.1 [M + H]+ |
| 42 | 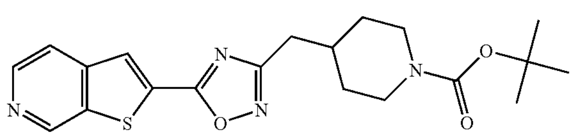 | 4-(5-Thieno[2,3-c]pyridin-2-yl-[1,2,4]oxadiazol-3-ylmethyl)piperidine-1-carboxylic acid tert-butyl ester | 3.87 | 401.1 [M + H]+ |
| 43 | 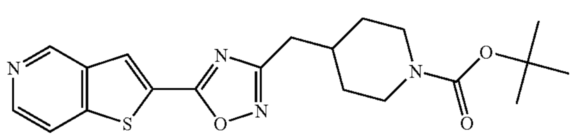 | 4-(5-Thieno[3,2-c]pyridin-2-yl-[1,2,4]oxadiazol-3-ylmethyl)piperidine-1-carboxylic acid tert-butyl ester | 3.74 | 401.1 [M + H]+ |
| 44 | 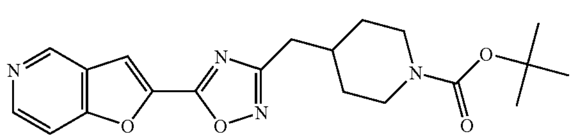 | 4-(5-Furo[3,2-c]pyridin-2-yl-[1,2,4]oxadiazol-3-ylmethyl)piperidine-1-carboxylic acid tert-butyl ester | 3.47 | 385.2 [M + H]+ |

TABLE 4-continued

| Eg | Structure | Name | RT (min) | m/z (ES+) |
|---|---|---|---|---|
| 45 | 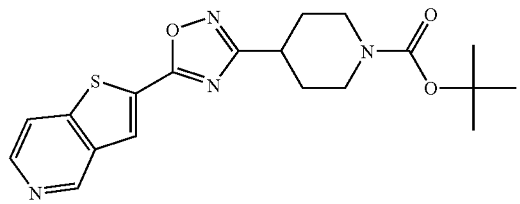 | 4-(5-Thieno[3,2-c]pyridin-2-yl-[1,2,4]oxadiazol-3-yl)-piperidine-1-carboxylic acid tert-butyl ester | 3.65 | 387.1 [M + H]+ |
| 46 | 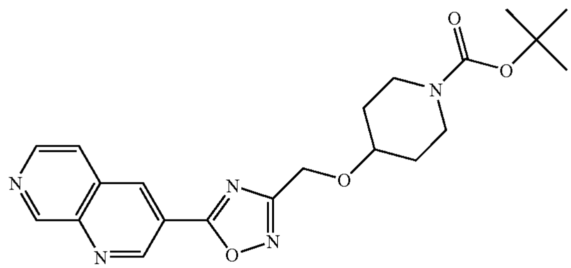 | 4-(5-[1,7]Naphthyridin-3-yl-[1,2,4]oxadiazol-3-ylmethoxy)piperidine-1-carboxylic acid tert-butyl ester | 3.70 | 412.2 [M + H]+ |
| 47 | 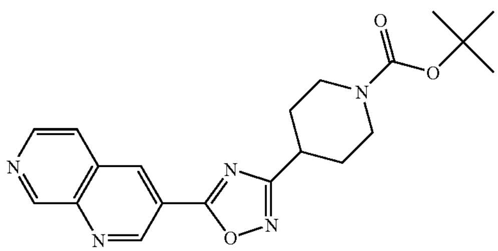 | 4-(5-[1,7]Naphthyridin-3-yl-[1,2,4]oxadiazol-3-yl)-piperidine-1-carboxylic acid tert-butyl ester | 3.86 | 382.2 [M + H]+ |
| 48 | 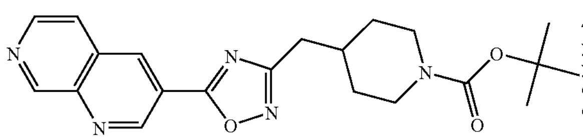 | 4-(5-[1,7]Naphthyridin-3-yl-[1,2,4]oxadiazol-3-ylmethyl)piperidine-1-carboxylic acid tert-butyl ester | 3.89 | 396.2 [M + H]+ |
| 49 | 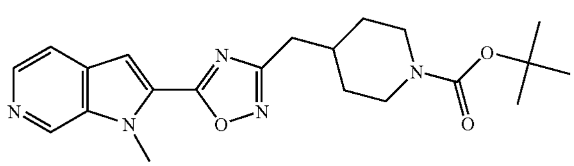 | 4-[5-(1-Methyl-1H-pyrrolo[2,3-c]pyridin-2-yl)-[1,2,4]oxadiazol-3-ylmethyl]piperidine-1-carboxylic acid tert-butyl ester | 2.97 | 398.2 [M + H]+ |
| 50 | 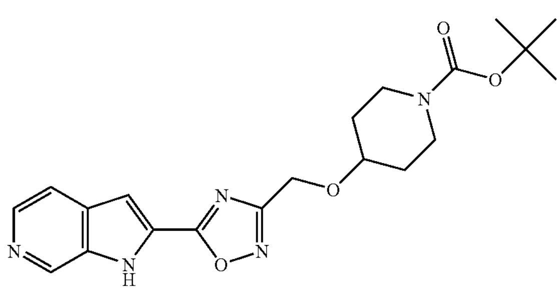 | 4-[5-(1H-Pyrrolo[2,3-c]pyridin-2-yl)-[1,2,4]oxadiazol-3-ylmethoxy]piperidine-1-carboxylic acid tert-butyl ester | 2.89 | 400.2 [M + H]+ |
| 51 | 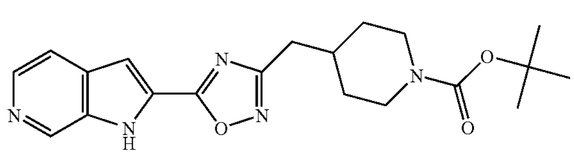 | 4-[5-(1H-Pyrrolo[2,3-c]pyridin-2-yl)-[1,2,4]oxadiazol-3-ylmethyl]piperidine-1-carboxylic acid tert-butyl ester | 2.95 | 384.2 [M + H]+ |

TABLE 4-continued

| Eg | Structure | Name | RT (min) | m/z (ES+) |
|---|---|---|---|---|
| 52 | 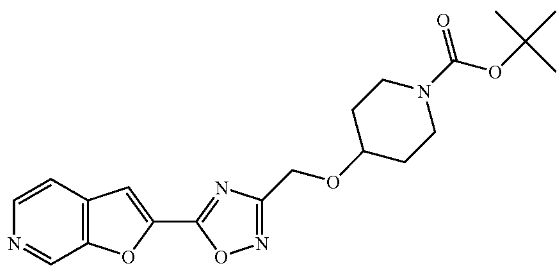 | 4-(5-Furo[2,3-c]pyridin-2-yl-[1,2,4]oxadiazol-3-ylmethoxy)piperidine-1-carboxylic acid tert-butyl ester | 3.51 | 401.2 [M + H]+ |
| 53 | 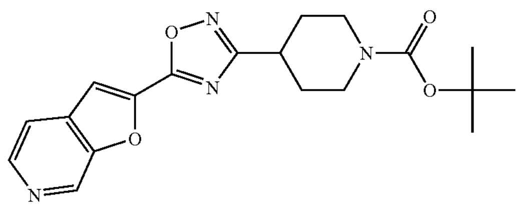 | 4-(5-Furo[2,3-c]pyridin-2-yl-[1,2,4]oxadiazol-3-yl)piperidine-1-carboxylic acid tert-butyl ester | 3.59 | 371.2 [M + H]+ |
| 54 | 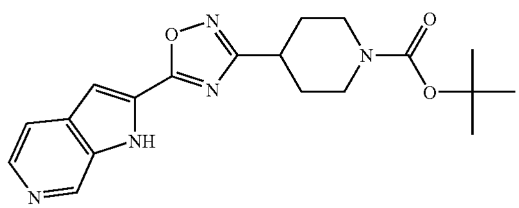 | 4-[5-(1H-Pyrrolo[2,3-c]pyridin-2-yl)-[1,2,4]oxadiazol-3-yl]-piperidine-1-carboxylic acid tert-butyl ester | 2.94 | 370.2 [M + H]+ |
| 55 | 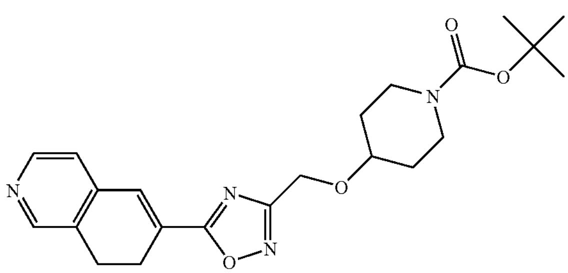 | 4-[5-(7,8-Dihydro-isoquinolin-6-yl)-[1,2,4]oxadiazol-3-ylmethoxy]piperidine-1-carboxylic acid tert-butyl ester | 2.97 | 413.3 [M + H]+ |
| 56 | 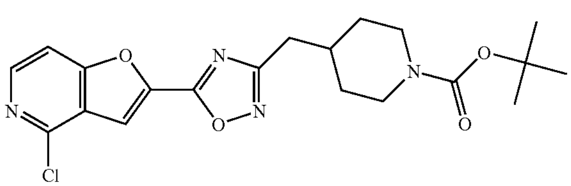 | 4-[5-(4-Chlorofuro[3,2-c]pyridin-2-yl)-[1,2,4]oxadiazol-3-ylmethyl]piperidine-1-carboxylic acid tert-butyl ester | 4.07 | 419.1 [M + H]+ |
| 57 | 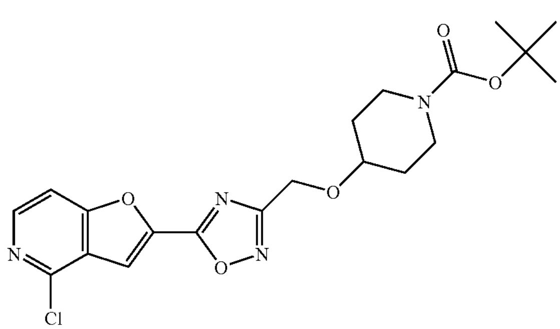 | 4-[5-(4-Chlorofuro[3,2-c]pyridin-2-yl)-[1,2,4]oxadiazol-3-ylmethoxy]piperidine-1-carboxylic acid tert-butyl ester | 3.81 | 435.2 [M + H]+ |

Example 58

4-(3-Furo[3,2-c]pyridin-2-yl-[1,2,4]oxadiazol-5-ylmethyl)piperidine-1-carboxylic acid tert-butyl ester

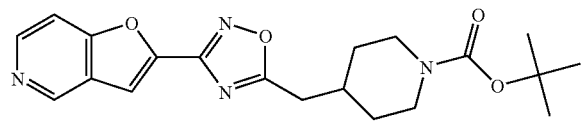

A stirred solution of 4-carboxymethylpiperidine-1-carboxylic acid tert-butyl ester (132 mg, 542 µmol) in anhydrous THF (6 mL) was treated with NEt$_3$ (76 ΔL, 542 µmol), before being cooled down to 0° C. i-BuOCOCl (542 µL of a 1 µmol/µL solution, 542 µmol) was added, then the reaction mixture was warmed to ambient temperature. After 40 min, N-hydroxy-furo[3,2-c]pyridine-2-carboxamidine (Preparation 11, 80 mg, 452 µmol) was added, then the reaction was stirred for 16 h, before being purified by column chromatography (EtOAc then EtOAc-MeOH, 24:1) to furnish the acylated amidoxime intermediate: m/z (ES$^+$)=403.2 [M+H]$^+$. A solution of this compound (98 mg) in PhMe (15 mL) was heated under reflux for 40 h. The solvents were removed in vacuo, then the residue was purified by two separate column chromatographic separations ([1]: CH$_2$C$_1$-MeOH, 49:1; [2] EtOAc) to give the title compound: RT=3.11 min; m/z (S$^+$)=385.1 [M+H]$^+$.

The [1,2,4]oxadiazoles listed in Table 5 were prepared employing procedures similar to those outlined in Example 58.

TABLE 5

| Eg | Structure | Name | RT (min) | m/z (ES$^+$) |
|---|---|---|---|---|
| 59 | 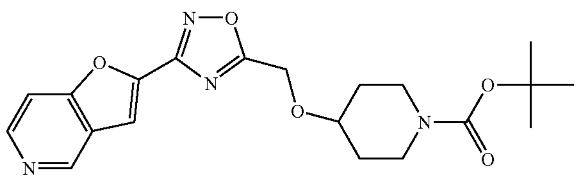 | 4-(3-Furo[3,2-c]pyridin-2-yl-[1,2,4]oxadiazol-5-ylmethoxy)piperidine-1-carboxylic acid tert-butyl ester | 2.90 | 401.1 [M + H]$^+$ |
| 60 | 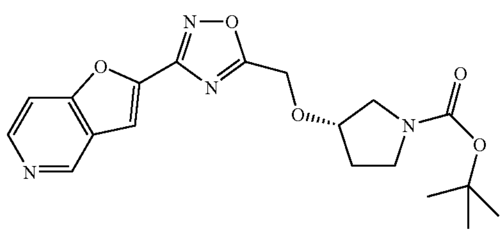 | (3S)-3-(3-Furo[3,2-c]pyridin-2-yl-[1,2,4]oxadiazol-5-ylmethoxy)pyrrolidine-1-carboxylic acid tert-butyl ester | 2.76 | 387.0 [M + H]$^+$ |
| 61 | 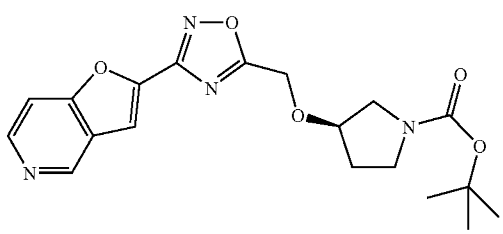 | (3R)-3-(3-Furo[3,2-c]pyridin-2-yl-[1,2,4]oxadiazol-5-ylmethoxy)pyrrolidine-1-carboxylic acid tert-butyl ester | 2.74 | 387.1 [M + H]$^+$ |
| 62 | 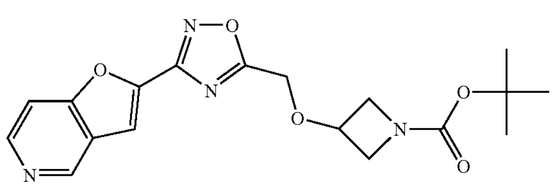 | 3-(3-Furo[3,2-c]pyridin-2-yl-[1,2,4]oxadiazol-5-ylmethoxy)azetidine-1-carboxylic acid tert-butyl ester | 2.70 | 373.1 [M + H]$^+$ |
| 63 | 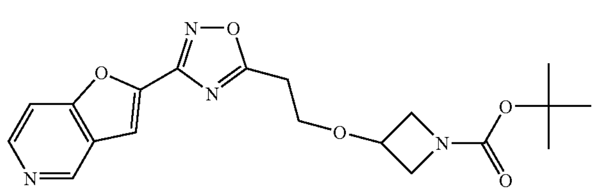 | 3-[2-(3-Furo[3,2-c]pyridin-2-yl-[1,2,4]oxadiazol-5-yl)-ethoxy]azetidine-1-carboxylic acid tert-butyl ester | 2.79 | 387.1 [M + H]$^+$ |

Example 64

4-(5-Furo[3,2-c]pyridin-2-yl-[1,2,4]oxadiazol-3-ylmethyl)piperidine-1-carboxylic acid propyl ester

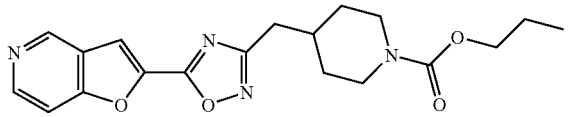

A solution of 2-(3-piperidin-4-ylmethyl-[1,2,4]oxadiazol-5-yl)furo[3,2-c]pyridine (Preparation 12, 0.65 g, 2.3 mmol) and pyridine (0.37 mL, 4.6 mmol) in anhydrous $CH_2Cl_2$ (25 mL) was added via cannula to a stirred solution of n-PrO-COCl (0.51 mL, 4.6 mmol) in anhydrous $CH_2Cl_2$ (35 mL). After 16 h, the reaction mixture was diluted with $Et_2O$ (200 mL), before being washed with $H_2O$ (100 mL), saturated aqueous $Na_2CO_3$ (100 mL), and $H_2O$ (100 mL). The organic phase was dried, filtered and concentrated. Flash chromatographic purification (EtOAc) of the residue furnished the title compound: RT=3.11 min; m/z $(ES^+)$=371.1 $[M+H]^+$.

The carbamates shown in Table 6 were prepared by reacting 2-(3-piperidin-4-ylmethyl-[1,2,4]oxadiazol-5-yl)furo[3,2-c]pyridine (Preparation 12) with the appropriate chloroformate employing procedures similar to those delineated in Example 64.

TABLE 6

| Eg | Structure | Name | RT (min) | m/z $(ES^+)$ |
|---|---|---|---|---|
| 65 | 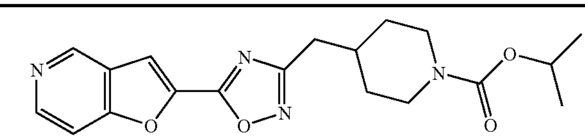 | 4-(5-Furo[3,2-c]pyridin-2-yl-[1,2,4]oxadiazol-3-ylmethyl)piperidine-1-carboxylic acid isopropyl ester | 3.07 | 371.1 $[M + H]^+$ |
| 66 | 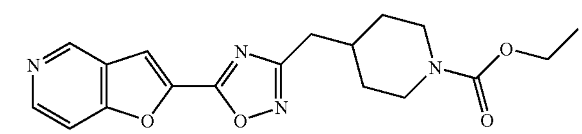 | 4-(5-Furo[3,2-c]pyridin-2-yl-[1,2,4]oxadiazol-3-ylmethyl)piperidine-1-carboxylic acid ethyl ester | 2.84 | 357.1 $[M + H]^+$ |
| 67 | 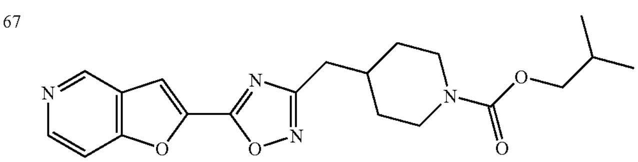 | 4-(5-Furo[3,2-c]pyridin-2-yl-[1,2,4]oxadiazol-3-ylmethyl)piperidine-1-carboxylic acid isobutyl ester | 3.34 | 385.1 $[M + H]^+$ |
| 68 | 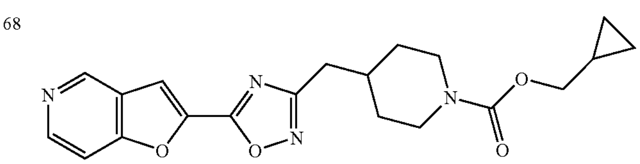 | 4-(5-Furo[3,2-c]pyridin-2-yl-[1,2,4]oxadiazol-3-ylmethyl)piperidine-1-carboxylic acid cyclopropylmethyl ester | 3.16 | 383.1 $[M + H]^+$ |

The carbamates catalogued in Table 7 were prepared by reaction of 2-(3-piperidin-4-ylmethyl-[1,2,4]oxadiazol-5-yl)furo[3,2-c]pyridine (Preparation 12) with the appropriate alcohol and triphosgene employing procedures similar to those delineated in Example 92.

TABLE 7

| Eg | Structure | Name | RT (min) | m/z $(ES^+)$ |
|---|---|---|---|---|
| 69 | 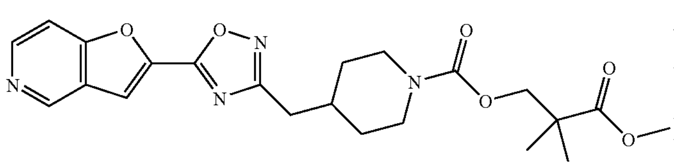 | 4-(5-Furo[3,2-c]pyridin-2-yl-[1,2,4]oxadiazol-3-ylmethyl)piperidine-1-carboxylic acid 2-methoxycarbonyl-2-methylpropyl ester | 3.11 | 443.1 $[M + H]^+$ |

TABLE 7-continued

| Eg | Structure | Name | RT (min) | m/z (ES+) |
|---|---|---|---|---|
| 70 | 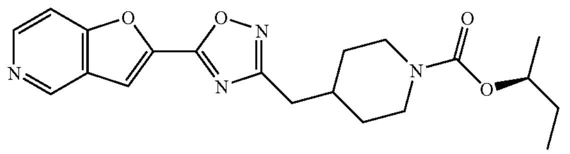 | 4-(5-Furo[3,2-c]pyridin-2-yl-[1,2,4]oxadiazol-3-ylmethyl)piperidine-1-carboxylic acid (S)-sec-butyl ester | 3.26 | 385.1 [M + H]+ |
| 71 | 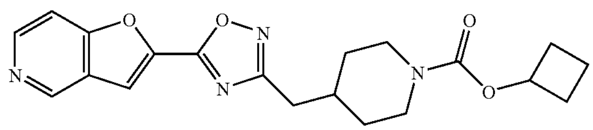 | 4-(5-Furo[3,2-c]pyridin-2-yl-[1,2,4]oxadiazol-3-ylmethyl)piperidine-1-carboxylic acid cyclobutyl ester | 3.15 | 383.1 [M + H]+ |
| 72 | 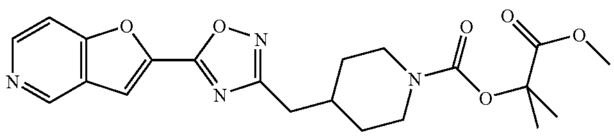 | 4-(5-Furo[3,2-c]pyridin-2-yl-[1,2,4]oxadiazol-3-ylmethyl)piperidine-1-carboxylic acid 1-methoxycarbonyl-1-methylethyl ester | 3.02 | 429.1 [M + H]+ |
| 73 | 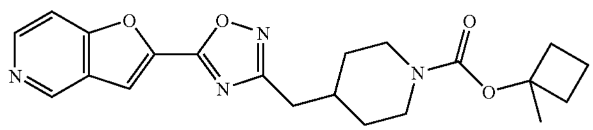 | 4-(5-Furo[3,2-c]pyridin-2-yl-[1,2,4]oxadiazol-3-ylmethyl)piperidine-1-carboxylic acid 1-methyl-cyclobutyl ester | 3.36 | 397.1 [M + H]+ |
| 74 | 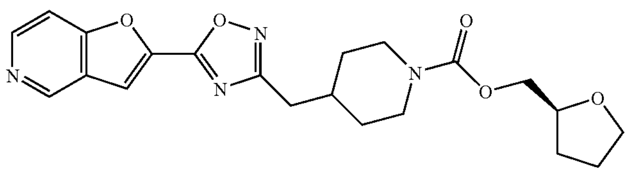 | 4-(5-Furo[3,2-c]pyridin-2-yl-[1,2,4]oxadiazol-3-ylmethyl)piperidine-1-carboxylic acid (R)-tetrahydrofuran-2-ylmethyl ester | 2.77 | 413.1 [M + H]+ |
| 75 | 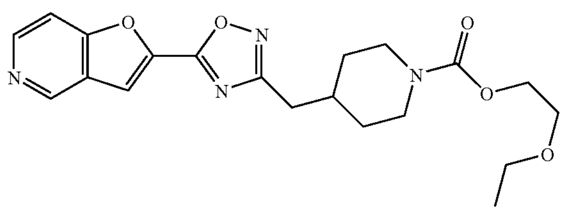 | 4-(5-Furo[3,2-c]pyridin-2-yl-[1,2,4]oxadiazol-3-ylmethyl)piperidine-1-carboxylic acid 2-ethoxy-ethyl ester | 2.77 | 401.1 [M + H]+ |
| 76 | 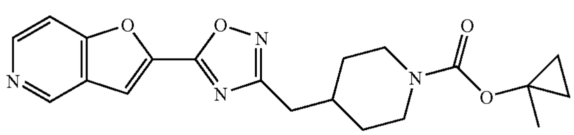 | 4-(5-Furo[3,2-c]pyridin-2-yl-[1,2,4]oxadiazol-3-ylmethyl)piperidine-1-carboxylic acid 1-methyl-cyclopropyl ester | 3.01 | 383.1 [M + H]+ |

Example 77

2-[3-(1-Pyrimidin-2-ylpiperidin-4-ylmethyl)-[1,2,4]oxadiazol-5-yl]furo[3,2-c]pyridine

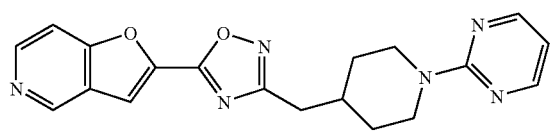

DBU (53 ΔL, 352 Amos) was added to a stirred solution of 2-(3-piperidin-4-ylmethyl-[1,2,4]oxadiazol-5-yl)furo[3,2-c]pyridine (Preparation 12, 50 mg, 176 μmol) and 2-bromopyrimidine (31 mg, 193 μmol) in dioxane (1 mL) at 20° C. After 2 d, the solvent was removed in vacuo, then the residue was purified by chromatography (MeOH—CH$_2$Cl$_2$, 1:19) to yield the title compound: RT=2.64 min; m/z (ES+)=363.1 [M+H]+.

Example 78

4-(5-Furo[3,2-c]pyridin-2-yl-[1,2,4]oxadiazol-3-ylmethyl)piperidine-1-carboxylic acid 1-carboxy-1-methylethyl ester

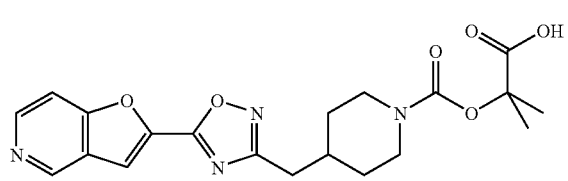

A stirred solution of 4-(5-furo[3,2-c]pyridin-2-yl-[1,2,4]oxadiazol-3-ylmethyl)piperidine-1-carboxylic acid 1-methoxycarbonyl-1-methylethyl ester (Example 72, 43 mg, 100 µmol) in THF-H$_2$O (3:1, 2 mL) was treated with LiOH.H$_2$O (9 mg, 220 µmol). After 16 h, the THF was evaporated in vacuo, then the remainder was diluted with H$_2$O (2 mL), before being washed with EtOAc (2×5 mL). The aqueous phase was neutralised with 1 M HCl, then the mixture was extracted with EtOAc (3×10 mL). The combined EtOAc extracts were dried (MgSO$_4$), filtered, and concentrated to furnish the title compound: RT=2.74 min; m/z (ES$^+$)=415.1 [M+H]$^+$.

Example 79

4-(5-Furo[3,2-c]pyridin-2-yl-[1,2,4]oxadiazol-3-ylmethyl)piperidine-1-carboxylic acid 2-carboxy-2-methylpropyl ester

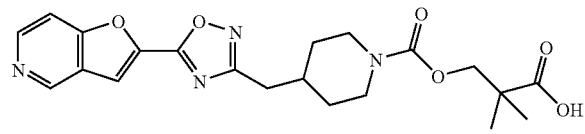

Saponification of 4-(5-furo[3,2-c]pyridin-2-yl-[1,2,4]oxadiazol-3-ylmethyl)piperidine-1-carboxylic acid 2-methoxycarbonyl-2-methylpropyl ester (Example 69) by the protocol outlined in Example 78 yielded the title compound: RT=2.74 min; m/z (ES$^+$)=429.1 [M+H]$^+$.

Example 80

4-[5-(5-Oxyfuro[3,2-c]pyridin-2-yl)-[1,2,4]oxadiazol-3-ylmethyl]piperidine-1-carboxylic acid tert-butyl ester

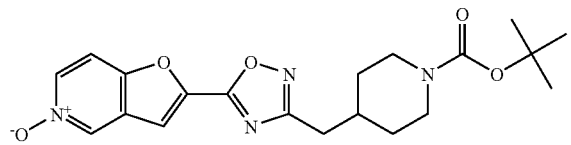

A stirred solution of 4-(5-furo[3,2-c]pyridin-2-yl-[1,2,4]oxadiazol-3-ylmethyl)-piperidine-1-carboxylic acid tert-butyl ester (Example 44, 70 mg, 180 µmol) in anhydrous CH$_2$Cl$_2$ (5 mL) was treated with mCPBA (54 mg, 70% pure, 220 µmol). After 1 h, more mCPBA (5 mg, 70% pure, 20 µmol) was added, then stirring was continued for 16 h at 20° C. The mixture was concentrated under reduced pressure, then the residue was purified by flash chromatography (EtOAc then CH$_2$Cl$_1$-MeOH, 19:1) to afford the title compound: RT=2.51 min; m/z (ES$^+$)=401.4 [M+H]$^+$.

Example 81

4-[2-(5-Oxyfuro[3,2-c]pyridin-2-yl)ethyl]piperidine-1-carboxylic acid tert-butyl ester

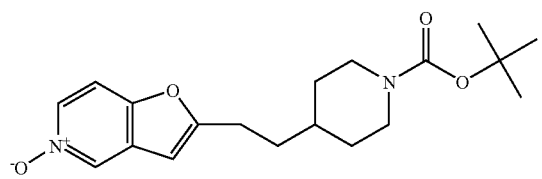

4-(2-Furo[3,2-c]pyridin-2-ylethyl)piperidine-1-carboxylic acid tert-butyl ester (Example 18) was oxidised with mCPBA, employing a procedure similar to that outlined in Example 80, to furnish the title compound: RT=2.64 min; m/z (ES$^+$)=347.4 [M+H]$^+$.

Example 82

4-[5-(4-Cyanofuro[3,2-c]pyridin-2-yl)-[1,2,4]oxadiazol-3-ylmethyl]piperidine-1-carboxylic acid tert-butyl ester

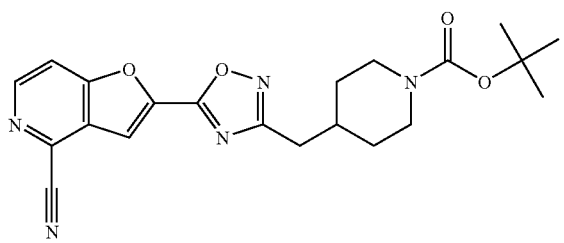

A stirred solution of 4-[5-(5-oxyfuro[3,2-c]pyridin-2-yl)-[1,2,4]oxadiazol-3-ylmethyl]-piperidine-1-carboxylic acid tert-butyl ester (Example 80, 50 mg, 130 µmol) in anhydrous CH$_2$Cl$_2$ (3 mL) was treated with TMS-CN (22 µL, 160 µmol) and Me$_2$NC(O)Cl (dropwise, 15 mL, 160 µmol). After 16 h, the reaction was treated with H$_2$O (15 mL), before being extracted with CH$_2$Cl$_2$ (3×20 mL). The CH$_2$Cl$_2$ extracts were combined, dried (MgSO$_4$), filtered, and concentrated in vacuo. The residue was purified by flash chromatography (EtOAc IH, 2:3) to yield the title compound: RT=3.35 min; m/z (ES$^+$)=354.3 [M+2H-t-Bu]$^+$.

The nitrites listed in Table 8 were prepared from the appropriate starting material employing procedures similar to those described in Examples 80 and 82.

TABLE 8

| Eg | Structure | Name | RT (min) | m/z (ES⁺) |
|---|---|---|---|---|
| 83 | 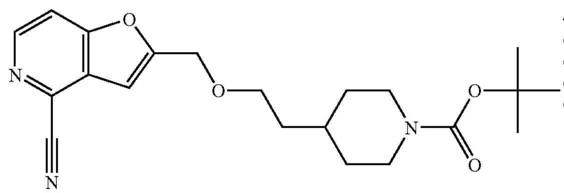 | 4-[2-(4-Cyanofuro[3,2-c]pyridin-2-ylmethoxy)-ethyl]piperidine-1-carboxylic acid tert-butyl ester | 3.90 | 386.3 [M + H]⁺ |
| 84 | 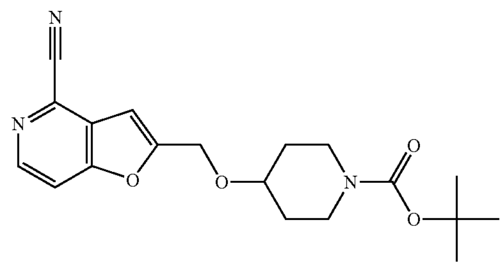 | 4-[2-(4-Cyanofuro[3,2-c]pyridin-2-yl)ethyl]-piperidine-1-carboxylic acid tert-butyl ester | 3.49 | 300.3 [M + 2H − t-Bu] |
| 85 | 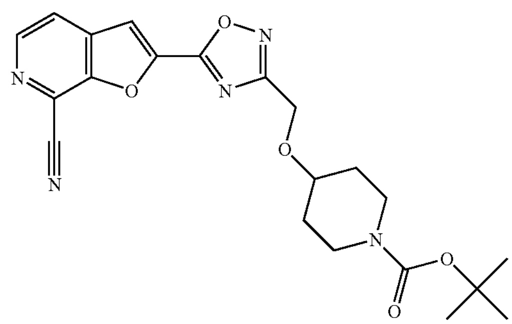 | 4-[5-(7-Cyanofuro[2,3-c]pyridin-2-yl)-[1,2,4]oxadiazol-3-ylmethoxy]piperidine-1-carboxylic acid tert-butyl ester | 3.87 | 426.2 [M + H]⁺ |
| 86 | 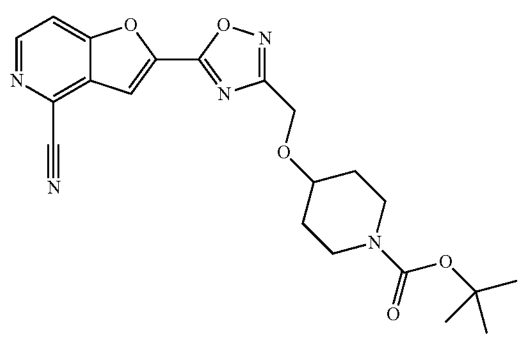 | 4-[5-(4-Cyanofuro[3,2-c]pyridin-2-yl)-[1,2,4]oxadiazol-3-ylmethoxy]piperidine-1-carboxylic acid tert-butyl ester | 3.81 | 426.2 [M + H]⁺ |
| 87 | 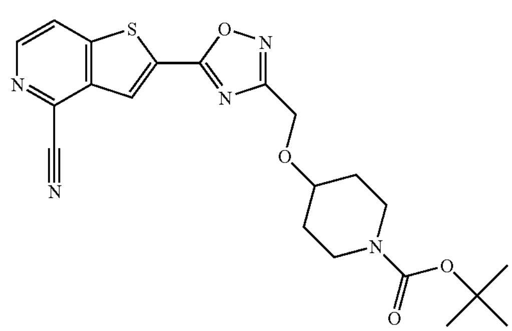 | 4-[5-(4-Cyanothieno[3,2-c]pyridin-2-yl)-[1,2,4]oxadiazol-3-ylmethoxy]piperidine-1-carboxylic acid tert-butyl ester | 3.97 | 442.1 [M + H]⁺ |

TABLE 8-continued

| Eg | Structure | Name | RT (min) | m/z (ES+) |
|---|---|---|---|---|
| 88 | 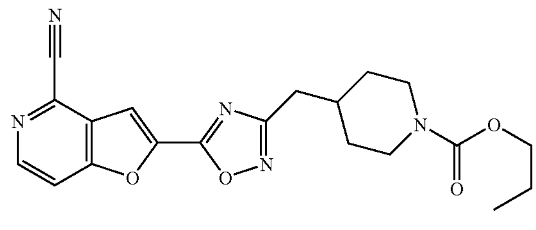 | 4-[5-(4-Cyanofuro[3,2-c]pyridin-2-yl)-[1,2,4]oxadiazol-3-ylmethoxy]piperidine-1-carboxylic acid propyl ester | 3.74 | 396.1 [M + H]+ |
| 89 | 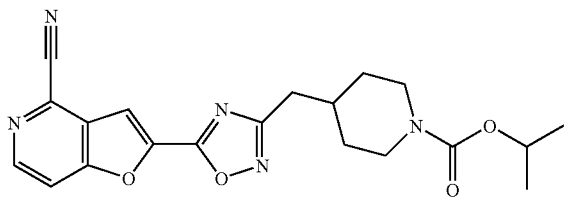 | 4-[5-(4-Cyanofuro[3,2-c]pyridin-2-yl)-[1,2,4]oxadiazol-3-ylmethyl]piperidine-1-carboxylic acid isopropyl ester | 3.65 | 396.1 [M + H]+ |

Example 90

4-[5-(4-Cyanofuro[3,2-c]pyridin-2-yl)-[1,2,4]oxadiazol-3-ylmethyl]piperidine-1-carboxylic acid isobutyl ester

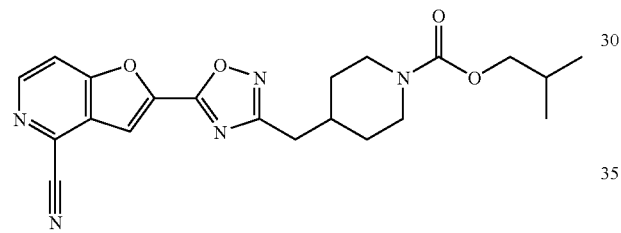

i-BuOCOCl (19 µL, 146 µmol) and NEt₃ (15 µL, 107 µmol) were added to a stirred solution of 2-(3-piperidin-4-ylmethyl-[1,2,4]oxadiazol-5-yl)furo[3,2-c]pyridine-4-carbonitrile (Preparation 15, 30 mg, 97 µmol) in anhydrous $CH_2Cl_2$ (1.5 mL). After 30 min, the reaction mixture was diluted with $Et_2O$ (10 mL) and $H_2O$ (2 mL). The organic layer was washed with saturated aqueous $Na_2CO_3$ (2 mL), $H_2O$ (2 mL), and brine (2 mL), before being dried ($MgSO_4$). Filtration, solvent evaporation, and column chromatography (EtOAc) furnished the title compound: RT=3.95 min; m/z (ES+)=410.1 [M+H]+.

Example 91

4-[5-(4-Cyanofuro[3,2-c]pyridin-2-yl)-[1,2,4]oxadiazol-3-ylmethyl]piperidine-1-carboxylic acid ethyl ester

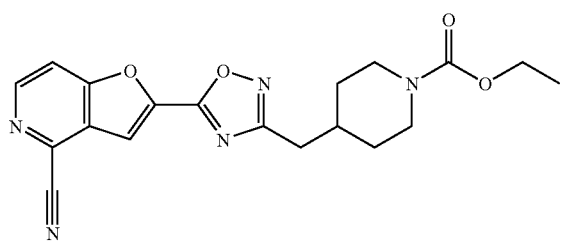

ETOCOCl was reacted with 2-(3-piperidin-4-ylmethyl-[1,2,4]oxadiazol-5-yl)furo[3,2-c]pyridine-4-carbonitrile (Preparation 15, 30 mg, 97 µmol), by the protocol described for Example 90, to furnish the title compound: RT=3.56 min; m/z (ES+)=382.1 [M+H]+.

Example 92

4-[5-(4-Cyanofuro[3,2-c]pyridin-2-yl)-[1,2,4]oxadiazol-3-ylmethyl]piperidine-1-carboxylic acid cyclobutyl ester

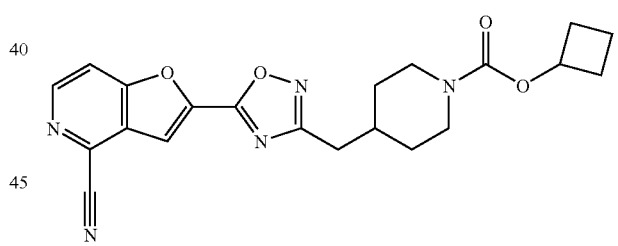

A mixture of cyclobutyl alcohol (32.6 mg, 452 µmol), triphosgene (44.7 mg, 151 µmol), anhydrous THF (4 mL), and NEt₃ (91.6 mg, 905 µmol) was stirred for 30 min. This mixture was added to a stirred solution of 2-(3-piperidin-4-ylmethyl-[1,2,4]oxadiazol-5-yl)furo[3,2-c]pyridine-4-carbonitrile (Preparation 15, 35 mg, 113 µmol) in anhydrous THF (2 mL). After 30 min, the reaction mixture was treated with $CH_2Cl_2$ (20 mL) and $H_2O$ (10 mL), then, after thorough mixing, the organic layer was separated using a fritted hydrophobic filter. The aqueous phase was extracted with $CH_2Cl_2$ (10 mL), the $CH_2Cl_2$ layer being isolated by means of a fritted hydrophobic filter. The combined $CH_2Cl_2$ solutions were evaporated, then the residue was purified by column chromatography (EtOAc-IH, 1:1) to furnish the title compound: RT=3.84 min; m/z (ES+)=408.1 [M+H]+.

The carbamate esters listed in Table 9 were prepared from the appropriate amine and alcohol employing the procedure described in Example 92.

TABLE 9

| Eg | Structure | Name | RT (min) | m/z (ES+) |
|---|---|---|---|---|
| 93 | 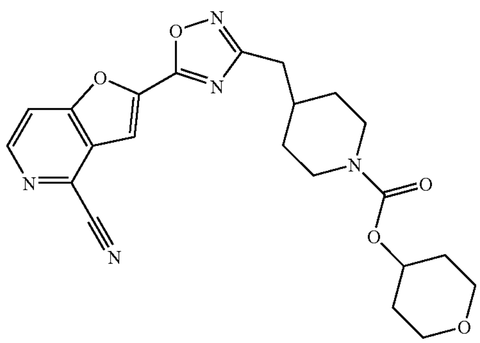 | 4-[5-(4-Cyanofuro[3,2-c]pyridin-2-yl)-[1,2,4]oxadiazol-3-ylmethyl]piperidine-1-carboxylic acid tetrahydropyran-4-yl ester | 3.52 | 438.1 [M + H]+ |
| 94 | 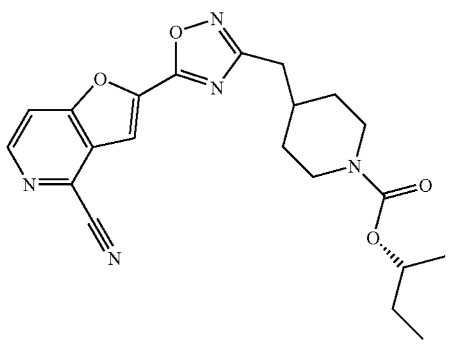 | 4-[5-(4-Cyanofuro[3,2-c]pyridin-2-yl)-[1,2,4]oxadiazol-3-ylmethyl]piperidine-1-carboxylic acid (R)-sec-butyl ester | 3.94 | 410.1 [M + H]+ |
| 95 | 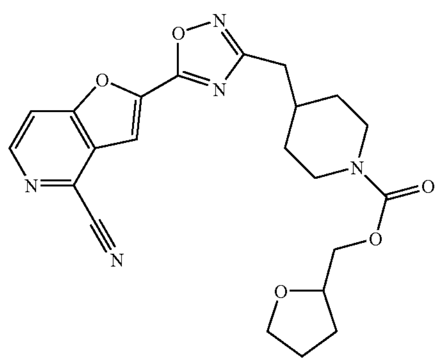 | 4-[5-(4-Cyanofuro[3,2-c]pyridin-2-yl)-[1,2,4]oxadiazol-3-ylmethyl]piperidine-1-carboxylic acid tetrahydrofuran-2-ylmethyl ester | 3.45 | 438.1 [M + H]+ |
| 96 | 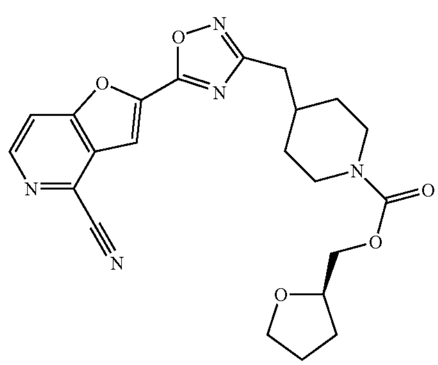 | 4-[5-(4-Cyanofuro[3,2-c]pyridin-2-yl)-[1,2,4]oxadiazol-3-ylmethyl]piperidine-1-carboxylic acid (R)-tetrahydrofuran-2-ylmethyl ester | 3.47 | 438.1 [M + H]+ |

TABLE 9-continued

| Eg | Structure | Name | RT (min) | m/z (ES+) |
|---|---|---|---|---|
| 97 | 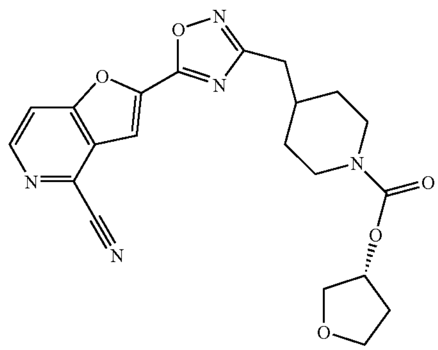 | 4-[5-(4-Cyanofuro[3,2-c]pyridin-2-yl)-[1,2,4]oxadiazol-3-ylmethyl]piperidine-1-carboxylic acid (R)-tetrahydrofuran-3-yl ester | 3.36 | 424.1 [M + H]+ |
| 98 | 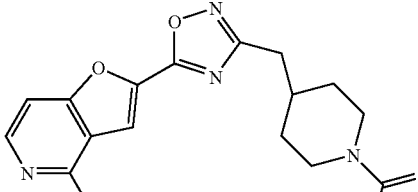 | 4-[5-(4-Cyanofuro[3,2-c]pyridin-2-yl)-[1,2,4]oxadiazol-3-ylmethyl]piperidine-1-carboxylic acid tetrahydrothiopyran-4-yl ester | 3.79 | 454.1 [M + H]+ |
| 99 | 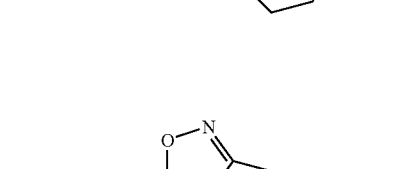 | 4-[5-(4-Cyanofuro[3,2-c]pyridin-2-yl)-[1,2,4]oxadiazol-3-ylmethyl]piperidine-1-carboxylic acid 1-methoxycarbonyl-1-methylethyl ester | 3.74 | 454.1 [M + H]+ |
| 100 | 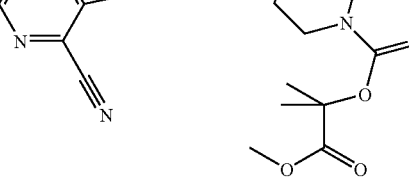 | 4-[5-(4-Cyanofuro[3,2-c]pyridin-2-yl)-[1,2,4]oxadiazol-3-ylmethyl]piperidine-1-carboxylic acid methoxycarbonylmethyl ester | 3.40 | 426.1 [M + H]+ |

TABLE 9-continued

| Eg | Structure | Name | RT (min) | m/z (ES+) |
|---|---|---|---|---|
| 101 | 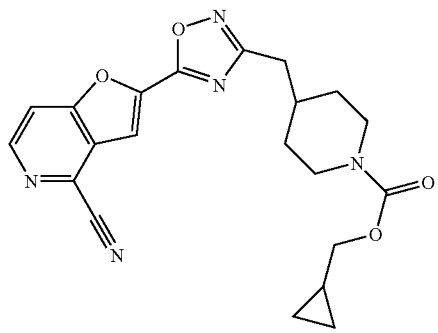 | 4-[5-(4-Cyanofuro[3,2-c]pyridin-2-yl)-[1,2,4]oxadiazol-3-ylmethyl]piperidine-1-carboxylic acid cyclopropylmethyl ester | 3.84 | 408.1 [M + H]+ |
| 102 | 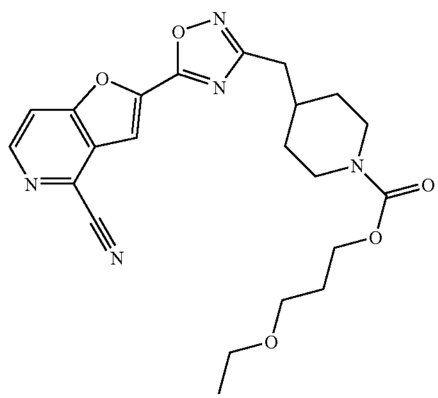 | 4-[5-(4-Cyanofuro[3,2-c]pyridin-2-yl)-[1,2,4]oxadiazol-3-ylmethyl]piperidine-1-carboxylic acid 3-ethoxy-propyl ester | 3.49 | 440.1 [M + H]+ |
| 103 | 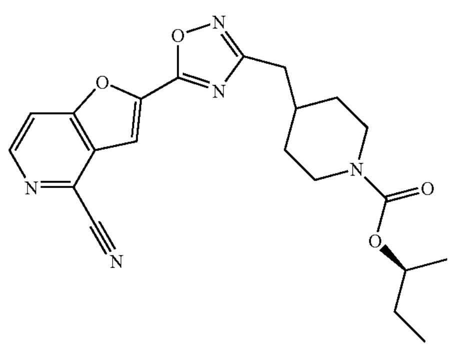 | 4-[5-(4-Cyanofuro[3,2-c]pyridin-2-yl)-[1,2,4]oxadiazol-3-ylmethyl]piperidine-1-carboxylic acid (S)-sec-butyl ester | 3.92 | 410.1 [M + H]+ |
| 104 | 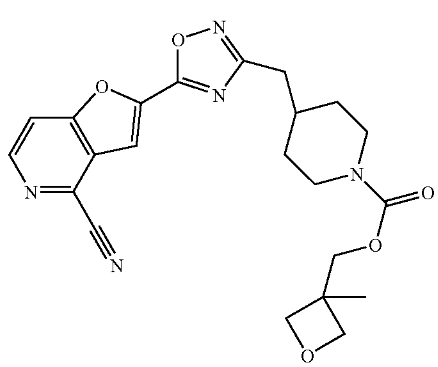 | 4-[5-(4-Cyanofuro[3,2-c]pyridin-2-yl)-[1,2,4]oxadiazol-3-ylmethyl]piperidine-1-carboxylic acid 3-methyl-oxetan-3-ylmethyl ester | 3.34 | 438.1 [M + H]+ |

TABLE 9-continued

| Eg | Structure | Name | RT (min) | m/z (ES+) |
|---|---|---|---|---|
| 105 | 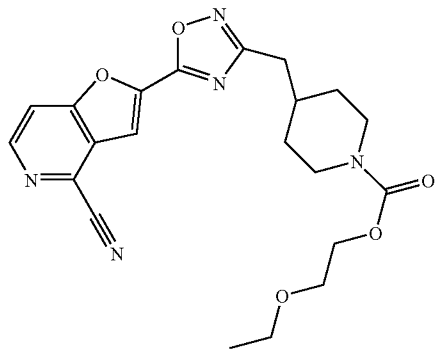 | 4-[5-(4-Cyanofuro[3,2-c]pyridin-2-yl)-[1,2,4]oxadiazol-3-ylmethyl]piperidine-1-carboxylic acid 2-ethoxy-ethyl ester | 3.44 | 426.1 [M + H]+ |
| 106 | 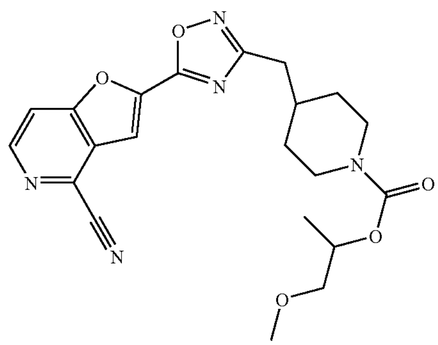 | 4-[5-(4-Cyanofuro[3,2-c]pyridin-2-yl)-[1,2,4]oxadiazol-3-ylmethyl]piperidine-1-carboxylic acid 2-methoxy-1-methylethyl ester | 3.51 | 426.1 [M + H]+ |
| 107 | 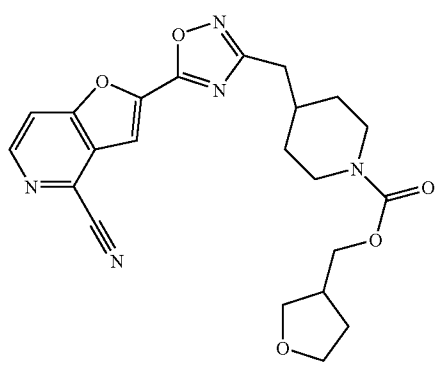 | 4-[5-(4-Cyanofuro[3,2-c]pyridin-2-yl)-[1,2,4]oxadiazol-3-ylmethyl]piperidine-1-carboxylic acid tetrahydrofuran-3-ylmethyl ester | 3.49 | 438.1 [M + H]+ |
| 108 | 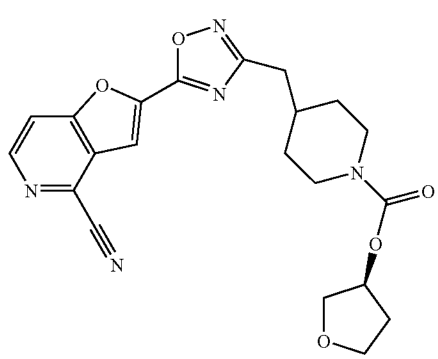 | 4-[5-(4-Cyanofuro[3,2-c]pyridin-2-yl)-[1,2,4]oxadiazol-3-ylmethyl]piperidine-1-carboxylic acid (S)-tetrahydrofuran-3-yl ester | 3.30 | 424.1 [M + H]+ |

TABLE 9-continued

| Eg | Structure | Name | RT (min) | m/z (ES⁺) |
|---|---|---|---|---|
| 109 | 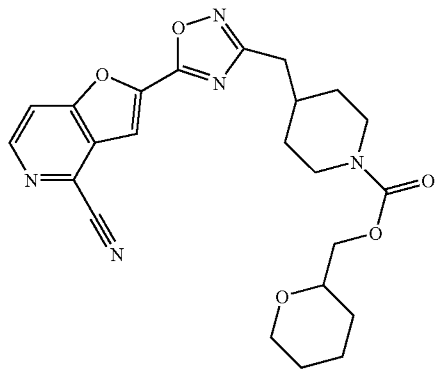 | 4-[5-(4-Cyanofuro[3,2-c]pyridin-2-yl)-[1,2,4]oxadiazol-3-ylmethyl]piperidine-1-carboxylic acid tetrahydropyran-2-ylmethyl ester | 3.70 | 452.1 [M + H]⁺ |
| 110 | 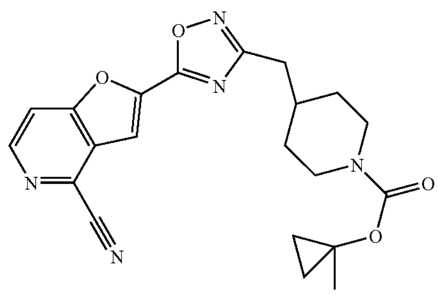 | 4-[5-(4-Cyanofuro[3,2-c]pyridin-2-yl)-[1,2,4]oxadiazol-3-ylmethyl]piperidine-1-carboxylic acid 1-methyl-cyclopropyl ester | 3.76 | 408.1 [M + H]⁺ |
| 111 | 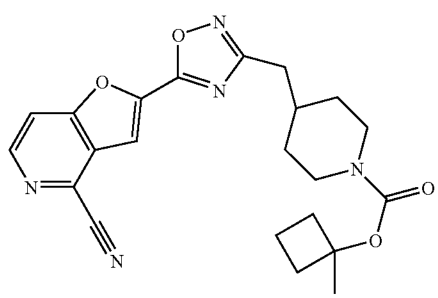 | 4-[5-(4-Cyanofuro[3,2-c]pyridin-2-yl)-[1,2,4]oxadiazol-3-ylmethyl]piperidine-1-carboxylic acid 1-methyl-cyclobutyl ester | 3.87 | 422.1 [M + H]⁺ |
| 112 | 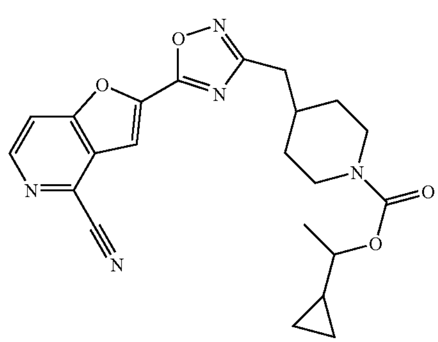 | 4-[5-(4-Cyanofuro[3,2-c]pyridin-2-yl)-[1,2,4]oxadiazol-3-ylmethyl]piperidine-1-carboxylic acid 1-cyclopropylethyl ester | 3.87 | 422.1 [M + H]⁺ |

TABLE 9-continued

| Eg | Structure | Name | RT (min) | m/z (ES+) |
|---|---|---|---|---|
| 113 | 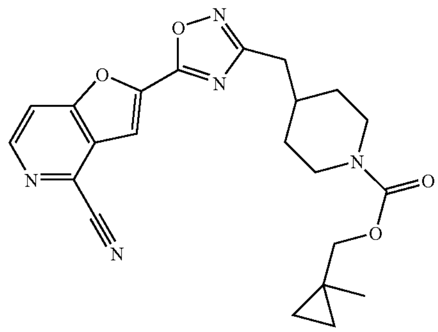 | 4-[5-(4-Cyanofuro[3,2-c]pyridin-2-yl)-[1,2,4]oxadiazol-3-ylmethyl]piperidine-1-carboxylic acid 1-methyl-cyclopropylmethyl ester | 3.82 | 422.1 [M + H]+ |
| 114 | 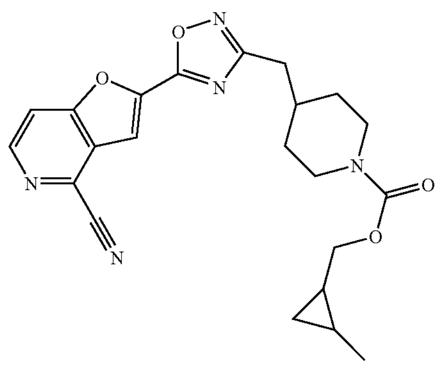 | 4-[5-(4-Cyanofuro[3,2-c]pyridin-2-yl)-[1,2,4]oxadiazol-3-ylmethyl]piperidine-1-carboxylic acid 2-methyl-cyclopropylmethyl ester | 3.86 | 422.1 [M + H]+ |
| 115 | 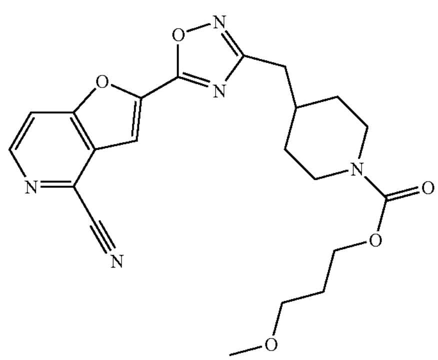 | 4-[5-(4-Cyanofuro[3,2-c]pyridin-2-yl)-[1,2,4]oxadiazol-3-ylmethyl]piperidine-1-carboxylic acid 3-methoxypropyl ester | 3.51 | 426.1 [M + H]+ |
| 116 | 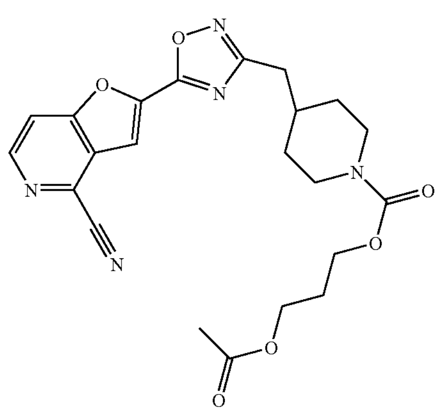 | 4-[5-(4-Cyanofuro[3,2-c]pyridin-2-yl)-[1,2,4]oxadiazol-3-ylmethyl]piperidine-1-carboxylic acid 3-acetoxypropyl ester | 3.45 | 454.1 [M + H]+ |

TABLE 9-continued

| Eg | Structure | Name | RT (min) | m/z (ES+) |
|---|---|---|---|---|
| 117 | 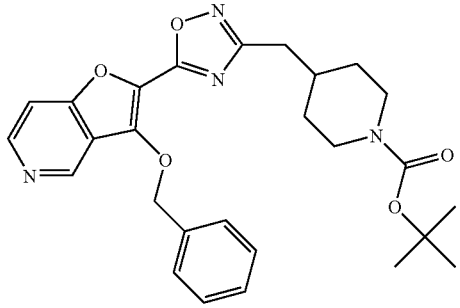 | 4-[5-(4-Cyanofuro[3,2-c]pyridin-2-yl)-[1,2,4]oxadiazol-3-ylmethyl]piperidine-1-carboxylic acid oxetan-3-yl ester | 3.36 | 410.1 [M + H]+ |

Examples 118 and 119

4-[5-(4-Cyanofuro[3,2-c]pyridin-2-yl)-[1,2,4]oxadiazol-3-ylmethyl]piperidine-1-carboxylic acid 1-oxo-hexahydro-1λ⁴-thiopyran-4-yl ester and 4-[5-(4-Cyanofuro[3,2-c]pyridin-2-yl)-[1,2,4]oxadiazol-3-ylmethyl]piperidine-1-carboxylic acid 1,1-dioxo-hexahydro-1λ⁶-thiopyran-4-yl ester

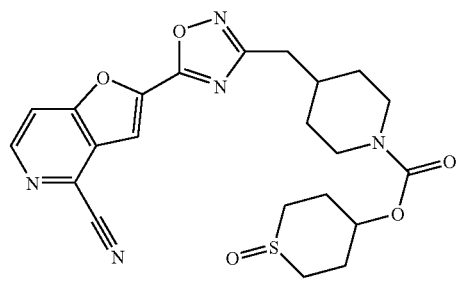

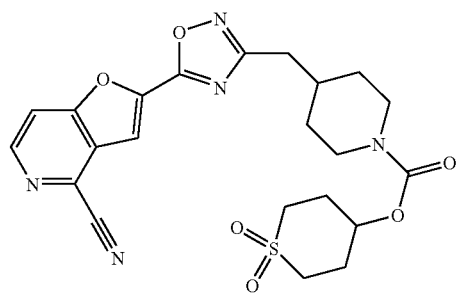

mCPBA (22 mg, 77% pure, 99 μmol) was added to a stirred solution of 4-[5-(4-cyano-furo[3,2-c]pyridin-2-yl)-[1,2,4]oxadiazol-3-ylmethyl]piperidine-1-carboxylic acid tetrahydro-thiopyran-4-yl ester (Example 98, 30 mg, 66 μmol) in $CH_2Cl_2$ (1 mL). After 16 h, the reaction mixture was washed with saturated aqueous $NaHCO_3$ (1 mL). The aqueous phase was extracted with $CH_2Cl_2$ (2 mL), then the combined organic extracts were dried ($MgSO_4$) and filtered before being loaded onto a $SiO_2$ column. Elution of the column with EtOAc and further purification by RP-HPLC furnished the title sulfoxide: RT=3.11 min; m/z (ES+)=470.1 [M+H]+. Subsequent elution of the $SiO_2$ column with THF yielded the title sulfone: RT=3.27 min; m/z (ES+)=486.1 [M+H]+.

Example 120

4-[5-(3-Benzyloxyfuro[3,2-c]pyridin-2-yl)-[1,2,4]oxadiazol-3-ylmethyl]-piperidine-1-carboxylic acid tert-butyl ester

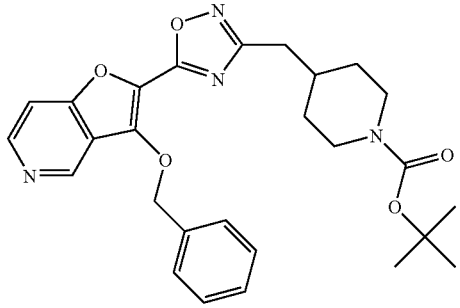

NaH (60% dispersion in mineral oil, 75 mg, 1.88 mmol) was added to a solution of 3-benzyloxyfuro[3,2-c]pyridine-2-carboxylic acid ethyl ester (Preparation 16, 510 mg, 1.71 mmol) and 4-(N-hydroxycarbamimidoylmethyl)piperidine-1-carboxylic acid tert-butyl ester (485 mg, 1.88 mmol) in anhydrous THF. The mixture was heated under reflux for 90 min, before being cooled down to ambient temperature and poured into $H_2O$. The mixture was extracted twice with EtOAc, then the combined organic extracts were washed with brine, before being dried ($MgSO_4$). Filtration, solvent evaporation, and column chromatography (EtOAc) furnished the title compound: RT=4.12 min; m/z (ES+)=491.1 [M+H]+.

Example 121

4-[5-(3-Hydroxyfuro[3,2-c]pyridin-2-yl)[1,2,4]oxadiazol-3-ylmethyl]-piperidine-1-carboxylic acid tert-butyl ester

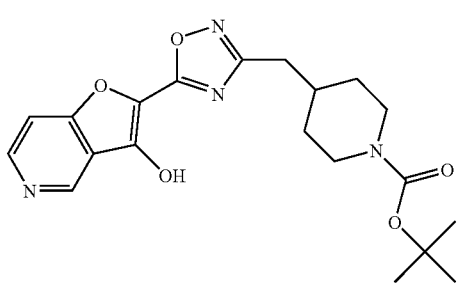

A solution of 4-[5-(3-benzyloxyfuro[3,2-c]pyridin-2-yl)-[1,2,4]oxadiazol-3-ylmethyl]-piperidine-1-carboxylic acid tert-butyl ester (Example 120, 200 mg, 500 µmol) and Pd (10% on C, 10 mg) in EtOH (10 mL) was stirred under a H$_2$ atmosphere for 2.5 h. The mixture was diluted with CH$_2$Cl$_2$, to solubilise the product, before being filtered through celite. The filtrate was concentrated to furnish the title compound: RT=2.87 min; m/z (ES$^+$)=401.1 [M+H]$^+$.

Example 122

4-[5-(4-Methylfuro[3,2-c]pyridin-2-yl)-[1,2,4]oxadiazol-3-ylmethyl]piperidine-1-carboxylic acid tert-butyl ester

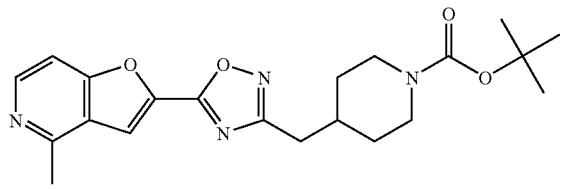

A stirred solution of 4-[5-(5-oxyfuro[3,2-c]pyridin-2-yl)-[1,2,4]oxadiazol-3-ylmethyl]piperidine-1-carboxylic acid tert-butyl ester (Example 80, 240 mg, 0.60 mmol) in anhydrous DMF-CH$_2$Cl$_2$ (5:4, 9 mL) was treated with EtI (53 µL, 0.66 mmol) at 0° C. The mixture was allowed to warm to room temperature, before being stirred for 16 h. More EtI (106 µL, 1.32 mmol) was added, then the mixture was stirred for 3 d. The reaction mixture was concentrated in vacuo, then the residue was dissolved in anhydrous DMF (5 mL), before being treated with EtI (106 µL, 1.32 mmol). The mixture was stirred for 16 h, then more EtI (53 mL, 0.66 mmol) was added. After 24 h, the reaction mixture was concentrated in vacuo, then the residue was purified by flash chromatography (CH$_2$Cl$_2$-MeOH, 92:8) to furnish 2-[3-(1-tert-butoxycarbonylpiperidin-4-ylmethyl)-[1,2,4]oxadiazol-5-yl]-5-ethoxyfuro[3,2-c]pyridin-5-ium iodide: m/z (ES$^+$)=429.1 [M]$^+$. A stirred solution of this compound (100 mg, 0.18 mmol) in anhydrous THF-Et$_2$O (1:1, 4 mL) was treated with MeMgI (66 ILL of a 3 M solution in Et$_2$O, 0.20 mmol). After 4 h, more MeMgI (66 µL of a 3 M solution in Et$_2$O, 0.20 mmol) was added, then stirring was continued for 16 h. The reaction mixture was diluted with EtOAc (20 mL), before being washed with saturated aqueous NaHCO$_3$ (10 mL) and brine (10 mL). After drying (MgSO$_4$), the solution was filtered and concentrated, then the residue was purified by flash chromatography (EtOAc) then RP-HPLC to yield the title compound: RT=2.99 min; m/z (ES$^+$)=399.1 [M+H]$^+$.

Example 123

4-[5-(7-Iodofuro[3,2-c]pyridin-2-yl)-[1,2,4]oxadiazol-3-ylmethyl]piperidine-1-carboxylic acid tert-butyl ester

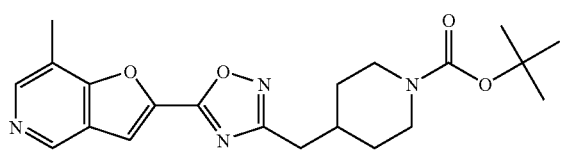

Condensation of 7-iodofuro[3,2-c]pyridine-2-carboxylic acid (Preparation 20, 423 mg, 1.46 mmol) with 4-(N-hydroxycarbaminidoylmethyl)piperidine-1-carboxylic acid tert-butyl ester (414 mg, 1.61 mmol), employing a procedure similar to that outlined in Preparation 14, afforded the title compound: RT=3.99 min; m/z (ES$^+$)=511.0 [M+H]$^+$.

Example 124

4-Chloro-2-[3-(1-pyrimidin-2-ylpiperidin yloxymethyl)-[1,2,4]oxadiazol-5-yl]furo[3,2-c]pyridine

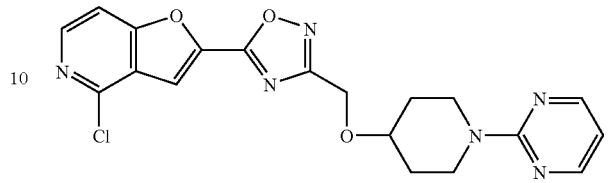

A stirred solution of 4-[5-(4-chlorofuro[3,2-c]pyridin-2-yl)-[1,2,4]oxadiazol-3-ylmethoxy]piperidine-1-carboxylic acid tert-butyl ester (Example 57, 150 mg, 346 µmol) in CH$_2$Cl$_2$ (4 mL) was treated with H$_2$O (6 µL) and TFA (1.5 mL). After 1 h, the reaction was concentrated in vacuo, then the excess TFA was removed through azeotropic distillation with PhMe under reduced pressure. The remainder was partitioned between EtOAc and 2M NaOH. The aqueous phase was extracted further with EtOAc, then the combined EtOAc extracts were washed with brine and dried (MgSO$_4$). Filtration and solvent evaporation furnished 4-chloro-2-[3-(piperidin-4-yloxymethyl)-[1,2,4]oxadiazol-5-yl]furo[3,2-c]pyridine: m/z (ES$^+$)=335.1 [M+H]$^+$. A mixture of this amine (105 mg, 315 µmol), 2-bromopyrimidine (55 mg, 346 µmol) and DBU (95 µL, 630 µmol) in dioxane (2 mL) was stirred at ambient temperature for 16 h. The reaction was concentrated and the residue purified by column chromatography (EtOAc-IH, 3:7) to yield the title compound: RT=3.40 min; m/z (ES$^+$)=413.1 [M+H]$^+$.

Example 125

2-(3-((1-(3-Methoxypyridin-2-yl)piperidin-4-yl)methyl)-[1,2,4]-oxadiazol-5-yl)furo[3,2-c]pyridine

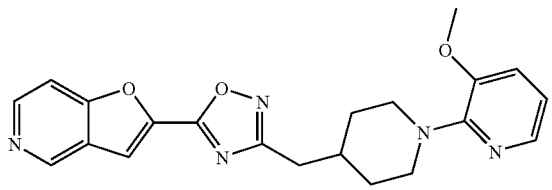

2-(3-Piperidin-4-ylmethyl-[1,2,4]oxadiazol-5-yl)furo[3,2-c]pyridine (Preparation 12, 50 mg, 0.176 mmol) and 3-methoxy-2-nitropyridine (41 mg, 0.264 mmol) were shaken in DMSO (1 mL) at 100° C. for 20 h. The reaction mixture was allowed to cool to room temperature, before being acidified with AcOH. Purification by RP-HPLC yielded the title compound: RT=4.99 min; m/z (ES$^+$)=392.4 [M+H]$^+$.

Example 126

Ethyl 6-(4-((5-(furo[3,2-c]pyridin-2-yl)-[1,2,4]-oxadiazol-3-yl)methyl)piperidin-1-yl)nicotinate

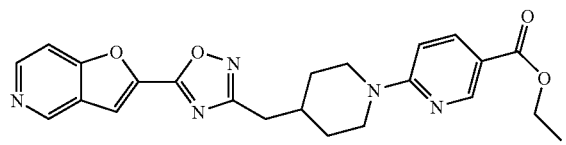

2-(3-Piperidin-4-ylmethyl-[1,2,4]oxadiazol-5-yl)furo[3,2-c]pyridine (Preparation 12, 50 mg, 0.176 mmol), ethyl 6-chloronicotinate (49 mg, 0.264 mmol) and DBU (40 mg, 0.264 mmol) were shaken in DMSO (1 mL) at 100° C. for 20 h. The reaction mixture was allowed to cool to room temperature, before being acidified with AcOH. Purification by RP-HPLC yielded the title compound: RT=5.74 min; m/z (ES⁺)=434.4 [M+H]⁺.

The compounds listed in Table 10 were prepared using the procedure described in Example 126 at temperatures of 60-150° C.

TABLE 10

| Eg | Structure | Name | RT (min) | m/z (ES⁺) |
|---|---|---|---|---|
| 127 | 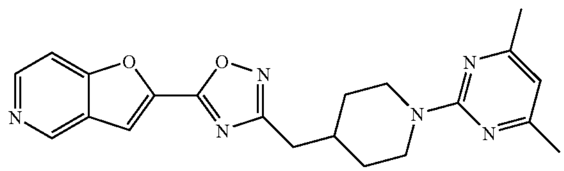 | 2-{3-[1-(4,6-Dimethyl-pyrimidin-2-yl)piperidin-4-ylmethyl]-[1,2,4]oxadiazol-5-yl}-furo[3,2-c]pyridine | 5.84 | 391.1 [M + H]⁺ |
| 128 | 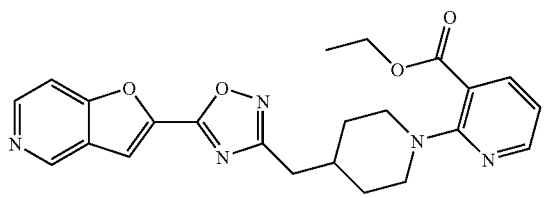 | 4-(5-Furo[3,2-c]pyridin-2-yl-[1,2,4]oxadiazol-3-ylmethyl)-3,4,5,6-tetrahydro-2H-[1,2']bipyridinyl-3'-carboxylic acid ethyl ester | 5.49 | 434.1 [M + H]⁺ |
| 129 | 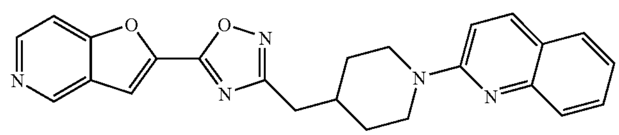 | 2-[4-(5-Furo[3,2-c]pyridin-2-yl-[1,2,4]oxadiazol-3-ylmethyl)piperidin-1-yl]-quinoline | 6.15 | 412.1 [M + H]⁺ |
| 130 | 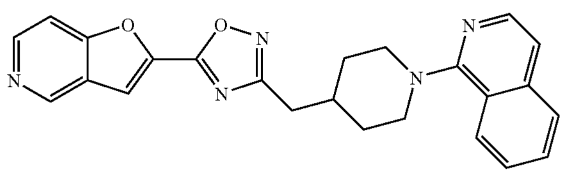 | 1-[4-(5-Furo[3,2-c]pyridin-2-yl-[1,2,4]oxadiazol-3-ylmethyl)piperidin-1-yl]-isoquinoline | 5.97 | 412.1 [M + H]⁺ |
| 131 | 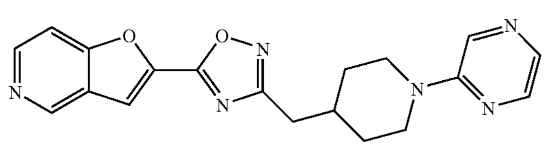 | 2-[3-(1-Pyrazin-2-yl-piperidin-4-ylmethyl)-[1,2,4]oxadiazol-5-yl]-furo[3,2-c]pyridine | 4.49 | 363.2 [M + H]⁺ |
| 132 | 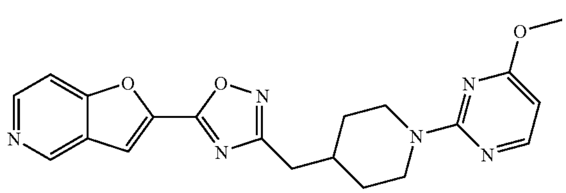 | 2-{3-[1-(4-Methoxy-pyrimidin-2-yl)-piperidin-4-ylmethyl]-[1,2,4]oxadiazol-5-yl}-furo[3,2-c]pyridine | 5.47 | 393.1 [M + H]⁺ |
| 133 | 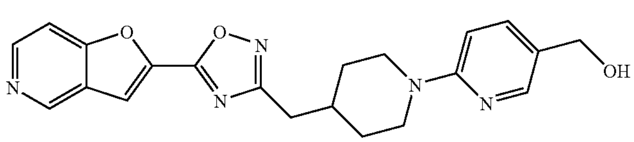 | [4-(5-Furo[3,2-c]pyridin-2-yl-[1,2,4]oxadiazol-3-ylmethyl)-3,4,5,6-tetrahydro-2H-[1,2']bipyridinyl-5'-yl]-methanol | 4.09 | 392.1 [M + H]⁺ |
| 134 | 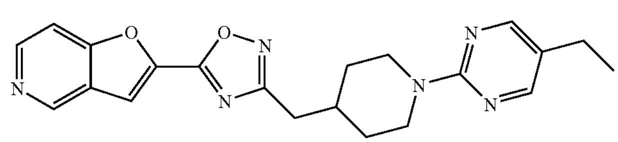 | 2-{3-[1-(5-Ethyl-pyrimidin-2-yl)-piperidin-4-ylmethyl]-[1,2,4]oxadiazol-5-yl}-furo[3,2-c]pyridine | 5.65 | 391.1 [M + H]⁺ |

TABLE 10-continued

| Eg | Structure | Name | RT (min) | m/z (ES+) |
|---|---|---|---|---|
| 135 | 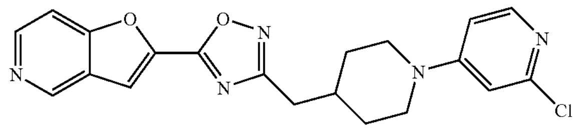 | 2'-Chloro-4-(5-furo[3,2-c]pyridin-2-yl-[1,2,4]oxadiazol-3-ylmethyl)-3,4,5,6-tetrahydro-2H-[1,4']bipyridinyl | 5.02 | 396.1 [M + H]+ |
| 136 | 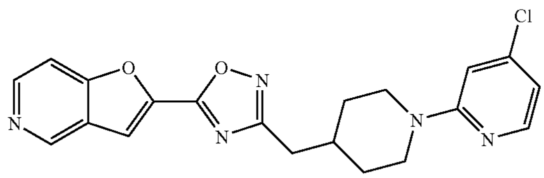 | 4'-Chloro-4-(5-furo[3,2-c]pyridin-2-yl-[1,2,4]oxadiazol-3-ylmethyl)-3,4,5,6-tetrahydro-2H-[1,2']bipyridinyl | 5.97 | 396.1 [M + H]+ |
| 137 | 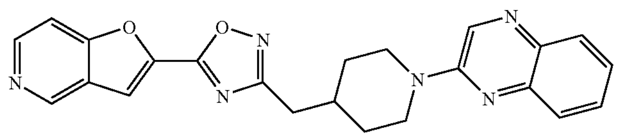 | 2-[4-(5-Furo[3,2-c]pyridin-2-yl-[1,2,4]oxadiazol-3-ylmethyl)piperidin-1-yl]-quinoxaline | 5.50 | 413.1 [M + H]+ |
| 138 | 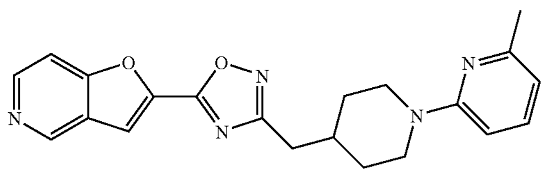 | 4-(5-Furo[3,2-c]pyridin-2-yl-[1,2,4]oxadiazol-3-ylmethyl)-6'-methyl-3,4,5,6-tetrahydro-2H-[1,2']bipyridinyl | 5.82 | 376.3 [M + H]+ |
| 139 | 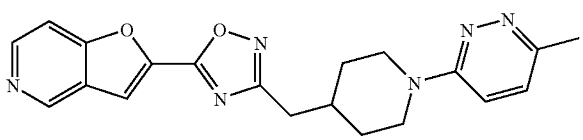 | 2-{3-[1-(6-Methyl-pyridazin-3-yl)piperidin-4-ylmethyl]-[1,2,4]oxadiazol-5-yl}-furo[3,2-c]pyridine | 4.18 | 377.4 [M + H]+ |
| 140 | 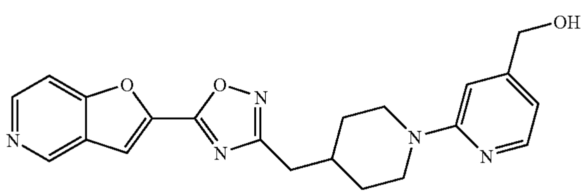 | [4-(5-Furo[3,2-c]pyridin-2-yl-[1,2,4]oxadiazol-3-ylmethyl)-3,4,5,6-tetrahydro-2H-[1,2']bipyridinyl-4'-yl]-methanol | 4.10 | 392.4 [M + H]+ |
| 141 | 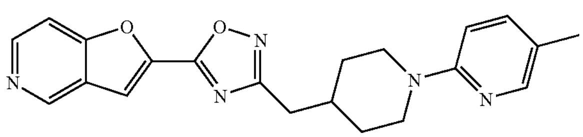 | 4-(5-Furo[3,2-c]pyridin-2-yl-[1,2,4]oxadiazol-3-ylmethyl)-5'-methyl-3,4,5,6-tetrahydro-2H-[1,2']bipyridinyl | 5.45 | 376.4 [M + H]+ |
| 142 | 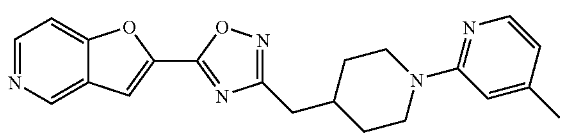 | 4-(5-Furo[3,2-c]pyridin-2-yl-[1,2,4]oxadiazol-3-ylmethyl)-4'-methyl-3,4,5,6-tetrahydro-2H-[1,2']bipyridinyl | 5.40 | 376.4 [M + H]+ |
| 143 | 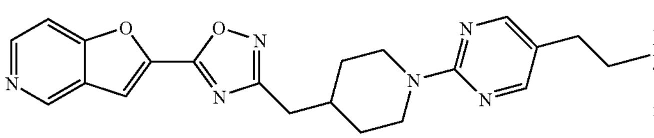 | 2-{3-[1-(5-Propyl-pyrimidin-2-yl)-piperidin-4-ylmethyl]-[1,2,4]oxadiazol-5-yl}-furo[3,2-c]pyridine | 6.15 | 405.4 [M + H]+ |
| 144 | 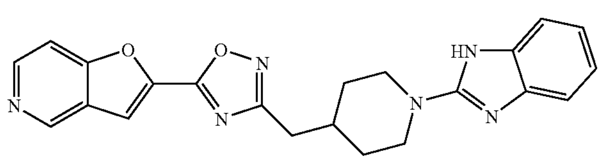 | 2-{3-[1-(1H-Benzoimidazol-2-yl)-piperidin-4-ylmethyl]-[1,2,4]oxadiazol-5-yl}-furo[3,2-c]pyridine | 4.30 | 401.4 [M + H]+ |

TABLE 10-continued

| Eg | Structure | Name | RT (min) | m/z (ES+) |
|---|---|---|---|---|
| 145 | 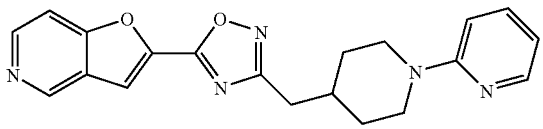 | 4-(5-Furo[3,2-c]pyridin-2-yl-[1,2,4]oxadiazol-3-ylmethyl)-3,4,5,6-tetrahydro-2H-[1,2']bipyridinyl | 5.10 | 362.3 [M + H]+ |
| 146 | 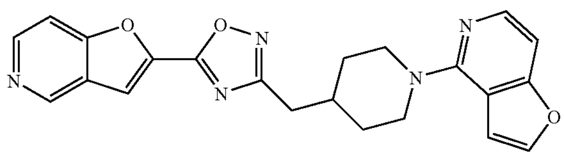 | 2-{3-[1-(Furo[3,2-c]pyridin-4-yl)piperidin-4-ylmethyl]-[1,2,4]oxadiazol-5-yl}-furo[3,2-c]pyridine | 5.35 | 402.3 [M + H]+ |
| 147 | 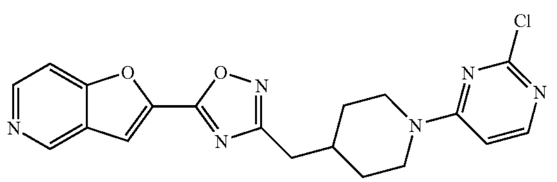 | 2-{3-[1-(2-Chloro-pyrimidin-4-yl)piperidin-4-ylmethyl]-[1,2,4]oxadiazol-5-yl}-furo[3,2-c]pyridine | 4.84 | 397.3 [M + H]+ |
| 148 | 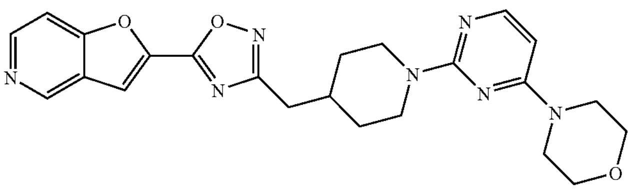 | 2-{3-[1-(4-Morpholin-4-yl-pyrimidin-2-yl)-piperidin-4-ylmethyl]-[1,2,4]oxadiazol-5-yl}-furo[3,2-c]pyridine | 4.93 | 448.4 [M + H]+ |
| 149 | 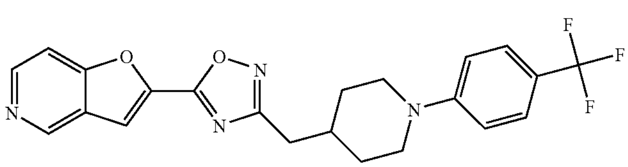 | 2-{3-[1-(4-Trifluoromethyl-phenyl)-piperidin-4-ylmethyl]-[1,2,4]oxadiazol-5-yl}-furo[3,2-c]pyridine | 6.72 | 429.3 [M + H]+ |

The biological activity of representative compounds of the invention was tested in the following assay systems:

Yeast Reporter Assay

The yeast cell-based reporter assays have previously been described in the literature (e.g. see Miret J. J. et al, 2002, J. Biol. Chem., 277:6881-6887; Campbell R. M. et al, 1999, Bioorg. Med. Chem. Lett., 9:2413-2418; King K. et al, 1990, Science, 250:121-123); WO 99/14344; WO 00/12704; and U.S. Pat. No. 6,100,042). Briefly, yeast cells have been engineered such that the endogenous yeast G-alpha (GPA1) has been deleted and replaced with G-protein chimeras constructed using multiple techniques. Additionally, the endogenous yeast alpha-cell GPCR, Step 3 has been deleted to allow for a homologous expression of a mammalian GPCR of choice. In the yeast, elements of the pheromone signaling transduction pathway, which are conserved in eukaryotic cells (for example, the mitogen-activated protein kinase pathway), drive the expression of Fus1. By placing β-galactosidase (LacZ) under the control of the Fus1 promoter (Fus1p), a system has been developed whereby receptor activation leads to an enzymatic read-out.

Yeast cells were transformed by an adaptation of the lithium acetate method described by Agatep et al, (Agatep, R. et al, 1998, Transformation of *Saccharomyces cerevisiae* by the lithium acetate/single-stranded carrier DNA/polyethylene glycol (LiAc/ss-DNA/PEG) protocol. Technical Tips Online, Trends Journals, Elsevier). Briefly, yeast cells were grown overnight on yeast tryptone plates (YT). Carrier single-stranded DNA (10 μg), 2 μg of each of two Fus1p-LacZ reporter plasmids (one with URA selection marker and one with TRP), 2 μg of GPR116 (human or mouse receptor) in yeast expression vector (2 μg origin of replication) and a lithium acetate/polyethylene glycol/TE buffer was pipetted into an Eppendorf tube. The yeast expression plasmid containing the receptor/no receptor control has a LEU marker. Yeast cells were inoculated into this mixture and the reaction proceeds at 30° C. for 60 min. The yeast cells were then heat-shocked at 42° C. for 15 min. The cells were then washed and spread on selection plates. The selection plates are synthetic defined yeast media minus LEU, URA and TRP (SD-LUT). After incubating at 30° C. for 2-3 days, colonies that grow on the selection plates were then tested in the LacZ assay.

In order to perform fluorimetric enzyme assays for β-galactosidase, yeast cells carrying the human or mouse GPR116 receptor were grown overnight in liquid SD-LUT medium to an unsaturated concentration (i.e. the cells were still dividing and had not yet reached stationary phase). They were diluted in fresh medium to an optimal assay concentration and 90 μl of yeast cells are added to 96-well black polystyrene plates (Costar). Compounds, dissolved in DMSO and diluted in a 10% DMSO solution to 10× concentration, were added to the plates and the plates placed at 30° C. for 4 h. After 4 h, the substrate for the β-galactosidase was added to each well. In these experiments, Fluorescein di(β-D-galactopyranoside) was used (FDG), a substrate for the enzyme that releases fluorescein, allowing a fluorimetric read-out. 2 μl per well of 500 μM FDG/2.5% Triton X100 was added (the detergent was necessary to render the cells permeable). After incubation of the cells with the substrate for 60 min, 20 μl per well of 1M sodium carbonate was added to terminate the reaction and enhance the fluorescent signal. The plates were then read in a fluorimeter at 485/535 nm.

The compounds of the invention give an increase in fluorescent signal of at least ~1.5-fold that of the background signal (i.e. the signal obtained in the presence of 1% DMSO without compound). Compounds of the invention which give an increase of at least 5-fold may be preferred.

cAMP Assay

A stable cell line expressing recombinant human GPR116 was established and this cell line was used to investigate the effect of compounds of the invention on intracellular levels of cyclic AMP (cAMP). The cells monolayers were washed with phosphate buffered saline and stimulated at 37° C. for 30 min with various concentrations of compound in stimulation buffer plus 1% DMSO. Cells were then lysed and cAMP content determined using the Perkin Elmer AlphaScreen™ (Amplified Luminescent Proximity Homogeneous Assay) cAMP kit. Buffers and assay conditions were as described in the manufacturer's protocol. Compounds of the invention showed a concentration-dependant increase in intracellular cAMP level.

Compounds of the invention showed a concentration-dependant increase in intracellular cAMP level and generally had an $EC_{50}$ of <10 μM. Compounds showing an $EC_{50}$ of less than 1 um in the cAMP assay may be preferred.

In Vivo Feeding Study

The effect of compounds of the invention on body weight and food and water intake may be examined in freely-feeding male Sprague-Dawley rats maintained on reverse-phase lighting. Test compounds and reference compounds are dosed by appropriate routes of administration (e.g. intraperitoneally or orally) and measurements made over the following 24 h. Rats are individually housed in polypropylene cages with metal grid floors at a temperature of 21±4° C. and 55±20% humidity. Polypropylene trays with cage pads are placed beneath each cage to detect any food spillage. Animals are maintained on a reverse phase light-dark cycle (lights off for 8 h from 09.30-17.30 h) during which time the room was illuminated by red light. Animals have free access to a standard powdered rat diet and tap water during a two week acclimatization period. The diet is contained in glass feeding jars with aluminum lids. Each lid has a 3-4 cm hole in it to allow access to the food. Animals, feeding jars and water bottles are weighed (to the nearest 0.1 g) at the onset of the dark period. The feeding jars and water bottles are subsequently measured 1, 2, 4, 6 and 24 h after animals are dosed with a compound of the invention and any significant differences between the treatment groups at baseline compared to vehicle-treated controls.

Selected compounds of the invention showed a statistically significant hypophagic effect at one or more time points at a dose of ≦100 mg/kg.

Anti-Diabetic Effects of Compounds of the Invention in an In-Vitro Model of Pancreatic Beta Cells (HIT-T15)

Cell Culture

HIT-T15 cells (passage 60) were obtained from ATCC, and were cultured in RPMI 1640 medium supplemented with 10% fetal calf serum and 30 nM sodium selenite. All experiments were done with cells at less than passage 70, in accordance with the literature, which describes altered properties of this cell line at passage numbers above 81 (Zhang H J, Walseth T F, Robertson R P. Insulin secretion and cAMP metabolism in HIT cells. Reciprocal and serial passage-dependent relationships. *Diabetes.* 1989 January; 38(1):44-8).

cAMP Assay

HIT-T15 cells were plated in standard culture medium in 96-well plates at 100,000 cells/0.1 ml/well and cultured for 24 hr and the medium was then discarded. Cells were incubated for 15 min at room temperature with 100 μl stimulation buffer (Hanks buffered salt solution, 5 mM HEPES, 0.5 mM IBMX, 0.1% BSA, pH 7.4). This was discarded and replaced with compound dilutions over the range 0.001, 0.003, 0.01, 0.03, 0.1, 0.3, 1, 3, 10, 30 μM in stimulation buffer in the presence of 0.5% DMSO. Cells were incubated at room temperature for 30 min. Then 75 ul lysis buffer (5 mM HEPES, 0.3% Tween-20, 0.1% BSA, pH 7.4) was added per well and the plate was shaken at 900 rpm for 20 min. Particulate matter was removed by centrifugation at 3000 rpm for 5 min, then the samples were transferred in duplicate to 384-well plates, and processed following the Perkin Elmer AlphaScreen cAMP assay kit instructions. Briefly 25 μl reactions were set up containing 8 μl sample, 5 μl acceptor bead mix and 12 μl detection mix, such that the concentration of the final reaction components is the same as stated in the kit instructions. Reactions were incubated at room temperature for 150 min, and the plate was read using a Packard Fusion instrument. Measurements for cAMP were compared to a standard curve of known cAMP amounts (0.01, 0.03, 0.1, 0.3, 1, 3, 10, 30, 100, 300, 1000 nM) to convert the readings to absolute cAMP amounts. Data was analysed using XLfit 3 software.

Representative compounds of the invention were found to increase cAMP at an $EC_{50}$ of less than 10 μM. Compounds showing an $EC_{50}$ of less than 1 μM in the cAMP assay may be preferred.

Insulin Secretion Assay

HIT-T15 cells were plated in standard culture medium in 12-well plates at 106 cells/1 ml/well and cultured for 3 days and the medium was then discarded. Cells were washed ×2 with supplemented Krebs-Ringer buffer (KRB) containing 119 mM NaCl, 4.74 mM KCl, 2.54 mM $CaCl_2$, 1.19 mM $MgSO_4$, 1.19 mM KH2PO4, 25 mM $NaHCO_3$, 10 mM HEPES at pH 7.4 and 0.1% bovine serum albumin. Cells were incubated with 1 ml KRB at 37° C. for 30 min which was then discarded. This was followed by a second incubation with KRB for 30 min, which was collected and used to measure basal insulin secretion levels for each well. Compound dilutions (0, 0.1, 0.3, 1, 3, 10 uM) were then added to duplicate wells in 1 ml KRB, supplemented with 5.6 mM glucose. After 30 min incubation at 37° C. samples were removed for determination of insulin levels. Measurement of insulin was done using the Mercodia Rat insulin ELISA kit, following the manufacturers instructions, with a standard curve of known insulin concentrations. For each well insulin levels were subtracted by the basal secretion level from the pre-incubation in the absence of glucose. Data was analysed using XLfit 3 software.

Representative compounds of the invention were found to increase insulin secretion at an $EC_{50}$ of less than 10 μM. Compounds showing an $EC_{50}$ of less than 1 μM in the insulin secretion assay may be preferred.

What is claimed is:

1. A compound of formula (I):

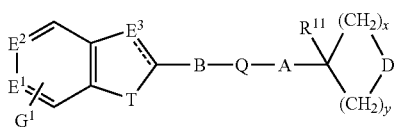

(I)

or a pharmaceutically acceptable salt or N-oxide thereof, wherein:

one of $E^1$ and $E^2$ is N and the other is N or C-$G^2$;

the dashed line together with the solid line forms an optional double bond;

when the dashed line together with the solid line forms a double bond $E^3$ is $CR^8$ or N, and when it is a single bond $E^3$ is $CHR^8$, O or $NR^2$;

T is O, S, or $NR^2$;

B is a bond;

Q is a 5-membered heteroaromatic ring;

A is $(CH_2)_n$, where one $CH_2$ group may be replaced by O or $NR^3$;

n is 0, 1, 2, 3, or 4;

$G^1$ and $G^2$ are independently hydrogen, halogen, $C_{1-4}$-alkoxy, $NR^4R^{44}$, or cyano; or $C_{1-4}$-alkyl optionally substituted by hydroxy, $NR^4R^{44}$, or oxo;

D represents $NR^1$;

$R^1$ is $C(O)OR^5$ or heteroaryl optionally be substituted by one or two groups selected from $C_{1-4}$alkyl, $C_{1-4}$alkoxy, $C_{1-4}$alkyl-OH, halogen, $C_{1-4}$-fluoroalkyl, heterocyclyl, $C(O)OC_{1-4}$alkyl;

$R^2$ and $R^3$ are independently hydrogen or $C_{1-4}$alkyl;

$R^4$ and $R^{44}$ are independently hydrogen, $C_{1-4}$alkyl, $C_{3-7}$cycloalkyl, or aryl, which may optionally be substituted with 1 or 2 substituents selected from halo, $C_{1-4}$alkyl, $CF_3$, $C_{1-4}$alkoxy, cyano, and $S(O)_2Me$; or, taken together, $R^4$ and $R^{44}$ may form a 5- or 6-membered heterocyclic ring;

$R^5$ is $C_{1-8}$ alkyl, $C_{2-8}$ alkenyl or $C_{2-8}$ alkynyl, any of which may be optionally substituted by one or more halo atoms, $NR^6R^{66}$, $OR^6$, $C(O)OR^6$, $OC(O)R^6$ or cyano, and may contain a $CH_2$ group that is replaced by O or S; or a $C_{3-7}$cycloalkyl, aryl, heterocyclyl, heteroaryl, $C_{1-4}$alkylene$C_{3-7}$cycloalkyl, $C_{1-4}$alkylenearyl, $C_{1-4}$alkyeneheterocyclyl or $C_{1-4}$ alkyleneheteroaryl, any of which may be substituted with one or more substituents selected from halo, $C_{1-4}$ alkyl, $C_{1-4}$fluoroalkyl, $OR^7$, CN, $NR^7R^{77}$, $SO_2Me$, $NO_2$ or $C(O)OR^7$;

$R^6$, $R^{66}$, $R^7$, and $R^{77}$ each independently are hydrogen or $C_{1-4}$alkyl; or, taken together, $R^6$ and $R^{66}$ or $R^7$ and $R^{77}$ may form a 5- or 6-membered heterocyclic ring;

$R^8$ is hydrogen, hydroxy, $C_{1-4}$alkoxy or benzyloxy;

$R^{11}$ hydrogen;

x is 0, 1, 2 or 3; and y is 1, 2, 3, 4 or 5;

with the proviso that x+y is 2, 3, 4 or 5.

2. The compound according to claim 1, wherein $E^3$ is CH.

3. The compound according to claim 2, wherein T is O.

4. The compound according to claim 1, wherein Q is a 5-membered heteroaromatic ring containing up to 3 heteroatoms selected from N, O and S.

5. The compound according to claim 4, wherein Q is an oxadiazolyl ring.

6. The compound according to claim 5, wherein Q is [1,2,4]oxadiazolyl.

7. The compound according to claim 1, wherein n is 1.

8. The compound according to claim 1, wherein $G^1$ is hydrogen, halogen, $C_{1-4}$alkyl, or cyano.

9. The compound according to claim 8, wherein $G^1$ is hydrogen, methyl or cyano.

10. The compound according to claim 1, wherein $G^2$ is hydrogen, methyl or cyano.

11. The compound according to claim 1, wherein $R^1$ is $C(O)OR^5$.

12. The compound according to claim 1, which is of formula (Ia):

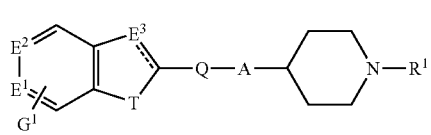

(Ia)

or a pharmaceutically acceptable salt or N-oxide thereof, wherein:

one of $E^1$ and $E^2$ is N and the other is N or C-$G^2$;

the dashed line together with the solid line forms an optional double bond;

when the dashed line together with the solid line forms a double bond $E^3$ is CH or N, and when it is a single bond $E^3$ is $CH_2$ or $NR^2$;

T is O, S, or $NR^2$;

Q is 5-membered heteroaromatic ring;

A is $(CH_2)_n$, where one $CH_2$ group may be replaced by $ONR^3$;

n is 0, 1, 2, 3, or 4;

$G^1$ and $G^2$ are independently hydrogen, halogen, $C_{1-4}$alkyl, $C_{2-4}$-alkynyl, $CF_3$, $C_{1-4}$-alkoxy, $NR^4R^{44}$, or cyano;

$R^1$ is $C(O)OR^5$ or a 5- or 6-membered nitrogen-containing heteroaryl group;

$R^2$ and $R^3$ are independently hydrogen or $C_{1-4}$alkyl;

$R^4$ and $R^{44}$ are independently hydrogen, $C_{1-4}$alkyl, $C_{3-7}$cycloalkyl, or aryl, which may optionally be substituted with 1 or 2 substituents selected from halo, $C_{1-4}$alkyl, $CF_3$, $C_{1-4}$alkoxy, cyano, and $S(O)_2Me$; or, taken together, $R^4$ and $R^{44}$ may form a 5- or 6-membered heterocyclic ring;

$R^5$ and $R^{55}$ are independently $C_{1-6}$alkyl, $C_{2-6}$alkenyl, $C_{2-6}$alkynyl, any of which may optionally be substituted by cyano, $CHal_pH_{3-p}$, $OR^6$ or $NR^6R^{66}$, or $C_{3-7}$ cycloalkyl or 4- to 7-membered heterocyclyl either of which may optionally be substituted with $C_{1-4}$alkyl, or aryl or heteroaryl either of which may optionally be substituted with 1 or 2 substituents selected from halo, $C_{1-4}$alkyl, $CF_3$, $OR^7$, $COOR^7$, cyano, $S(O)_2Me$, $NR^7R^{77}$, and nitro;

$R^6$, $R^{66}$, $R^7$, and $R^{77}$ each independently are hydrogen or $C_{1-4}$alkyl; or, taken together, $R^6$ and $R^{66}$ or $R^7$ and $R^{77}$ may independently form a 5- or 6-membered heterocyclic ring;

Hal is fluoro or chloro; and p is 1, 2, or 3.

13. A compound selected from the group consisting of:

4-[5-(4-Hydroxymethylfuro[3,2-c]pyridin-2-yl)-[1,2,4]oxadiazol-3-ylmethoxy]-piperidine-1-carboxylic acid tert-butyl ester;

4-[5-(4-Methoxymethylfuro[3,2-c]pyridine-2-yl)-[1,2,4]oxadiazole-3-ylmethoxy]piperidine-1-carboxylic acid tert-butyl ester;

4-[5-(4-Dimethylaminomethylfuro[3,2-c]pyridine-2-yl)-[1,2,4]oxadiazole-3-ylmethoxy]piperidine-1-carboxylic acid tert-butyl ester;
4-[5-(4-Pyrrolidin-1-ylmethylfuro[3,2-c]pyridine-2-yl)-[1,2,4]oxadiazole-3-ylmethoxy}-piperidine-1-carboxylic acid tert-butyl ester;
4-[5-(4-Formylfuro[3,2-c]pyridine-2-yl)-[1,2,4]oxadiazole-3-ylmethoxy]piperidine-1-carboxylic acid tert-butyl ester;
4-{[(5-Furo[3,2-c]pyridin-2-yl-[1,2,4]oxadiazol-3-ylmethyl)amino]methyl}-piperidine-1-carboxylic acid tert-butyl ester;
4-[(5-Furo[3,2-c]pyridin-2-yl-[1,2,4]oxadiazol-3-ylmethyl)amino]piperidine-1-carboxylic acid tert-butyl ester;
4-[(3-Furo[3,2-c]pyridin-2-yl-[1,2,4]oxadiazol-5-ylmethyl)amino]piperidine-1-carboxylic acid tert-butyl ester;
4-[Ethyl(5-furo[3,2-c]pyridin-2-yl-[1,2,4]oxadiazol-3-ylmethyl)amino]-piperidine-1-carboxylic acid tert-butyl ester;
4-[(5-Furo[3,2-c]pyridin-2-yl-[1,2,4]oxadiazol-3-ylmethyl)propylamino]-piperidine-1-carboxylic acid tert-butyl ester;
4-[(5-Furo[3,2-c]pyridin-2-yl-[1,2,4]oxadiazol-3-ylmethyl)methylamino]-piperidine-1-carboxylic acid tert-butyl ester;
4-[(3-Furo[3,2-c]pyridin-2-yl-[1,2,4]oxadiazol-5-ylmethyl)methylamino]-piperidine-1-carboxylic acid tert-butyl ester;
4-[Ethyl(3-furo[3,2-c]pyridin-2-yl-[1,2,4]oxadiazol-5-ylmethyl)amino]-piperidine-1-carboxylic acid tert-butyl ester;
4-(5-Thieno[2,3-c]pyridin-2-yl-[1,2,4]oxadiazol-3-yl)piperidine-1-carboxylic acid tert-butyl ester;
4-(5-Thieno[3,2-c]pyridin-2-yl-[1,2,4]oxadiazol-3-ylmethoxy)piperidine-1-carboxylic acid tert-butyl ester;
4-(5-Furo[3,2-c]pyridin-2-yl-[1,2,4]oxadiazol-3-yl)piperidine-1-carboxylic acid tert-butyl ester;
4-(5-Furo[3,2-c]pyridin-2-yl-[1,2,4]oxadiazol-3-ylmethoxy)piperidine-1-carboxylic acid tert-butyl ester;
4-(5-Thieno[2,3-c]pyridin-2-yl-[1,2,4]oxadiazol-3-ylmethoxy)piperidine-1-carboxylic acid tert-butyl ester;
4-(5-Thieno[2,3-c]pyridin-2-yl-[1,2,4]oxadiazol-3-ylmethyl)piperidine-1-carboxylic acid tert-butyl ester;
4-(5-Thieno[3,2-c]pyridin-2-yl-[1,2,4]oxadiazol-3-ylmethyl)piperidine-1-carboxylic acid tert-butyl ester;
4-(5-Furo[3,2-c]pyridin-2-yl-[1,2,4]oxadiazol-3-ylmethyl)piperidine-1-carboxylic acid tert-butyl ester;
4-(5-Thieno[2,3-c]pyridin-2-yl-[1,2,4]oxadiazol-3-yl)-piperidine-1-carboxylic acid tert-butyl ester;
4-[5-(1-Methyl-1H-pyrrolo[2,3-c]pyridin-2-yl)-[1,2,4]oxadiazol-3-ylmethyl]piperidine-1-carboxylic acid tert-butyl ester;
4-[5-(1H-Pyrrolo[2,3-c]pyridin-2-yl)-[1,2,4]oxadiazol-3-ylmethoxy]piperidine-1-carboxylic acid tert-butyl ester;
4-[5-(1H-Pyrrolo[2,3-c]pyridin-2-yl)-[1,2,4]oxadiazol-3-ylmethyl]piperidine-1-carboxylic acid tert-butyl ester;
4-(5-Furo[2,3-c]pyridin-2-yl-[1,2,4]oxadiazol-3-ylmethoxy)piperidine-1-carboxylic acid tert-butyl ester;
4-(5-Furo[2,3-c]pyridin-2-yl-[1,2,4]oxadiazol-3-yl)piperidine-1-carboxylic acid tert-butyl ester;
4-[5-(1H-Pyrrolo[2,3-c]pyridin-2-yl)-[1,2,4]oxadiazol-3-yl]-piperidine-1-carboxylic acid tert-butyl ester;
4-[5-(4-Chlorofuro[3,2-c]pyridin-2-yl)-[1,2,4]oxadiazol-3-ylmethyl]piperidine-1-carboxylic acid tert-butyl ester;
4-[5-(4-Chlorofuro[3,2-c]pyridin-2-yl)-[1,2,4]oxadiazol-3-ylmethoxy]piperidine-1-carboxylic acid tert-butyl ester;
4-(3-Furo[3,2-c]pyridin-2-yl-[1,2,4]oxadiazol-5-ylmethyl)piperidine-1-carboxylic acid tert-butyl ester;
4-(3-Furo[3,2-c]pyridin-2-yl-[1,2,4]oxadiazol-5-ylmethoxy)piperidine-1-carboxylic acid tert-butyl ester;
(3S)-3-(3-Furo[3,2-c]pyridin-2-yl-[1,2,4]oxadiazol-5-ylmethoxy)pyrrolidine-1-carboxylic acid tert-butyl ester;
(3R)-(3-Furo[3,2-c]pyridin-2-yl-[1,2,4]oxadiazol-5-ylmethoxy)pyrrolidine-1-carboxylic acid tert-butyl ester;
3-(3-Furo[3,2-c]pyridin-2-yl-[1,2,4]oxadiazol-5-ylmethoxy)azetidine-1-carboxylic acid tert-butyl ester;
3-[2-(3-Furo[3,2-c]pyridin-2-yl-[1,2,4]oxadiazol-5-yl)-ethoxy]azetidine-1-carboxylic acid tert-butyl ester;
4-(5-Furo[3,2-c]pyridin-2-yl-[1,2,4]oxadiazol-3-ylmethyl)piperidine-1-carboxylic acid propyl ester;
4-(5-Furo[3,2-c]pyridin-2-yl-[1,2,4]oxadiazol-3-ylmethyl)piperidine-1-carboxylic acid isopropyl ester;
4-(5-Furo[3,2-c]pyridin-2-yl-[1,2,4]oxadiazol-3-ylmethyl)piperidine-1-carboxylic acid ethyl ester;
4-(5-Furo[3,2-c]pyridin-2-yl-[1,2,4]oxadiazol-3-ylmethyl)piperidine-1-carboxylic acid isobutyl ester;
4-(5-Furo[3,2-c]pyridin-2-yl-[1,2,4]oxadiazol-3-ylmethyl)piperidine-1-carboxylic acid cyclopropylmethyl ester;
4-(5-Furo[3,2-c]pyridin-2-yl-[1,2,4]oxadiazol-3-ylmethyl)piperidine-1-carboxylic acid 2-methoxycarbonyl-2-methylpropyl ester;
4-(5-Furo[3,2-c]pyridin-2-yl-[1,2,4]oxadiazol-3-ylmethyl)piperidine-1-carboxylic acid (S)-sec-butyl ester;
4-(5-Furo[3,2-c]pyridin-2-yl-[1,2,4]oxadiazol-3-ylmethyl)piperidine-1-carboxylic acid cyclobutyl ester;
4-(5-Furo[3,2-c]pyridin-2-yl-[1,2,4]oxadiazol-3-ylmethyl)piperidine-1-carboxylic acid 1-methoxycarbonyl-1-methylethyl ester;
4-(5-Furo[3,2-c]pyridin-2-yl-[1,2,4]oxadiazol-3-ylmethyl)piperidine-1-carboxylic acid 1-methyl-cyclobutyl ester;
4-(5-Furo[3,2-c]pyridin-2-yl-[1,2,4]oxadiazol-3-ylmethyl)piperidine-1-carboxylic acid (R)-tetrahydrofuran-2-ylmethyl ester;
4-(5-Furo[3,2-c]pyridin-2-yl-[1,2,4]oxadiazol-3-ylmethyl)piperidine-1-carboxylic acid 2-ethoxy-ethyl ester;
4-(5-Furo[3,2-c]pyridin-2-yl-[1,2,4]oxadiazol-3-ylmethyl)piperidine-1-carboxylic acid 1-methyl-cyclopropyl ester;
2-[3-(1-Pyrimidin-2-ylpiperidin-4-ylmethyl)-[1,2,4]oxadiazol-5-yl]furo[3,2-c]pyridine;
4-(5-Furo[3,2-c]pyridin-2-yl-[1,2,4]oxadiazol-3-ylmethyl)piperidine-1-carboxylic acid 1-carboxy-1-methylethyl ester;
4-(5-Furo[3,2-c]pyridin-2-yl-[1,2,4]oxadiazol-3-ylmethyl)piperidine-1-carboxylic acid 2-carboxy-2-methylpropyl ester;
4-[5-(5-Oxyfuro[3,2-c]pyridin-2-yl)-[1,2,4]oxadiazol-3-ylmethyl]piperidine-1-carboxylic acid tert-butyl ester;
4-[5-(4-Cyanofuro[3,2-c]pyridin-2-yl)-[1,2,4]oxadiazol-3-ylmethyl]piperidine-1-carboxylic acid tert-butyl ester;
4-[5-(7-Cyanofuro[2,3-c]pyridin-2-yl)-[1,2,4]oxadiazol-3-ylmethoxy]piperidine-1-carboxylic acid tert-butyl ester;

4-[5-(4-Cyanofuro[3,2-c]pyridin-2-yl)-[1,2,4]oxadiazol-3-ylmethoxy]piperidine-1-carboxylic acid tert-butyl ester;
4-[5-(4-Cyanothieno[3,2-c]pyridin-2-yl)-[1,2,4]oxadiazol-3-ylmethoxy]piperidine-1-carboxylic acid tert-butyl ester;
4-[5-(4-Cyanofuro[3,2-c]pyridin-2-yl)-[1,2,4]oxadiazol-3-ylmethyl]piperidine-1-carboxylic acid propyl ester;
4-[5-(4-Cyanofuro[3,2-c]pyridin-2-yl)-[1,2,4]oxadiazol-3-ylmethyl]piperidine-1-carboxylic acid isopropyl ester;
4-[5-(4-Cyanofuro[3,2-c]pyridin-2-yl)-[1,2,4]oxadiazol-3-ylmethyl]piperidine-1-carboxylic acid isobutyl ester;
4-[5-(4-Cyanofuro[3,2-c]pyridin-2-yl)-[1,2,4]oxadiazol-3-ylmethyl]piperidine-1-carboxylic acid ethyl ester;
4-[5-(4-Cyanofuro[3,2-c]pyridin-2-yl)-[1,2,4]oxadiazol-3-ylmethyl]piperidine-1-carboxylic acid cyclobutyl ester;
4-[5-(4-Cyanofuro[3,2-c]pyridin-2-yl)-[1,2,4]oxadiazol-3-ylmethyl]piperidine-1-carboxylic acid tetrahydropyran-4-yl ester;
4-[5-(4-Cyanofuro[3,2-c]pyridin-2-yl)-[1,2,4]oxadiazol-3-ylmethyl]piperidine-1-carboxylic acid (R)-sec-butyl ester;
4-[5-(4-Cyanofuro[3,2-c]pyridin-2-yl)-[1,2,4]oxadiazol-3-ylmethyl]piperidine-1-carboxylic acid tetrahydrofuran-2-ylmethyl ester;
4-[5-(4-Cyanofuro[3,2-c]pyridin-2-yl)-[1,2,4]oxadiazol-3-ylmethyl]piperidine-1-carboxylic acid (R)-tetrahydrofuran-2-ylmethyl ester;
4-[5-(4-Cyanofuro[3,2-c]pyridin-2-yl)-[1,2,4]oxadiazol-3-ylmethyl]piperidine-1-carboxylic acid (R)-tetrahydrofuran-3-yl ester;
4-[5-(4-Cyanofuro[3,2-c]pyridin-2-yl)-[1,2,4]oxadiazol-3-ylmethyl]piperidine-1-carboxylic acid tetrahydrothiopyran-4-yl ester;
4-[5-(4-Cyanofuro[3,2-c]pyridin-2-yl)-[1,2,4]oxadiazol-3-ylmethyl]piperidine-1-carboxylic acid 1-methoxycarbonyl-1-methylethyl ester;
4-[5-(4-Cyanofuro[3,2-c]pyridin-2-yl)-[1,2,4]oxadiazol-3-ylmethyl]piperidine-1-carboxylic acid methoxycarbonyl methyl ester;
4-[5-(4-Cyanofuro[3,2-c]pyridin-2-yl)-[1,2,4]oxadiazol-3-ylmethyl]piperidine-1-carboxylic acid cyclopropylmethyl ester;
4-[5-(4-Cyanofuro[3,2-c]pyridin-2-yl)-[1,2,4]oxadiazol-3-ylmethyl]piperidine-1-carboxylic acid 3-ethoxy-propyl ester;
4-[5-(4-Cyanofuro[3,2-c]pyridin-2-yl)-[1,2,4]oxadiazol-3-ylmethyl]piperidine-1-carboxylic acid (S)-sec-butyl ester;
4-[5-(4-Cyanofuro[3,2-c]pyridin-2-yl)-[1,2,4]oxadiazol-3-ylmethyl]piperidine-1-carboxylic acid 3-methyl-oxetan-3-ylmethyl ester;
4-[5-(4-Cyanofuro[3,2-c]pyridin-2-yl)-[1,2,4]oxadiazol-3-ylmethyl]piperidine-1-carboxylic acid 2-ethoxyethyl ester;
4-[5-(4-Cyanofuro[3,2-c]pyridin-2-yl)-[1,2,4]oxadiazol-3-ylmethyl]piperidine-1-carboxylic acid 2-methoxy-1-methylethyl ester;
4-[5-(4-Cyanofuro[3,2-c]pyridin-2-yl)-[1,2,4]oxadiazol-3-ylmethyl]piperidine-1-carboxylic acid tetrahydrofuran-3-ylmethyl ester;
4-[5-(4-Cyanofuro[3,2-c]pyridin-2-yl)-[1,2,4]oxadiazol-3-ylmethyl]piperidine-1-carboxylic acid (S)-tetrahydrofuran-3-yl ester;
4-[5-(4-Cyanofuro[3,2-c]pyridin-2-yl)-[1,2,4]oxadiazol-3-ylmethyl]piperidine-1-carboxylic acid tetrahydropyran-2-ylmethyl ester;
4-[5-(4-Cyanofuro[3,2-c]pyridin-2-yl)-[1,2,4]oxadiazol-3-ylmethyl]piperidine-1-carboxylic acid 1-methyl-cyclopropyl ester;
4-[5-(4-Cyanofuro[3,2-c]pyridin-2-yl)-[1,2,4]oxadiazol-3-ylmethyl]piperidine-1-carboxylic acid 1-methyl-cyclobutyl ester;
4-[5-(4-Cyanofuro[3,2-c]pyridin-2-yl)-[1,2,4]oxadiazol-3-ylmethyl]piperidine-1-carboxylic acid 1-cyclopropylethyl ester;
4-[5-(4-Cyanofuro[3,2-c]pyridin-2-yl)-[1,2,4]oxadiazol-3-ylmethyl]piperidine-1-carboxylic acid 1-methyl-cyclopropylmethyl ester;
4-[5-(4-Cyanofuro[3,2-c]pyridin-2-yl)-[1,2,4]oxadiazol-3-ylmethyl]piperidine-1-carboxylic acid 2-methyl-cyclopropylmethyl ester;
4-[5-(4-Cyanofuro[3,2-c]pyridin-2-yl)-[1,2,4]oxadiazol-3-ylmethyl]piperidine-1-carboxylic acid 3-methoxypropyl ester;
4-[5-(4-Cyanofuro[3,2-c]pyridin-2-yl)-[1,2,4]oxadiazol-3-ylmethyl]piperidine-1-carboxylic acid 3-acetoxypropyl ester;
4-[5-(4-Cyanofuro[3,2-c]pyridin-2-yl)-[1,2,4]oxadiazol-3-ylmethyl]piperidine-1-carboxylic acid oxetan-3-yl ester;
4-[5-(4-Cyanofuro[3,2-c]pyridin-2-yl)-[1,2,4]oxadiazol-3-ylmethyl]piperidine-1-carboxylic acid 1-oxo-hexahydro-1$\lambda^4$-thiopyran-4-yl ester;
4-[5-(4-Cyanofuro[3,2-c]pyridin-2-yl)-[1,2,4]oxadiazol-3-ylmethyl]piperidine-1-carboxylic acid 1,1-dioxo-hexahydro-1$\lambda^6$-thiopyran-4-yl ester;
4-[5-(3-Benzyloxyfuro[3,2-c]pyridin-2-yl)-[1,2,4]oxadiazol-3-ylmethyl]-piperidine-1-carboxylic acid tert-butyl ester;
4-[5-(3-Hydroxyfuro[3,2-c]pyridin-2-yl)-[1,2,4]oxadiazol-3-ylmethyl]-piperidine-1-carboxylic acid tert-butyl ester;
4-[5-(4-Methylfuro[3,2-c]pyridin-2-yl)-[1,2,4]oxadiazol-3-ylmethyl]piperidine-1-carboxylic acid tert-butyl ester;
4-[5-(7-Iodofuro[3,2-c]pyridin-2-yl)-[1,2,4]oxadiazol-3-ylmethyl]piperidine-1-carboxylic acid tert-butyl ester;
4-Chloro-2-[3-(1-pyrimidin-2-ylpiperidin-4-yloxymethyl)-[1,2,4]oxadiazol-5-yl]furo[3,2-c]pyridine;
2-(3-((1-(3-Methoxypyridin-2-yl)piperidin-4-yl)methyl)-[1,2,4]-oxadiazol-5-yl)furo[3,2-c]pyridine;
Ethyl 6-(4-((5-(furo[3,2-c]pyridin-2-yl)-[1,2,4]-oxadiazol-3-yl)methyl)piperidin-1-yl)nicotinate;
2-{3-[1-(4,6-Dimethylpyrimidin-2-yl)piperidin-4-ylmethyl]-[1,2,4]oxadiazol-5-yl}-furo[3,2-c]pyridine;
4-(5-Furo[3,2-c]pyridin-2-yl-[1,2,4]oxadiazol-3-ylmethyl)-3,4,5,6-tetrahydro-2H-[1,2']bipyridinyl-3'-carboxylic acid ethyl ester;
2-[4-(5-Furo[3,2-c]pyridin-2-yl-[1,2,4]oxadiazol-3-ylmethyl)piperidin-1-yl]-quinoline;
1-[4-(5-Furo[3,2-c]pyridin-2-yl-[1,2,4]oxadiazol-3-ylmethyl)piperidin-1-yl]-isoquinoline;
2-[3-(1-Pyrazin-2-yl-piperidin-4-ylmethyl)-[1,2,4]oxadiazol-5-yl]-furo[3,2-c]pyridine;
2-{3-[1-(4-Methoxypyrimidin-2-yl)-piperidin-4-ylmethyl]-[1,2,4]oxadiazol-5-yl}-furo[3,2-c]pyridine;
[4-(5-Furo[3,2-c]pyridin-2-yl-[1,2,4]oxadiazol-3-ylmethyl)-3,4,5,6-tetrahydro-2H-[1,2']bipyridinyl-5'-yl]-methanol;

2-{3-[1-(5-Ethylpyrimidin-2-yl)-piperidin-4-ylmethyl]-[1,2,4]oxadiazol-5-yl}-furo[3,2-c]pyridine;

2'-Chloro-4-(5-furo[3,2-c]pyridin-2-yl-[1,2,4]oxadiazol-3-ylmethyl)-3,4,5,6-tetrahydro-2H-[1,4']bipyridinyl;

4'-Chloro-4-(5-furo[3,2-c]pyridin-2-yl-[1,2,4]oxadiazol-3-ylmethyl)-3,4,5,6-tetrahydro-2H-[1,2']bipyridinyl;

2-[4-(5-Furo[3,2-c]pyridin-2-yl-[1,2,4]oxadiazol-3-ylmethyl)piperidin-1-yl]-quinoxaline;

4-(5-Furo[3,2-c]pyridin-2-yl-[1,2,4]oxadiazol-3-ylmethyl)-6'-methyl-3,4,5,6-tetrahydro-2H-[1,2']bipyridinyl;

2-{3-[1-(6-Methylpyridazin-3-yl)piperidin-4-ylmethyl]-[1,2,4]oxadiazol-5-yl}-furo[3,2-c]pyridine;

[4-(5-Furo[3,2-c]pyridin-2-yl-[1,2,4]oxadiazol-3-ylmethyl)-3,4,5,6-tetrahydro-2H-[1,2']bipyridinyl-4'-yl]-methanol;

4-(5-Furo[3,2-c]pyridin-2-yl-[1,2,4]oxadiazol-3-ylmethyl)-5'-methyl-3,4,5,6-tetrahydro-2H-[1,2']bipyridinyl;

4-(5-Furo[3,2-c]pyridin-2-yl-[1,2,4]oxadiazol-3-ylmethyl)-4'-methyl-3,4,5,6-tetrahydro-2H-[1,2']bipyridinyl;

2-{3-[1-(5-Propylpyrimidin-2-yl)-piperidin-4-ylmethyl]-[1,2,4]oxadiazol-5-yl}-furo[3,2-c]pyridine;

2-{3-[1-(1H-Benzoimidazol-2-yl)-piperidin-4-ylmethyl]-[1,2,4]oxadiazol-5-yl}-furo[3,2-c]pyridine;

4-(5-Furo[3,2-c]pyridin-2-yl-[1,2,4]oxadiazol-3-ylmethyl)-3,4,5,6-tetrahydro-2H-[1,2']bipyridinyl;

2-{3-[1-(Furo[3,2-c]pyridin-4-yl)piperidin-4-ylmethyl]-[1,2,4]oxadiazol-5-yl}-furo[3,2-c]pyridine;

2-{3-[1-(2-Chloropyrimidin-4-yl)piperidin-4-ylmethyl]-[1,2,4]oxadiazol-5-yl}-furo[3,2-c]pyridine;

or a pharmaceutically acceptable salt or N-oxide thereof.

14. A pharmaceutical composition comprising a compound according claim 1, or a pharmaceutically acceptable salt or N-oxide thereof, and a pharmaceutically acceptable carrier.

* * * * *